(12) United States Patent
Liu et al.

(10) Patent No.: US 9,738,874 B2
(45) Date of Patent: Aug. 22, 2017

(54) POLYPEPTIDES HAVING LACCASE ACTIVITY AND POLYNUCLEOTIDES ENCODING SAME

(71) Applicant: Novozymes Inc., Davis, CA (US)

(72) Inventors: Ye Liu, Beijing (CN); Lan Tang, Beijing (CN); Junxin Duan, Beijing (CN); Yu Zhang, Beijing (CN)

(73) Assignee: Novozymes Inc., Davis, CA (US)

( * ) Notice: Subject to any disclaimer, the term of this patent is extended or adjusted under 35 U.S.C. 154(b) by 154 days.

(21) Appl. No.: 14/363,490

(22) PCT Filed: Dec. 14, 2012

(86) PCT No.: PCT/CN2012/086672
§ 371 (c)(1),
(2) Date: Jun. 6, 2014

(87) PCT Pub. No.: WO2013/087027
PCT Pub. Date: Jun. 20, 2013

(65) Prior Publication Data
US 2015/0299674 A1    Oct. 22, 2015

Related U.S. Application Data

(60) Provisional application No. 61/582,898, filed on Jan. 4, 2012.

(30) Foreign Application Priority Data

Dec. 16, 2011    (WO) ................ PCT/CN2011/084139

(51) Int. Cl.
| | | |
|---|---|---|
| *C12N 9/02* | (2006.01) |
| *C12P 19/12* | (2006.01) |
| *C12P 7/16* | (2006.01) |
| *C12P 7/10* | (2006.01) |
| *C12P 7/20* | (2006.01) |
| *C12P 19/02* | (2006.01) |
| *C11D 3/386* | (2006.01) |
| *C12P 19/14* | (2006.01) |

(52) U.S. Cl.
CPC ........ *C12N 9/0061* (2013.01); *C11D 3/38636* (2013.01); *C11D 3/38645* (2013.01); *C12P 7/10* (2013.01); *C12P 19/02* (2013.01); *C12P 19/14* (2013.01); *C12P 2203/00* (2013.01); *Y02E 50/16* (2013.01)

(58) Field of Classification Search
None
See application file for complete search history.

(56) References Cited

U.S. PATENT DOCUMENTS

2011/0281323 A1    11/2011    Shyur et al.

FOREIGN PATENT DOCUMENTS

| WO | 97/43383 A1 | 11/1997 |
| WO | 2008/076322 A2 | 6/2008 |
| WO | 2010/129940 A2 | 11/2010 |

OTHER PUBLICATIONS

Weinberg et al. J Bacteriol. Jan. 2005;187(1):336-48.*
Accession B6Q5M9. Dec. 16, 2008.*
Chica et al. Curr Opin Biotechnol. Aug. 2005;16(4):378-84.*
Sen et al. Appl Biochem Biotechnol. Dec. 2007;143(3):212-23.*
Giardina et al, 2009, Cell Mol Life Sci, vol. 67, No. 3, pp. 369-385.
Litvintseva et al, 2002, Appl Environ Microbiol, vol. 68, No. 3, pp. 1305-1311.
Zhang et al, 2011, Biotechnol Biofuel, vol. 4, No. 1, p. 12.

* cited by examiner

*Primary Examiner* — Christian Fronda
(74) *Attorney, Agent, or Firm* — Kelly Reynolds

(57) ABSTRACT

The present invention relates to isolated polypeptides having laccase activity and polynucleotides encoding the polypeptides and polynucleotides encoding the polypeptides. The invention also relates to nucleic acid constructs, vectors, and host cells comprising the polynucleotides as well as methods of producing and using the polypeptides.

5 Claims, 17 Drawing Sheets

POLYPEPTIDES HAVING LACCASE ACTIVITY AND POLYNUCLEOTIDES ENCODING SAME

CROSS-REFERENCE TO RELATED APPLICATIONS

This application is a 35 U.S.C. 371 national stage application of PCT/CN2012/086672 filed Dec. 14, 2012, which claims priority or the benefit under 35 U.S.C. 119 of Chinese PCT application no. PCT/CN2011/084139 filed Dec. 16, 2011 and U.S. provisional application no. 61/582,898 filed Jan. 4, 2012, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having laccase activity and polynucleotides encoding the polypeptides. The invention also relates to nucleic acid constructs, vectors, and host cells comprising the polynucleotides as well as methods of producing and using the polypeptides.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose can easily be fermented by yeast into ethanol.

There is a need in the art for new enzymes to increase efficiency and to provide cost-effective enzyme solutions for saccharification of cellulosic material.

The present invention provides polypeptides having laccase activity and polynucleotides encoding the polypeptides.

SUMMARY OF THE INVENTION

The present invention relates to isolated polypeptides having laccase activity selected from the group consisting of:

(a) a polypeptide having at least 60% sequence identity to the mature polypeptide of SEQ ID NO: 2, SEQ ID NO: 6, SEQ ID NO: 8, SEQ ID NO: 10, SEQ ID NO: 12, SEQ ID NO: 18, SEQ ID NO: 22, or SEQ ID NO: 24; at least 65% sequence identity to the mature polypeptide of SEQ ID NO: 34 or SEQ ID NO: 36; at least 70% sequence identity to the mature polypeptide of SEQ ID NO: 14, SEQ ID NO: 16, SEQ ID NO: 20, SEQ ID NO: 26, SEQ ID NO: 30, or SEQ ID NO: 32; at least 75% sequence identity to the mature polypeptide of SEQ ID NO: 28; or at least 85% sequence identity to the mature polypeptide of SEQ ID NO: 4;

(b) a polypeptide encoded by a polynucleotide that hybridizes under at least medium-high stringency conditions with (i) the mature polypeptide coding sequence of SEQ ID NO: 1, SEQ ID NO: 5, SEQ ID NO: 7, SEQ ID NO: 9, SEQ ID NO: 11, SEQ ID NO:17, SEQ ID NO: 21, SEQ ID NO: 23, SEQ ID NO: 33, or SEQ ID NO: 35, (ii) the cDNA sequence thereof, or (iii) the full-length complement of (i) or (ii); at least high stringency conditions with (i) the mature polypeptide coding sequence of SEQ ID NO: 13, SEQ ID NO: 15, SEQ ID NO: 19, SEQ ID NO: 25, SEQ ID NO: 27, SEQ ID NO: 29, or SEQ ID NO: 31, (ii) the cDNA sequence thereof, or (iii) the full-length complement of (i) or (ii); or at least very high stringency conditions with (i) the mature polypeptide coding sequence of SEQ ID NO: 3, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, SEQ ID NO: 5, SEQ ID NO: 7, SEQ ID NO: 9, SEQ ID NO: 11, SEQ ID NO:17, SEQ ID NO: 21, or SEQ ID NO: 23, or the cDNA sequences thereof; at least 65% sequence identity to the mature polypeptide coding sequence of SEQ ID NO: 33 or SEQ ID NO: 35, or the cDNA sequences thereof; at least 70% sequence identity to the mature polypeptide coding sequence of SEQ ID NO: 13, SEQ ID NO: 15, SEQ ID NO: 19, SEQ ID NO: 25, SEQ ID NO: 29, or SEQ ID NO: 31, or the cDNA sequences thereof; at least 75% sequence identity to the mature polypeptide coding sequence of SEQ ID NO: 27 or the cDNA sequence thereof; or at least 85% sequence identity to the mature polypeptide coding sequence of SEQ ID NO: 3 or the cDNA sequence thereof;

(d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO; 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36 comprising a substitution, deletion, and/or insertion at one or more (e.g., several) positions; and (e) a fragment of the polypeptide of (a), (b), (c), or (d) that has laccase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading a cellulosic material, comprising: treating the cellulosic material with an enzyme composition in the presence of a polypeptide having laccase activity of the present invention.

The present invention also relates to processes of producing a fermentation product, comprising: (a) saccharifying a cellulosic material with an enzyme composition in the presence of a polypeptide having laccase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having laccase activity of the present invention.

The present invention also relates to processes for detoxifying a pre-treated lignocellulose-containing material comprising subjecting the pre-treated lignocellulose-containing material to a polypeptide having laccase activity of the present invention.

The present invention also relates to processes of producing a fermentation product, comprising: (a) pretreating a cellulosic material, (b) detoxifying the pretreated cellulosic material with a polypeptide having laccase activity of the present invention; (c) saccharifying the detoxified cellulosic material with an enzyme composition optionally in the presence of the polypeptide having laccase activity; (d) fermenting the saccharified cellulosic material with one or more (e.g., several) fermenting microorganisms to produce the fermentation product; and (e) recovering the fermentation product from the fermentation.

The present invention also relates to processes of producing a fermentation product, comprising: (a) pretreating a cellulosic material, (b) saccharifying the pretreated cellulosic material with an enzyme composition in the presence of a polypeptide having laccase activity of the present invention; (c) fermenting the saccharified cellulosic material with one or more (e.g., several) fermenting microorganisms to produce the fermentation product; and (d) recovering the fermentation product from the fermentation.

The present invention also relates to a polynucleotide encoding a signal peptide comprising or consisting of amino acids 1 to 20 of SEQ ID NO: 2, amino acids 1 to 25 of SEQ ID NO: 4, amino acids 1 to 19 of SEQ ID NO: 6, amino acids 1 to 23 of SEQ ID NO: 8, amino acids 1 to 19 of SEQ ID NO: 10, amino acids 1 to 23 of SEQ ID NO: 12, amino acids 1 to 21 of SEQ ID NO: 14, amino acids 1 to 16 of SEQ ID NO: 16, amino acids 1 to 23 of SEQ ID NO: 18, amino acids 1 to 20 of SEQ ID NO: 20, amino acids 1 to 19 of SEQ ID NO: 22, amino acids 1 to 20 of SEQ ID NO: 24, amino acids 1 to 21 of SEQ ID NO: 26, amino acids 1 to 22 of SEQ ID NO: 28, amino acids 1 to 22 of SEQ ID NO: 30, amino acids 1 to 21 of SEQ ID NO: 32, amino acids 1 to 17 of SEQ ID NO: 34, or amino acids 1 to 21 of SEQ ID NO: 36, or which is operably linked to a gene encoding a protein; nucleic acid constructs, expression vectors, and recombinant host cells comprising the polynucleotides; and methods of producing a protein.

DEFINITIONS

Figure 1:
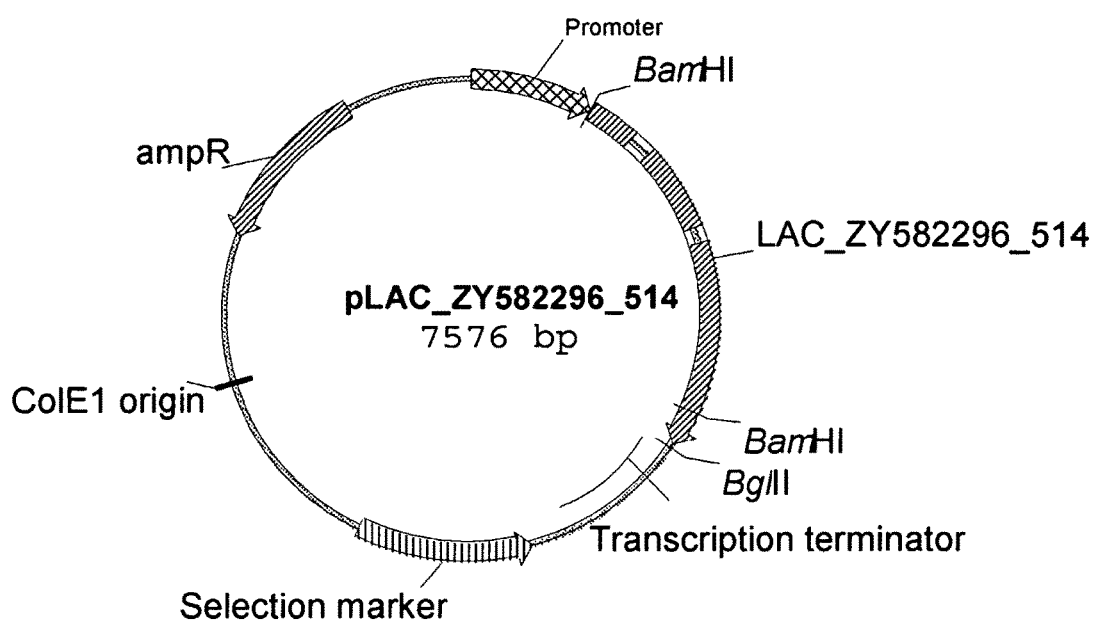
FIG. 1 shows a restriction map of pLAC_ZY582296_514.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenylacetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et a, 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be, present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teed, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.G. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has laccase activity. In one aspect, a fragment contains at least 485 amino acid residues, e.g., at least 510 amino acid residues or at least 535 amino acid residues of SEQ ID NO: 2. In another aspect, a fragment contains at least 510 amino acid residues, e.g., at least 540 amino acid residues or at least 570 amino acid residues of SEQ ID NO: 4. In another aspect, a fragment contains at least 475 amino acid residues, e.g., at least 505 amino acid residues or at least 535 amino acid residues of SEQ ID NO: 6. In another aspect, a fragment contains at least 475 amino acid residues, e.g., at least 505 amino acid residues or at least 535 amino acid residues of SEQ ID NO: 8. In another aspect, a fragment contains at least 540 amino acid residues, e.g., at least 570 amino acid residues or at least 600 amino acid residues of SEQ ID NO: 10. In another aspect, a fragment contains at least 475 amino acid residues, e.g., at least 500 amino acid residues or at least 525 amino acid residues of SEQ ID NO: 12. In another aspect, a fragment contains at least 495 amino acid residues, e.g., at least 525 amino acid residues or at least 555 amino acid residues of SEQ ID NO: 14. In another aspect, a fragment contains at least 470 amino acid residues, e.g., at least 495 amino acid residues or at least 520 amino acid residues of SEQ ID NO: 16. In another aspect, a fragment contains at least 490 amino acid residues, e.g., at least 520 amino acid residues or at least 550 amino acid residues of SEQ ID NO: 18. In another aspect, a fragment contains at least 470 amino acid residues, e.g., at least 500 amino acid residues or at least 530 amino acid residues of SEQ ID NO: 20. In another aspect, a fragment contains at least 490 amino acid residues, e.g., at least 520 amino acid residues or at least 550 amino acid residues of SEQ ID NO: 22. In another aspect, a fragment contains at least 465 amino acid residues, e.g., at least 490 amino acid residues or at least 515 amino acid residues of SEQ ID NO: 24. In another aspect, a fragment contains at least 480 amino acid residues, e.g., at least 510 amino acid residues or at least 540 amino acid residues of SEQ ID NO: 26. In another aspect, a fragment contains at least 470 amino acid residues, e.g., at least 500 amino acid residues or at least 530 amino acid residues of SEQ ID NO: 28. In another aspect, a fragment contains at least 500 amino acid residues, e.g., at least 530 amino acid residues or at least 560 amino acid residues of SEQ ID NO: 30. In another aspect, a fragment contains at least 510 amino acid residues, e.g., at least 540 amino acid residues or at least 570 amino acid residues of SEQ ID NO: 32. In another aspect, a fragment contains at least 480 amino acid residues, e.g., at least 510 amino acid residues or at least 540 amino acid residues of SEQ ID NO: 34. In another aspect, a fragment contains at least 490 amino acid residues, e.g., at least 520 amino acid residues or at least 550 amino acid residues of SEQ ID NO: 36.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Laccase: The term "laccase" means a polyphenol oxidase (EC 1.10.3.2) that catalyzes the oxidation of a variety of inorganic and aromatic compounds, particularly phenols, with the concomitant reduction of molecular oxygen to water.

Laccase activity can be determined from the oxidation of syringaldazine under aerobic conditions. The violet color produced is photometered at 530 nm. The analytical conditions are 19 mM syringaldazine, 23.2 mM sodium acetate pH 5.5, 30° C., 1 minute reaction time. One laccase unit (LACU) is the amount of enzyme that catalyzes the conversion of 1.0 micromole of syringaldazine per minute at these conditions.

Laccase activity can also be determined from the oxidation of syringaldazine under aerobic conditions. The violet color produced is photometered at 530 nm. The analytical conditions are 19 mM syringaldazine, 23 mM Tris/maleate buffer, pH 7.5, 30° C., 1 min. reaction time. One laccase unit (LAMU) is the amount of enzyme that catalyzes the conversion of 1.0 µmole syringaldazine per minute at these conditions.

Laccase activity can also be measured using 10-(2-hydroxyethyl)-phenoxazine (HEPO) as substrate. HEPO is synthesized using the same procedure as described for 10-(2-hydroxyethyl)-phenothiazine, (Cauquil, 1960, *Bulletin de la Society Chemique de France* p. 1049). In the presence of oxygen laccases oxidize HEPO to a HEPO radical that can be monitored photometrically at 528 nm.

Laccase activity can also be measured using 2,2'-azino-bis(3-ethylbenzothiazoline-6-sulfonic acid)diammonium salt (ABTS, CAS number: 30931-67-0) as substrate in 100 mM sodium acetate pH 4 and measuring the absorbance at 405 nm according to the procedure described in Example 15.

The laccases of the present invention have at least 20%, e.g., at least 40%, at least 50%, at least 60%, at least 70%, at least 80%, at least 90%, at least 95%, and at least 100% of the laccase activity of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 21 to 591 of SEQ ID NO: 2 (P24DW3) based on the SignalP program (Nielsen et al., 1997, *Protein Engineering* 10: 1-6) that predicts amino acids 1 to 20 of SEQ ID NO: 2 are a signal peptide. In another aspect, the mature polypeptide is amino acids 26 to 610 of SEQ ID NO: 4 (P24EKS) based on the SignalP program that predicts amino acids 1 to 25 of SEQ ID NO: 4 are a signal peptide. In another aspect, the mature polypeptide is amino acids 20 to 585 of SEQ ID NO: 6 (P24EKN) based on the SignalP program that predicts amino acids 1 to 19 of SEQ ID NO: 6 are a signal peptide. In another aspect, the mature polypeptide is amino acids 24 to 590 of SEQ ID NO: 8 (P24F2C) based on the SignalP program that predicts amino acids 1 to 23 of SEQ ID NO: 8 are a signal peptide. In another aspect, the mature polypeptide is amino acids 20 to 617 of SEQ ID NO: 10 (P24F2D) based on the SignalP program that predicts amino acids 1 to 19 of SEQ ID NO: 10 are a signal peptide. In another aspect, the mature polypeptide is amino acids 24 to 576 of SEQ ID NO: 12 (P24F2E) based on the SignalP program that predicts amino acids 1 to 23 of SEQ ID NO 12 are a signal peptide. In another aspect, the mature polypeptide is amino acids 22 to 606 of SEQ ID NO: 14 (P24JJR) based on the SignalP program that predicts amino acids 0.1 to 21 of SEQ ID NO: 14 are a signal peptide. In another aspect, the mature polypeptide is amino acids 17 to 559 of SEQ ID NO: 16 based on the SignalP program that predicts amino acids 1 to 16 of SEQ ID NO: 16 (P24J2K) are a signal peptide. In another aspect, the mature polypeptide is amino acids 24 to 603 of SEQ ID NO: 18 (P24HYC) based on the SignalP program that predicts amino acids 1 to 23 of SEQ ID NO: 18 are a signal peptide. In another aspect, the mature polypeptide is amino acids 21 to 581 of SEQ ID NO: 20 (P24JJQ) based on the SignalP program that predicts amino acids 1 to 20 of SEQ ID NO: 20 are a signal peptide. In another aspect, the mature polypeptide is amino acids 20 to 596 of SEQ ID NO: 22 (P24J2J) based on the SignalP program that predicts amino acids 1 to 19 of SEQ ID NO: 22 are a signal peptide. In another aspect, the mature polypeptide is amino acids 21 to 563 (P24GU5) of SEQ ID NO: 24 based on the SignalP program that predicts amino acids 1 to 20 of SEQ ID NO: 24 are a signal peptide. In another aspect, the mature polypeptide is amino acids 22 to 593 of SEQ ID NO: 26 (P24GU8) based on the SignalP program that predicts amino acids 1 to 21 of SEQ ID NO: 26 are a signal peptide. In another aspect, the mature polypeptide is amino acids 23 to 584 of SEQ ID NO: 28 (P33BS4) based on the SignalP program that predicts amino acids 1 to 22 of SEQ ID NO: 28 are a signal peptide. In another aspect, the mature polypeptide is amino acids 23 to 606 of SEQ ID NO: 30 (P33BS5) based on the SignalP program that predicts amino acids 1 to 22 of SEQ ID NO: 30 are a signal peptide. In another aspect, the mature polypeptide is amino acids 22 to 619 of SEQ ID NO: 32 (P33BS6) based on the SignalP program that predicts amino acids 1 to 21 of SEQ ID NO: 32 are a signal peptide. In another aspect, the mature polypeptide is amino acids 18 to 585 of SEQ ID NO: 34 (P33BS7) based on the SignalP program that predicts amino acids 1 to 17 of SEQ ID NO: 34 are a signal peptide. In another aspect, the mature polypeptide is amino acids 22 to 604 of SEQ ID NO: 36 (P33BSB) based on the SignalP program that predicts amino acids 1 to 21 of SEQ ID NO: 36 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having laccase activity. In one aspect, the mature polypeptide coding sequence is nucleotides 61 to 1944 of SEQ ID NO: 1 (D82JWT) or the cDNA sequence thereof based on the SignalP program (Nielsen et al., 1997, supra) that predicts nucleotides 1 to 60 of SEQ ID NO: 1 encode a signal peptide. In another aspect, the mature polypeptide coding sequence is nucleotides 76 to 2248 of SEQ ID NO: 3 (D82MAT) or the cDNA sequence thereof based on the SignalP program that predicts nucleotides 1 to 75 of SEQ ID NO: 3 encode a signal peptide. In another aspect, the mature polypeptide coding sequence is nucleotides 58 to 2135 of SEQ ID NO: 5 (D82MAP) or the cDNA sequence thereof based on the SignalP program that predicts nucleotides 1 to 57 of SEQ ID NO: 5 encode a signal peptide. In another aspect, the mature polypeptide coding sequence is nucleotides 70 to 1886 of SEQ ID NO: 7 (D82NBW) or the cDNA sequence thereof based on the SignalP program that predicts nucleotides 1 to 69 of SEQ ID NO: 7 encode a signal peptide. In another aspect, the mature polypeptide coding sequence is nucleotides 58 to 2076 of SEQ ID NO: 9 (D82NBX) or the cDNA sequence thereof based on the SignalP program that predicts nucleotides 1 to 57 of SEQ ID NO: 9 encode a signal peptide. In another aspect, the mature polypeptide coding sequence is nucleotides 70 to 1788 of SEQ ID NO: 11 (D82NBY) or the cDNA sequence thereof based on the SignalP program that predicts nucleotides 1 to 69 of SEQ ID NO: 11 encode a signal peptide. In another aspect, the mature polypeptide coding sequence is nucleotides 64 to 2163 of SEQ ID NO: 13 (D82XFE) or the cDNA sequence thereof based on the SignalP program that predicts nucleotides 1 to 63 of SEQ ID NO: 13 encode a signal peptide. In another aspect, the mature polypeptide coding sequence is nucleotides 49 to 1723 of SEQ ID NO: 15 (D82TPR) or the cDNA sequence thereof based on the SignalP program that predicts nucleotides 1 to 48 of SEQ ID NO: 15 encode a signal peptide. In another aspect, the mature polypeptide coding sequence is nucleotides 70 to 1876 of SEQ ID NO: 17 (D82T79) or the cDNA sequence thereof based on the SignalP program that predicts nucleotides 1 to 69 of SEQ ID NO: 17 encode a signal peptide. In another aspect, the mature polypeptide coding sequence is nucleotides 61 to 1923 of SEQ ID NO: 19 (D82XFD) or the cDNA sequence thereof based on the SignalP program that predicts nucleotides 1 to 60 of SEQ ID NO: 19 encode a signal peptide. In another aspect, the mature polypeptide coding sequence is nucleotides 58 to 1889 of SEQ ID NO: 21 (D82TPQ) or the cDNA sequence thereof based on the SignalP program that predicts nucleotides 1 to 57 of SEQ ID NO: 21 encode a signal peptide. In another aspect, the mature polypeptide coding sequence is nucleotides 61 to 2112 of SEQ ID NO: 23 (D82RVX) or the cDNA sequence thereof based on the SignalP program that predicts nucleotides 1 to 60 of SEQ ID NO: 23 encode a signal peptide. In another aspect, the mature polypeptide coding sequence is nucleotides 64 to 2108 of SEQ ID NO: 25 (D82RW4) or the cDNA sequence thereof based on the SignalP program that predicts nucleotides 1 to 63 of SEQ ID NO: 25 encode a signal peptide. In another aspect, the mature polypeptide coding sequence is nucleotides 67 to 1964 of SEQ ID NO: 27 (D14E4X) or the cDNA sequence thereof based on the SignalP program that predicts nucleotides 1 to 66 of SEQ ID NO: 27 encode a signal peptide. In another aspect, the mature polypeptide coding sequence is nucleotides 67 to 1987 of SEQ ID NO: 29 (D14E4Y) or the cDNA sequence thereof based on the SignalP program that predicts nucleotides 1 to 66 of SEQ ID NO: 29 encode a signal peptide. In another aspect, the mature polypeptide coding sequence is nucleotides 64 to 2352 of SEQ ID NO: 31 (D14E4Z) or the cDNA sequence thereof based on the SignalP program that predicts nucleotides 1 to 63 of SEQ ID NO: 31 encode a signal peptide. In another aspect, the mature polypeptide coding sequence is nucleotides 52 to 1924 of SEQ ID NO: 33 (D14E51) or the cDNA sequence thereof based on the SignalP program that predicts nucleotides 1 to 51 of SEQ ID NO: 33 encode a signal peptide. In another aspect, the mature polypeptide coding sequence is nucleotides 64 to 2050 of SEQ ID NO: 35 (D14E55) or the cDNA sequence thereof based on the SignalP program that predicts nucleotides 1 to 63 of SEQ ID NO: 35 encode a signal peptide.

Mediator: The term "chemical mediator" (or "mediator" may be used interchangeably herein) is defined herein as a chemical compound which acts as a redox mediator to effectively shuttle electrons between a laccase and the substrate, e.g., cellulosic material. Chemical mediators are also known as enhancers and accelerators in the art.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a GH61 polypeptide having cellulolytic enhancing activity for 1-7 days at a suitable temperature, such as 40° C.-80° C., e.g., 50° C., 55° C., 60° C., 65° C., or 70° C., and a suitable pH, such as 4-9, e.g., 5.0, 5.5, 6.0, 6.5, or 7.0, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having laccase activity. In one aspect, a subsequence contains at least 1455 nucleotides, e.g., at least 1530 nucleotides or at least 1605 nucleotides of SEQ ID NO: 1. In another aspect, a subsequence contains at least 1530 nucleotides, e.g., at least 1620 nucleotides or at least 1710 nucleotides of SEQ ID NO: 3. In another aspect, a subsequence contains at least 1425 nucleotides, e.g., at least 1515 nucleotides or at least 1605 nucleotides of SEQ ID NO: 5. In another aspect, a subsequence contains at least 1425 nucleotides, e.g., at least 1515 nucleotides or at least 1605 nucleotides of SEQ ID NO: 7. In another aspect, a subsequence contains at least 1620 nucleotides, e.g., at least 1710 nucleotides or at least 1800 nucleotides of SEQ ID NO: 9. In another aspect, a subsequence contains at least 1425 nucleotides, e.g., at least 1500 nucleotides or at least 1575 nucleotides of SEQ ID NO: 11. In another aspect, a subsequence contains at least 1485 nucleotides, e.g., at least 1575 nucleotides or at least 1665 nucleotides of SEQ ID NO: 13. In another aspect, a subsequence contains at least 1410 nucleotides, e.g., at least 1485 nucleotides or at least 1560 nucleotides of SEQ ID NO: 15. In another aspect, a subsequence contains at least 1470 nucleotides, e.g., at least 1560 nucleotides or at least 1650 nucleotides of SEQ ID NO: 17. In another aspect, a subsequence contains at least 1410 nucleotides, e.g., at least 1500 nucleotides or at least 1590 nucleotides of SEQ ID NO: 19. In another aspect, a subsequence contains at least 1470 nucleotides, e.g., at least 1560 nucleotides or at least 1650 nucleotides of SEQ ID NO: 21. In another aspect, a subsequence contains at least 1395 nucleotides, e.g., at least 1470 nucleotides or at least 1545 nucleotides of SEQ ID NO: 23. In another aspect, a subsequence contains at least 1440 nucleotides, e.g., at least 1530 nucleotides or at least 1620 nucleotides of SEQ ID NO: 25. In another aspect, a subsequence contains at least 1410 nucleotides, e.g., at least 1500 nucleotides or at least 1590 nucleotides of SEQ ID NO: 27. In another aspect, a subsequence contains at least 1500 nucleotides, e.g., at least 1590 nucleotides or at least 1680 nucleotides of SEQ ID NO: 29. In another aspect, a subsequence contains at least 1530 nucleotides, e.g., at least 1620 nucleotides or at least 1710 nucleotides of SEQ ID NO: 31. In another aspect, a subsequence contains at least 1440 nucleotides, e.g., at least 1530 nucleotides or at least 1620 nucleotides of SEQ ID NO: 33. In another aspect, a subsequence contains at least 1470 nucleotides, e.g., at least 1560 nucleotides or at least 1650 nucleotides of SEQ ID NO: 35.

Variant: The term "variant" means a polypeptide having laccase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH)

assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity can be determined with 0.2% AZCL-arabinoxylan as substrate in 0.01% TRITON® X-100 and 200 mM sodium phosphate buffer pH 6 at 37° C. or 0.2% AZCL-xylan as substrate in 0.01% TRITON® X-100 and 20 mM sodium acetate buffer pH 5.0 at 50° C. (see Example 17). One unit of xylanase activity is defined as 1.0 μmole of azurine produced per minute at 37° C., pH 6 from 0.2% AZCL-arabinoxylan as substrate in 200 mM sodium phosphate pH 6 or at 50° C., pH 5 from 0.2% AZCL-xylan as substrate in 20 mM sodium acetate pH 5.

DETAILED DESCRIPTION OF THE INVENTION

Polypeptides Having Laccase Activity

In an embodiment, the present invention relates to isolated polypeptides having a sequence identity to the mature polypeptide of SEQ ID NO: 2, SEQ ID NO: 6, SEQ ID NO: 8, SEQ ID NO: 10, SEQ ID NO: 12, SEQ ID NO:18, SEQ ID NO: 22, or SEQ ID NO: 24 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 34 or SEQ ID NO: 36 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 14, SEQ ID NO: 16, SEQ ID NO: 20, SEQ ID NO: 26, SEQ ID NO: 30, or SEQ ID NO: 32 of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 28 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 4 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36 or an allelic variant thereof; or is a fragment thereof having laccase activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36. In another aspect, the polypeptide comprises or consists of amino acids 21 to 591 of SEQ ID NO: 2, amino acids 26 to 610 of SEQ ID NO: 4, amino acids 20 to 585 of SEQ ID NO: 6, amino acids 24 to 590 of SEQ ID NO: 8, amino acids 20 to 617 of SEQ ID NO: 10, amino acids 24 to 576 of SEQ ID NO: 12, amino acids 22 to 606 of SEQ ID NO: 14, amino acids 17 to 559 of SEQ ID NO: 16, amino acids 24 to 603 of SEQ ID NO: 18, amino acids 21 to 581 of SEQ ID NO: 20, amino acids 20 to 596 of SEQ ID NO: 22, amino acids 21 to 563 of SEQ ID NO: 24, amino acids 22 to 593 of SEQ ID NO: 26, amino acids 23 to 584 of SEQ ID NO: 28, amino acids 23 to 606 of SEQ ID NO: 30, amino acids 22 to 619 of SEQ ID NO: 32, amino acids 18 to 585 of SEQ ID NO: 34, or amino acids 22 to 604 of SEQ ID NO: 36.

In another embodiment, the present invention relates to isolated polypeptides having laccase activity encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35, (ii) the cDNA sequence thereof, or (iii) the full-length complement of (i) or (ii) (Sambrook et al., 1989, *Molecular Cloning, A Laboratory Manual*, 2d edition, Cold Spring Harbor, New York).

The polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35, or a subsequence thereof, as well as the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36, or a fragment thereof, may be used to design nucleic acid probes to identify and clone DNA encoding polypeptides having laccase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having laccase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35, the mature polypeptide coding sequence thereof, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35; (ii) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35; the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35; or the cDNA sequence thereof.

In another embodiment, the present invention relates to isolated polypeptides having laccase activity encoded by polynucleotides having a sequence identity to the mature polypeptide coding sequence of SEQ ID NO: 1, SEQ ID NO: 5, SEQ ID NO: 7, SEQ ID NO: 9, SEQ ID NO: 11, SEQ ID NO:17, SEQ ID NO: 21, or SEQ ID NO: 23 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 33 or SEQ ID NO: 35 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 13, SEQ ID NO: 15, SEQ ID NO: 19, SEQ ID NO: 25, SEQ ID NO: 29, or SEQ ID NO: 31 of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 27 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 3 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for laccase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Laccase Activity

A polypeptide having laccase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a *Malbranchea* polypeptide. In another aspect, the polypeptide is a *Malbranchea cinnamomea* polypeptide. In another aspect, the polypeptide is a *Rhizomucor* polypeptide. In another aspect, the polypeptide is a *Rhizomucor pusillus* polypeptide. In another aspect, the polypeptide is a *Penicillium* polypeptide. In another aspect, the polypeptide is a *Penicillium emersonii* polypeptide. In another aspect, the polypeptide is a *Penicillium oxalicum* polypeptide. In another aspect, the polypeptide is a *Thermoascus* polypeptide. In another aspect, the polypeptide is a *Thermoascus aurantiacus* polypeptide. In another aspect, the polypeptide is a *Corynascus* polypeptide. In another aspect, the polypeptide is a *Corynascus thermophilus* polypeptide. In another aspect, the polypeptide is a *Corynascus thermophilus* CBS 174.70 polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding polypeptides of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Malbranchea, Rhizomucor, Penicillium, Thermoascus,* or *Corynascus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35, or the cDNA sequences thereof, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), Bacillus licheniformis alpha-amylase (amyL), and Escherichia coli ribosomal RNA (rmB).

Preferred terminators for filamentous fungal host cells are obtained from the genes for Aspergillus nidulans acetamidase, Aspergillus nidulans anthranilate synthase, Aspergillus niger glucoamylase, Aspergillus niger alpha-glucosidase, Aspergillus oryzae TAKA amylase, Fusarium oxysporum trypsin-like protease, Trichoderma reesei beta-glucosidase, Trichoderma reesei cellobiohydrolase I, Trichoderma reesei cellobiohydrolase II, Trichoderma reesei endoglucanase I, Trichoderma reesei endoglucanase II, Trichoderma reesei endoglucanase III, Trichoderma reesei endoglucanase V, Trichoderma reesei xylanase I, Trichoderma reesei xylanase II, Trichoderma reesei xylanase III, Trichoderma reesei beta-xylosidase, and Trichoderma reesei translation elongation factor.

Preferred terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a Bacillus thuringiensis cryIIIA gene (WO 94/25612) and a Bacillus subtilis SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for Aspergillus oryzae TAKA amylase and Aspergillus nidulans triose phosphate isomerase.

Suitable leaders for yeast host cells are obtained from the genes for Saccharomyces cerevisiae enolase (ENO-1), Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for Aspergillus nidulans anthranilate synthase, Aspergillus niger glucoamylase, Aspergillus niger alpha-glucosidase Aspergillus oryzae TAKA amylase, and Fusarium oxysporum trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide, may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for Bacillus NCIB 11837 maltogenic amylase, Bacillus licheniformis subtilisin, Bacillus licheniformis beta-lactamase, Bacillus stearothermophilus alpha-amylase, Bacillus, stearothermophilus neutral proteases (nprT, nprS, nprM), and Bacillus subtilis prsA. Further signal peptides are described by Simonen and Palva, 1993, Microbiological Reviews 57: 109-137.

Effective signal peptide coding sequences for filamentous fungal host cells are the signal peptide coding sequences obtained from the genes for Aspergillus niger neutral amylase, Aspergillus niger glucoamylase, Aspergillus oryzae TAKA amylase, Humicola insolens cellulase, Humicola insolens endoglucanase V, Humicola lanuginosa lipase, and Rhizomucor miehei aspartic proteinase.

Useful signal peptides for yeast host cells are obtained from the genes for Saccharomyces cerevisiae alpha-factor and Saccharomyces cerevisiae invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for Bacillus subtilis alkaline protease (aprE), Bacillus subtilis neutral protease (nprT), Myceliophthora thermophila laccase (WO 95/33836), Rhizomucor miehei aspartic proteinase, and Saccharomyces cerevisiae alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and tip operator systems. In yeast, the ADH2 system or GAL1 system may be used. In filamentous fungi, the Aspergillus niger glucoamylase promoter, Aspergillus oryzae TAKA alpha-amylase promoter, and Aspergillus oryzae glucoamylase promoter, Trichoderma reesei cellobiohydrolase I promoter, and Trichoderma reesei cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are Bacillus licheniformis or Bacillus subtilis dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are Aspergillus nidulans or Aspergillus oryzae amdS and pyrG genes and a Streptomyces hygroscopicus bar gene. Preferred for use in a Trichoderma cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in E. coli, and pUB110, pE194, pTA1060, and pAMβ1 permitting replication in Bacillus.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication.

The host cell may be any cell useful in the recombinant production of a polypeptide of the present invention, e.g., a prokaryote or a eukaryote.

The prokaryotic host cell may be any Gram-positive or Gram-negative bacterium.

Gram-positive bacteria include, but are not limited to; *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteria.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by, Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteria. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carisbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora*

*crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In one aspect, the cell is a *Malbranchea* cell. In another aspect, the cell is a *Malbranchea cinnamomea* cell. In another aspect, the cell is a *Rhizomucor* cell. In another aspect, the cell is a *Rhizomucor pusillus* cell. In another aspect, the cell is a *Penicillium* cell. In another aspect, the cell is a *Penicillium ermersonii* cell. In another aspect, the cell is a *Penicillium oxalicum* cell. In another aspect, the cell is a *Thermoascus* cell. In another aspect, the cell is a *Thermoascus aurantiacus* cell. In another aspect, the cell is a *Corynascus* cell. In another aspect, the cell is a *Corynascus thermophilus* cell. In another aspect, the cell is a *Corynascus* cell. In another aspect, the cell is *Corynascus thermophilus* CBS 174.70.

The present invention also relates to methods of producing a polypeptide of the present invention, comprising (a) cultivating a recombinant host cell of the present invention under conditions conducive for production of the polypeptide; and optionally (b) recovering the polypeptide.

The cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising a polypeptide of the present invention is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998; *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, Plant Cell Physiol. 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising (a) cultivating a transgenic plant or a plant cell comprising a polynucleotide encoding the polypeptide under conditions conducive for production of the polypeptide; and optionally (b) recovering the polypeptide.

Removal or Reduction of Laccase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having laccase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ. ID NO: 27, SEQ ID NO: 29, SEQ ID NO: 31, SEQ ID NO: 33, or SEQ ID NO: 35 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and optionally (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially laccase activity-free product is of particular interest in the production of eukaryotic polypeptides, in particular fungal proteins such as enzymes. The laccase activity-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from laccase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the laccase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the polypeptides having laccase activity, or compositions thereof.

The present invention also relates to processes for degrading a cellulosic material, comprising: treating the cellulosic material with an enzyme composition in the presence of a polypeptide having laccase activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having laccase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having laccase activity of the present invention. In one aspect, the fermenting of the cellulosic material produces a fermentation product. In another aspect, the processes further comprise recovering the fermentation product from the fermentation.

The present invention also relates to processes for detoxifying a pre-treated lignocellulose-containing material comprising subjecting the pre-treated lignocellulose-containing material to a polypeptide having laccase activity of the present invention.

The present invention also relates to processes of producing a fermentation product, comprising: (a) pretreating a cellulosic material, (b) detoxifying the pretreated cellulosic material with a polypeptide having laccase activity of the present invention; (c) saccharifying the detoxified cellulosic material with an enzyme composition optionally in the presence of the polypeptide having laccase activity; (d) fermenting the saccharified cellulosic material with one or more (e.g., several) fermenting microorganisms to produce the fermentation product; and (e) recovering the fermentation product from the fermentation.

The present invention also relates to processes of producing a fermentation product, comprising: (a) pretreating a cellulosic material, (b) saccharifying the pretreated cellulosic material with an enzyme composition in the presence of a polypeptide having laccase activity of the present invention; (c) fermenting the saccharified cellulosic material with one or more (e.g., several) fermenting microorganisms to produce the fermentation product; and (d) recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faris de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Biomsource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli at al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan at al., 2006, *Biotechnol. Bioeng.* 94: 851-861; Kurabi et al., 2005, *Appl. Biochem. Biotechnol* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as a dilute add treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

When lignocellulose-containing material is pre-treated, degradation products that may inhibit enzymes and/or may be toxic to fermenting organisms are produced. These degradation products severely decrease both the hydrolysis and fermentation rate. In the processes for detoxifying a pre-treated lignocellulose-containing material of the present invention, the pre-treated lignocellulose-containing material is subjected to a polypeptide having laccase activity of the present invention. The fermentation time can be reduced as a result of improved performance of the fermenting organism during fermentation. In other words, detoxification in accordance with the present invention may result in a shorter "lignocellulose-containing material-to-fermentation product" process time. Furthermore, the need for a washing step after pre-treatment of the lignocellulose-containing material, to remove toxic compounds, and/or adaption of the fermentation organism to the medium/broth can be eliminated. Also, the dosing of the fermentation organism may be reduced.

The pre-treated lignocellulose degradation products may include lignin degradation products, cellulose degradation products, and/or hemicellulose degradation products. The pre-treated lignin degradation products may be phenolics in nature.

The hemicellulose degradation products may include furans from sugars (such as hexoses and/or pentoses), including xylose, mannose, galactose, rhamanose, and arabinose. Examples of hemicelluloses include xylan, galactoglucomannan, arabinogalactan, arabinoglucuronoxylan, glucuronoxylan, and derivatives and combinations thereof.

Examples of inhibitory compounds, i.e., pre-treated lignocellulose degradation products, include 4-OH benzyl alcohol, 4-OH benzaldehyde, 4-OH benzoic acid, trimethyl benzaldehyde, 2-furoic acid, coumaric acid, ferulic acid, phenol, guaiacol, veratrole, pyrogallollol, pyrogallol mono methyl ether, vanillyl alcohol, vanillin, isovanillin, vanillic acid, isovanillic acid, homovanillic acid, veratryl alcohol, veratraldehyde, veratric acid, 2-O-methyl gallic acid, syringyl alcohol, syringaldehyde, syringic acid, trimethyl gallic acid, homocatechol, ethyl vanillin, creosol, p-methyl anisol, anisaldehyde, anisic acid, furfural, hydroxymethylfurfural, 5-hydroxymethylfurfural, formic acid, acetic acid, levulinic acid, cinnamic acid, coniferyl aldehyde, isoeugenol, hydroquinone, eugenol or combinations thereof. Other inhibitory compounds can be found in, e.g., Luo et al., 2002, *Biomass and Bioenergy* 22: 125-138.

The detoxification process of the present invention may preferably be carried out at a pH that is suitable for the phenolic compound oxidizing enzymes and hydrolyzing enzyme(s) and/or fermenting organism if detoxification is carried out simultaneously with hydrolysis or simultaneously with hydrolysis and fermentation. In one embodiment the pH is between 2 and 7, preferably between 3 and 6, especially between 4 and 5. In a preferred embodiment the temperature during detoxification is a temperature suitable for a laccase of the present invention and hydrolyzing enzyme(s) and/or fermenting organism if detoxification is carried out a simultaneous with hydrolysis or simultaneously with hydrolysis and fermentation. In one embodiment the temperature during detoxification is between 25° C. and 70° C., preferably between 30° C. and 60° C. In cases where detoxification is carried out simultaneously with fermentation the temperature will depend on the fermenting organism. For ethanol fermentations with yeast the temperature would be between 26-38° C., such as between 26-34° C. or between 30-36° C., such as around 32° C.

Suitable pHs, temperatures, and other process conditions can easily be determined by one skilled in the art.

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having laccase activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can further comprise one or more (e.g., several) chemical mediator agents which enhance the activity of a polypeptide having laccase activity of the present invention. The chemical mediator may be a phenolic compound, for example, methyl syringate, and related compounds, as described in WO 95/01426 WO 96/12845, WO 96/12846, and WO2008/076323. The chemical mediator may also be an N-hydroxy compound, an N-oxime compound, or an N-oxide compound, for example, N-hydroxybenzotriazole, violuric acid, or N-hydroxyacetanilide. The chemical mediator may also be a phenoxazine/phenothiazine compound, for example, phenothiazine-10-propionate. The chemical mediator may further be 2,2'-azinobis-(3-ethylbenzothiazoline-6-sulfonic acid) (ABTS). Other chemical mediators are well known in the art. For example, the compounds disclosed in WO 95/01426 are known to enhance the activity of a laccase. In particular embodiments, the mediator may be acetosyringone, methyl syringate, syringamide, syringonitrile, ethyl syringate, propyl syringate, butyl syringate, hexyl syringate, or octyl syringate. Preferably, the mediator is 4-cyano-2,6-dimethoxyphenol, 4-carboxamido-2,6-dimethoxyphenol or an N-substituted derivative thereof such as, for example, 4-(N-methyl carboxamido)-2,6-dimethoxyphenol, 4-[N-(2-hydroxyethyl)carboxamido]-2,6-dimethoxyphenol, or 4-(N,N-dimethyl carboxamido)-2,6-dimethoxyphenol.

In one aspect, the enzyme compositions comprise or further comprise a mediator.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having laccase activity depend on several factors including, but not limited to, the mixture of cellulolytic and/or hemicellulolytic enzyme components, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having laccase activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having laccase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram-positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, *Caldicellulosiruptor*, *Acidothermus*, *Thermobifidia*, or *Oceanobacillus* polypeptide having enzyme activity, or a Gram-negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having enzyme activity.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus equi* subsp. *Zooepidemicus* polypeptide having enzyme activity.

In another aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Altemaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, *Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi of al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used as a component of the enzyme composition.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese or copper.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1, 2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid 6-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neuro-*

*spora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin at al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvaarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter* In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC— North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. MicrobioL* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^2$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999); which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another more preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Other Uses

The polypeptides of the present invention may be used in various industrial applications, in particular lignin modification (WO 1995/033836 and WO 1996/000290), paper strengthening, dye transfer inhibition in detergents, phenol polymerization, hair dyeing, bleaching of textiles (in particular bleaching of denim as described in WO 1996/12845 and WO 1996/12846), textile dyeing (WO 2001/044563, WO 2000/031333, WO 1997/023684, WO 1997/023685), fabric abrasion (WO 1997/025468), waste water treatment, and detoxification of pretreated cellulosic material (WO 2008/134259). Any detergent composition normally used for enzymes may be used, e.g., the detergent compositions disclosed in WO 95/01426.

Detergent Compositions

The polypeptides of the present invention having laccase activity may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the invention. The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, CAREZYME™ (Novozymes A/S), CLAZINASE™, and PURADAX HAT™ (Genencor International Inc.), and KAC-500(B)™ (Kao Corporation).

Proteases:

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™, SAVINASE™, PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases:

Suitable amylases (alpha and/or beta) include those of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™, and BAN™ (Novozymes A/S), and RAPIDASE™ and PURASTAR™ (Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono-, di-, and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1.% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention having laccase activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having laccase activity may also be incorporated in the detergent formulations disclosed in WO 97/07202, which is hereby incorporated by reference.

Signal Peptides

The present invention also relates to an isolated polynucleotide encoding a signal peptide comprising or consisting of amino acids 1 to 20 of SEQ ID NO: 2, amino acids 1 to 25 of SEQ ID NO: 4, amino acids 1 to 19 of SEQ ID NO: 6, amino acids 1 to 23 of SEQ ID NO: 8, amino acids 1 to 19 of SEQ ID NO: 10, amino acids 1 to 23 of SEQ ID NO: 12, amino acids 1 to 21 of SEQ ID NO: 14, amino acids 1 to 16 of SEQ ID NO: 16, amino acids 1 to 23 of SEQ ID NO: 18, amino acids 1 to 20 of SEQ ID NO: 20, amino acids 1 to 19 of SEQ ID NO: 22, amino acids 1 to 20 of SEQ ID NO: 24, amino acids 1 to 21 of SEQ ID NO: 26, amino acids 1 to 22 of SEQ ID NO: 28, amino acids 1 to 22 of SEQ ID NO: 30, amino acids 1 to 21 of SEQ ID NO: 32, amino acids 1 to 17 of SEQ ID NO: 34, or amino acids 1 to 21 of SEQ ID NO: 36. The polynucleotide may further comprise a gene encoding a protein, which is operably linked to the signal peptide. The protein is preferably foreign to the signal peptide. In one aspect, the polynucleotide encoding the signal peptide is nucleotides 1 to 60 of SEQ ID NO: 1. In another aspect, the polynucleotide encoding the signal peptide is nucleotides 1 to 75 of SEQ ID NO: 3. In another aspect, the polynucleotide encoding the signal peptide is nucleotides 1 to 57 of SEQ ID NO: 5. In another aspect, the polynucleotide encoding the signal peptide is nucleotides 1 to 69 of SEQ ID NO: 7. In another aspect, the polynucleotide encoding the signal peptide is nucleotides 1 to 57 of SEQ ID NO: 9. In another aspect, the polynucleotide encoding the signal peptide is nucleotides 1 to 69 of SEQ ID NO: 11. In another aspect, the polynucleotide encoding the signal peptide is nucleotides 1 to 63 of SEQ ID NO: 13. In another aspect, the polynucleotide encoding the signal peptide is nucleotides 1 to 48 of SEQ ID NO: 15. In another aspect, the polynucleotide encoding the signal peptide is nucleotides 1 to 69 of SEQ ID NO: 17. In another aspect, the polynucleotide encoding the signal peptide is nucleotides 1 to 60 of SEQ ID NO: 19. In another aspect, the polynucleotide encoding the signal peptide is nucleotides 1 to 57 of SEQ ID NO: 21. In another aspect, the polynucleotide encoding the signal peptide is nucleotides 1 to 60 of SEQ ID NO: 23. In another aspect, the polynucleotide encoding the signal peptide is nucleotides 1 to 63 of SEQ ID NO: 25. In another aspect, the polynucleotide encoding the signal peptide is nucleotides 1 to 66 of SEQ ID NO: 27. In another aspect, the polynucleotide encoding the signal peptide is nucleotides 1 to 66 of SEQ ID NO: 29. In another aspect, the polynucleotide encoding the signal peptide is nucleotides 1 to 63 of SEQ ID NO: 31. In another aspect, the polynucleotide encoding the signal peptide is nucleotides 1 to 51 of SEQ ID NO: 33. In another aspect, the polynucleotide encoding the signal peptide is nucleotides 1 to 63 of SEQ ID NO: 35.

The present invention also relates to nucleic acid constructs, expression vectors and recombinant host cells comprising such polynucleotides.

The present invention also relates to methods of producing a protein, comprising (a) cultivating a recombinant host cell comprising such a polynucleotide operably linked to a gene encoding the protein; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strain

The fungal strain NN044758 was isolated from a soil sample collected from China by dilution on PDA plates at 45° C. and then purified by transferring a single conidium onto a YG agar plate. The NN044758 strain was identified as *Malbranchea cinnamomea*, based on both morphological characteristics and ITS rDNA sequence.

The fungal strain NN046782 was isolated from a soil sample collected from China, by dilution on PDA plates at 45° C. and then purified by transferring a single conidium onto a YG agar plate. The NN046872 strain was identified as *Rhizomucor pusillus*, based on both morphological characteristics and ITS rDNA sequence.

The fungal strain NN051602 was isolated from a compost sample collected from China by dilution on PDA plates at 45° C. and then purified by transferring a single conidium onto a YG agar plate. The NN051602 strain was identified as *Penicillium emersonii*, based on both morphological characteristics and ITS rDNA sequence.

The fungal strain NN044936 was isolated from a soil sample collected from Yunnan Province, China, by dilution on PDA plates at 45° C. and then purified by transferring a single conidium onto a YG agar plate. The NN044936 strain was identified as *Thermoascus aurantiacus*, based on both morphological characteristics and ITS rDNA sequence.

*Corynascus thermophilus* CBS 174.70 (synonym *Myceliophthora fergusii*) was used as the source of the laccase coding sequences.

The fungal strain NN051380 was isolated from a soil sample collected from China, by dilution on PDA plates at 25° C. and then purified by transferring a single conidium onto a PDA plate. The NN051380 strain was identified as *Penicillium oxalicum*, based on both morphological characteristics and ITS rDNA sequence.

*Aspergillus oryzae* MT3568 strain was used for heterologous expression of the family GH7 genes encoding polypeptide having homology with polypeptides with cellobiohydrolase activity. *A. oryzae* MT3568 is an amdS (acetamidase) disrupted gene derivative of *Aspergillus oryzae* Jal_355 (WO 2002/40694) in which pyrG auxotrophy was restored by disrupting the *A. oryzae* acetamidase (amdS) gene with the pyrG gene Media PDA plates were composed of 39 grams of potato dextrose agar and deionized water to 1 liter.

YG agar plates were composed of 5 g of yeast extract, 10 g of glucose, 20 g of agar, and deionized water to 1 liter.

YPG medium was composed of 0.4% yeast extract, 0.1% $KH_2PO_4$, 0.05% $MgSO_4.7H_2O$, and 1.5% glucose in deionized water.

YPM medium was composed of 1% yeast extract, 2% peptone, and 2% maltose in deionized water.

Czapek's medium was composed of 30 g of sucrose, 3 g of $NaNO_3$, 0.5 g of $MgSO_4.7H_2O$, 0.01 g of $FeSO_4.7H_2O$, 1 g of $K_2HPO_4$, 0.5 g of KCl, and deionized water to 1 liter. The pH was adjusted to pH 4 with 1 M HCl.

FG4 medium was composed of 30 g of soybean meal, 15 g of maltose, 5 g of Bacto peptone, and deionized water to 1 liter.

Minimal medium plates were composed of 342 g of sucrose, 20 ml of salt solution, 20 g of agar, and deionized water to 1 liter. The salt solution was composed of 2.6% KCl, 2.6% $MgSO_4.7H_2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, and 400 ppm $ZnSO_4.7H_2O$.

Example 1: Genomic DNA Extraction

*Malbranchea cinnamomea* strain NN044758 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using Large-Scale Column Fungal DNAout (BAO-MAN BIOTECHNOLOGY, Shanghai, China) following the manufacturer's instruction.

*Rhizomucor pusillus* strain NN046782 was inoculated onto a PDA plate and incubated for 3 days at 45° C. in the darkness. Several mycelia-PDA plugs were inoculated into 500 ml shake flasks containing 100 ml of FG4 medium. The flasks were incubated for 3 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using DNEASY® Plant Maxi Kit (QIAGEN GmbH, Hilden, Germany) following the manufacturer's instructions.

*Penicillium emersonii* strain NN051602 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using a DNEASY® Plant Maxi Kit following the manufacturer's instructions.

*Thermoascus aurantiacus* strain NN044936 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using a DNEASY® Plant Maxi Kit following the manufacturer's instructions.

*Corynascus thermophilus* CBS 174.70 was inoculated onto a PDA plate and incubated for 3 days at 45° C. in the darkness. Several mycelia-PDA plugs were inoculated into 500 ml shake flasks containing 100 ml of YPG medium. The flasks were incubated for 4 days at 45° C. with shaking at 160 rpm. The mycelia were collected by filtration through MIRACLOTH® and frozen in liquid nitrogen. Frozen mycelia were ground, by a mortar and a pestle, to a fine powder, and genomic DNA was isolated using a DNEASY® Plant Maxi Kit.

*Penicillium oxalicum* strain NN051380 was inoculated onto a PDA plate and incubated for 5 days at 25° C. in the darkness. Several mycelia-PDA plugs were inoculated into 500 ml shake flasks containing 100 ml of Czapek's medium. The flasks were incubated for 3 days at 30° C. with shaking at 160 rpm. The mycelia were collected by filtration through MIRACLOTH® and frozen in liquid nitrogen. Frozen mycelia were ground, by a mortar and a pestle, to a fine powder, and the genomic DNA was isolated using a DNEASY® Plant Maxi Kit following the manufacturer's instructions.

Example 2: Genome Sequencing, Assembly and Annotation

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4): 511-515) was used for gene prediction. BlastaII version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The laccases were identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. The SignalP program was further used to predict signal peptides. Pepstats (Rice et al., 2000, *Trends Genet.* 16(6): 276-277) was used to estimate the isoelectric points and molecular weights of the deduced amino acid sequences.

Example 3: Cloning of *Malbranchea cinnamomea* Laccase Genes from Genomic DNA

Based on the DNA information (SEQ ID NOs: 1, 3, and 5) obtained from genome sequencing in Example 2, the oligonucleotide primers shown below were designed to amplify three laccase genes, LAC_ZY582296_514, Lac_ZY582371_13, and Lac_ZY582284_423, from the genomic DNA of *Malbranchea cinnamomea*. Primers were synthesized by Invitrogen, Beijing, China.

```
SEQID1 forward primer:
                                          (SEQ ID NO: 37)
ACACAACTGGGGATCCACCatgggtatctctgcgatgttttatctttg SEQID1 reverse primer:
                                          (SEQ ID NO: 38)
GTCACCCTCTAGATCTtatgggctgcggcaattacac SEQID3 forward primer:
                                          (SEQ ID NO: 39)
ACACAACTGGGGATCCACCatgtgtgactcgcgggttc SEQID3 reverse primer:
                                          (SEQ ID NO: 40)
GTCACCCTCTAGATCTcgatatccttggttcgctcagaga SEQID5 forward primer:
                                          (SEQ ID NO: 41)
ACACAACTGGGGATCCACCatgtatctgtccaaggaattcttctttgtc
```

-continued

SEQID5 reverse primer:
(SEQ ID NO: 42)
GTCACCCTCTAGATCTaagagattctccaggcgaaagctag Lowercase characters of the forward primers represent the coding regions of the genes and lowercase characters of the reverse primers represent the flanking region of the genes, while capitalized characters represent regions homologous to the insertion sites of pPFJO355 (WO 2011/005867).

For each gene, 20 picomoles of each forward and reverse primer pair were used in a PCR reaction composed of 2 µl of *Malbranchea cinnamomea* genomic DNA, 10 µl of 5×GC Buffer (Finnzymes Oy, Espoo, Finland), 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplifications were performed using a Peltier Thermal Cycler (MJ Research Inc., South San Francisco, Calif., USA) programmed for denaturing at 94° C. for 1 minute; 6 cycles of denaturing at 94° C. for 15 seconds, annealing at 68° C. for 30 seconds, with a 1° C. decrease per cycle, and elongation at 72° C. for 100 seconds; 23 cycles each at 94° C. for 15 seconds, 62° C. for 30 seconds, and 72° C. for 100 seconds; and a final extension at 72° C. for 5 minutes. The heat block then went to a 4° C. soak cycle.

The PCR products were isolated by 1.0% agarose gel electrophoresis using 90 mM Tris-borate and 1 mM EDTA (TBE) buffer where a single product band for each PCR reaction (2 kb for LAC_ZY582296_514, 2.3 kb for Lac_ZY582371_13, and 2.2 kb for Lac_ZY582284_423) was visualized under UV light. The PCR products were then purified from solution using an ILLUSTRA® GFX® PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

TABLE 1

Figure 2:
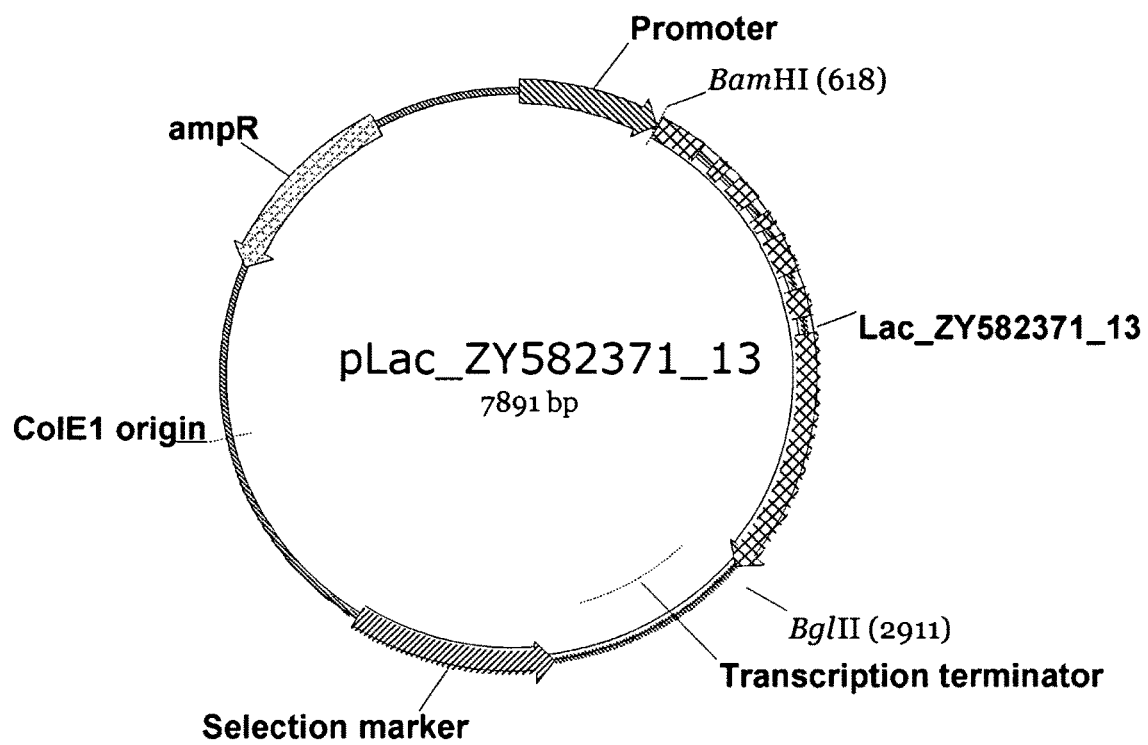
FIG. 2 shows a restriction map of pLac_ZY582371_13.
Figure 3:
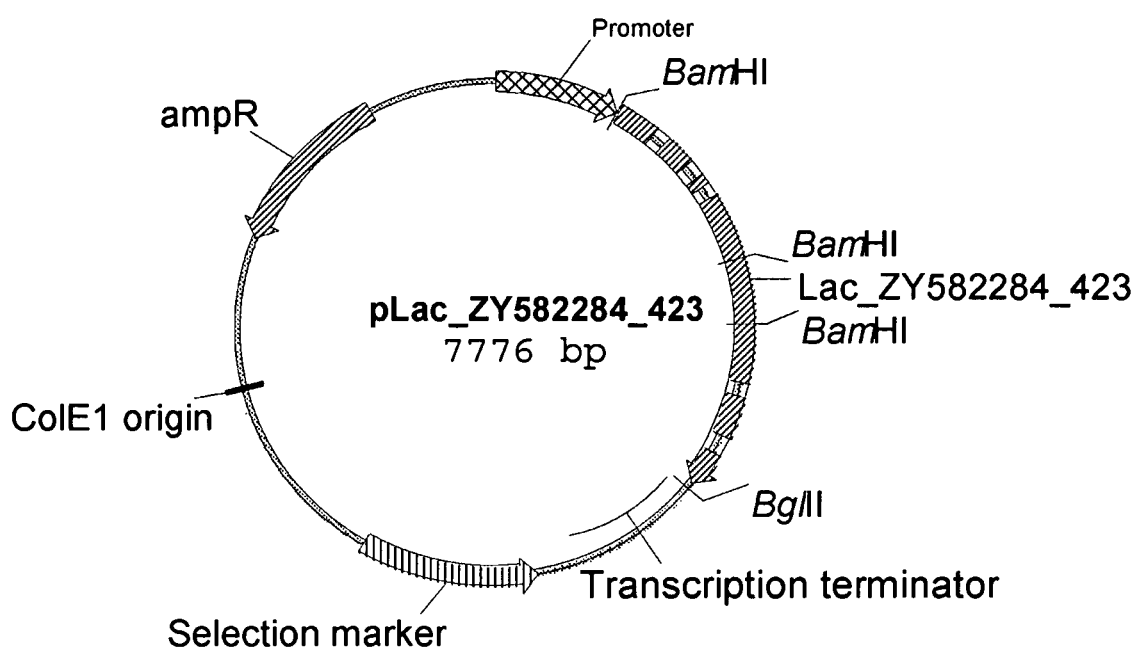
FIG. 3 shows a restriction map of pLac_ZY582284_423.

| Plasmids | | |
| --- | --- | --- |
| Gene name | Plasmid | DNA map |
| LAC_ZY582296_514 | pLAC_ZY582296_514 | FIG. 1 |
| Lac_ZY582371_13 | pLac_ZY582371_13 | FIG. 2 |
| Lac_ZY582284_423 | pLac_ZY582284_423 | FIG. 3 |

Each PCR product and the digested vector were ligated together using an IN-FUSION® CF Dry-down Cloning Kit (Clontech Laboratories, Inc., Mountain View, Calif., USA) resulting in the plasmids shown in Table 1: pLAC_ZY582296_514 (FIG. 1), pLac_ZY582371_13 (FIG. 2), and pLac_ZY582284_423 (FIG. 3) in which transcription of the *Malbranchea cinnamomea* laccase coding sequences was under the control of an *Aspergillus oryzae* alpha-amylase gene promoter. In brief, 30 ng of pPFJO355, digested with Bam HI and Bgl II, and 60 ng of each purified *Malbranchea cinnamomea* laccase PCR product were added to reaction vials and resuspended in a final volume of 10 µl by addition of deionized water. The reactions were incubated at 37° C. for 15 minutes and then 50° C. for 15 minutes. Three µl of the reactions were used to transform *E. coli* TOP10 competent cells (TIANGEN Biotech (Beijing) Co. Ltd., Beijing, China). *E. coli* transformants containing expression constructs were detected by colony PCR. Colony PCR is a method for quick screening of plasmid inserts directly from *E. coli* colonies. Briefly, in a premixed PCR solution aliquot in each PCR tube, including PCR buffer, $MgCl_2$, dNTPs, and primer pairs from which the PCR fragment was generated, a single colony was added by picking with a sterile tip and twirling the tip in the reaction solution. Normally 7-10 colonies were screened. After the PCR, reactions were analyzed by 1.0% agarose gel electrophoresis using TBE buffer. Plasmid DNA was prepared from colonies showing inserts with the expected sizes using a QIAPREP® Spin Miniprep Kit (QIAGEN GmbH, Hilden, Germany). The *Malbranchea cinnamomea* laccase coding sequences inserted in pLAC_ZY582296_514, pLac_ZY582284_423, and pLac_ZY582371_13 were confirmed by DNA sequencing using a 3730XL DNA Analyzer (Applied Biosystems Inc., Foster City, Calif., USA).

Example 4: Expression of a *Malbranchea cinnamomea* Laccase Coding Sequence in *Aspergillus oryzae*

*Aspergillus oryzae* HowB101 (WO 95/035385) protoplasts prepared according to the method of Christensen et al., 1988, Bio/Technology 6: 1419-1422, were transformed with 3 µg of pLAC_ZY582296_514. The transformation yielded about 50 transformants. Eight transformants from the transformation were isolated to individual Minimal medium plates.

Four transformants from the transformation were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM 2-(N-morpholino)ethanesulfonic acid (MES) (Invitrogen Corporation, Carlsbad, Calif., USA) according to the manufacturer's instructions. The resulting gel was stained with INSTANTBLUE® (Expedeon Ltd., Babraham Cambridge, UK). SDS-PAGE profiles of the cultures showed transformants of pLAC_ZY582296_514 had a major protein band at 65 kDa. One transformant was selected as an expression strain and designated *Aspergillus oryzae* O6PB8.

A slant of *Aspergillus oryzae* O6PB8 was washed with 10 ml of YPM and inoculated into four 2-liter flasks containing 400 ml of YPM medium. The cultures were harvested on day 3 and filtered using a 0.45 µm DURAPORE® Membrane (Millipore, Bedford, Mass., USA).

Example 5: Purification of Recombinant *Malbranchea cinnamomea* Laccase from *Aspergillus oryzae* O6PB8

A 1600 ml volume of the filtered broth of *Aspergillus oryzae* O6PB8 (Example 4) was precipitated with ammonium sulfate (80% saturation), re-dissolved in 50 ml of 20 mM Bis-Tris pH 6.0, dialyzed against the same buffer, and filtered through a 0.45 µm filter. The final volume was 60 ml. The solution was applied to a 40 ml Q SEPHAROSE® Fast Flow column (GE Healthcare, Buckinghamshire, UK) equilibrated with 20 mM Bis-Tris pH 6.0. The proteins were eluted with a linear 0-0.5 M NaCl gradient. Fractions were collected, pooled, and applied to a 40 ml SP SEPHAROSE® Fast Flow column (GE Healthcare, Buckinghamshire, UK) equilibrated in 20 mM sodium acetate pH 5.0. The proteins were eluted with a linear 0-0.5 M NaCl gradient and fractions eluted with 0.2-0.3 M NaCl were collected. The collected fractions were further purified on a 40 ml Phenyl SEPHAROSE® 6 Fast Flow column (GE Healthcare, Buckinghamshire, UK) with a linear 1.2-0 M $(NH_4)_2SO_4$ gradient. Fractions were evaluated by SDS-PAGE using a NUPAGE® NOVEX® 4-12% Bis-Tris Gel with 50 mM MES. Fractions containing a band at approximately 65 kDa were pooled. Then the pooled solution was concentrated by ultrafiltration.

Example 6: Cloning of *Rhizomucor pusillus* Laccase Genes from Genomic DNA

Based on the DNA information (SEQ ID NOs: 7, 9, and 11) obtained from genome sequencing in Example 2, the oligonucleotide primers shown below were designed to amplify three laccase genes, Lac_ZY654923_8142, Lac_ZY654858_3530, and Lac_ZY654866_4390, from the genomic DNA of *Rhizomucor pusillus* NN046782. Primers were synthesized by Invitrogen, Beijing, China.

```
SEQID7 forward primer:
                                      (SEQ ID NO: 43)
ACACAACTGGGGATCCACCatgtggtcactgtattgtatactgctacta SEQID7 reverse primer:
                                      (SEQ ID NO: 44)
GTCACCCTCTAGATCTtgtgtacggtgaggaggtcag SEQID9 forward primer:
                                      (SEQ ID NO: 45)
ACACAACTGGGGATCCACCatgaagacttactgcgcactcttg SEQID9 reverse primer:
                                      (SEQ ID NO: 46)
GTCACCCTCTAGATCTtcgaaatacacactactcctgttgcac SEQ ID11 forward primer
                                      (SEQ ID NO: 47)
ACACAACTGGGGATCCACCatgtcacatattttttcaactaatacactttc SEQ ID11 reverse primer:
                                      (SEQ ID NO: 48)
GTCACCCTCTAGATCTgtgggaagagggaatctttc
```

Lowercase characters of the forward primers represent the coding regions of the genes and lowercase characters of the reverse primers represent the flanking region of the genes, while capitalized characters represent regions homologous to the insertion sites of pPFJO355.

For each gene, 20 picomoles of each forward and reverse primer pair were used in a PCR reaction composed of 2 µl of *Rhizomucor pusNus* NN046782 genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase in a final volume of 50 µl. The amplifications were performed using a Peltier Thermal Cycler programmed for denaturing at 98° C. for 1 minute; 6 cycles of denaturing at 98° C. for 15 seconds, annealing at 65° C. for 30 seconds, with a 1° C. decrease per cycle, and elongation at 72° C. for 2.5 minutes; 23 cycles each at 94° C. for 15 seconds, 63° C. for 30 seconds, and 72° C. for 2.5 minutes; and a final extension at 72° C. for 5 minutes. The heat block then went to a 4° C. soak cycle.

The PCR products were isolated by 1.0% agarose gel electrophoresis using TBE buffer where a single product band for each PCR reaction of approximately 2 kb was visualized under UV light. The PCR products were then purified from solution using an ILLUSTRA® GFX® PCR DNA and Gel Band Purification Kit according to the manufacturers instructions.

Plasmid pPFJO355 was digested with Bam HI and Bgl isolated by 1.0% agarose gel electrophoresis using TBE buffer, and purified using an ILLUSTRA® GFX® PCR DNA and Gel Band Purification Kit according to the manufacturers instructions.

TABLE 2

Figure 4:
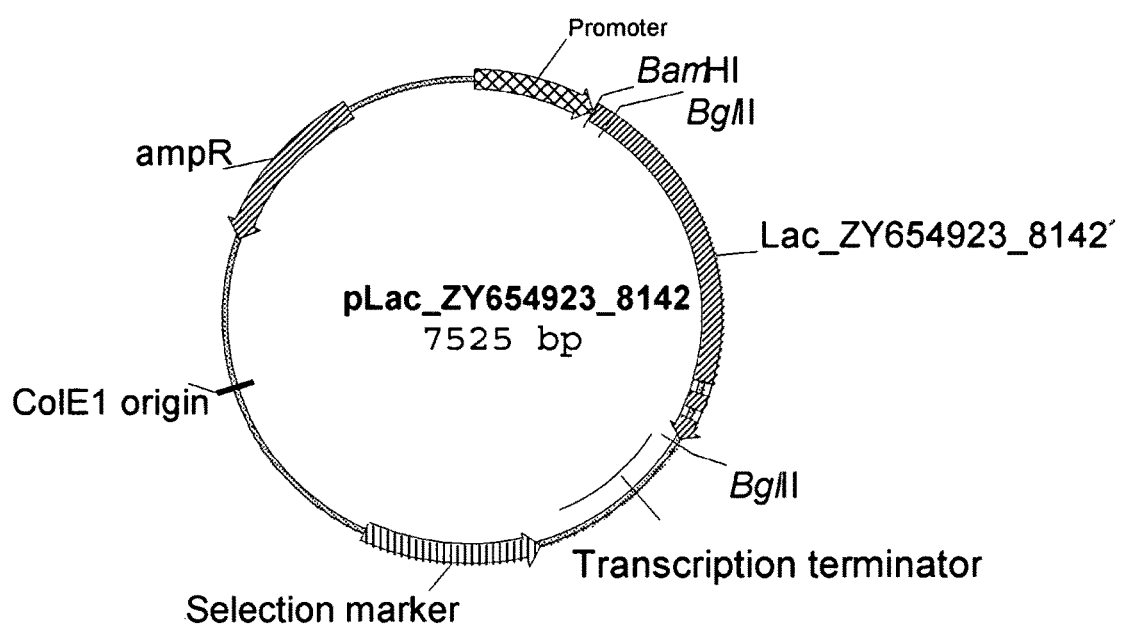
FIG. 4 shows a restriction map of pLac_ZY654923_8142.
Figure 5:
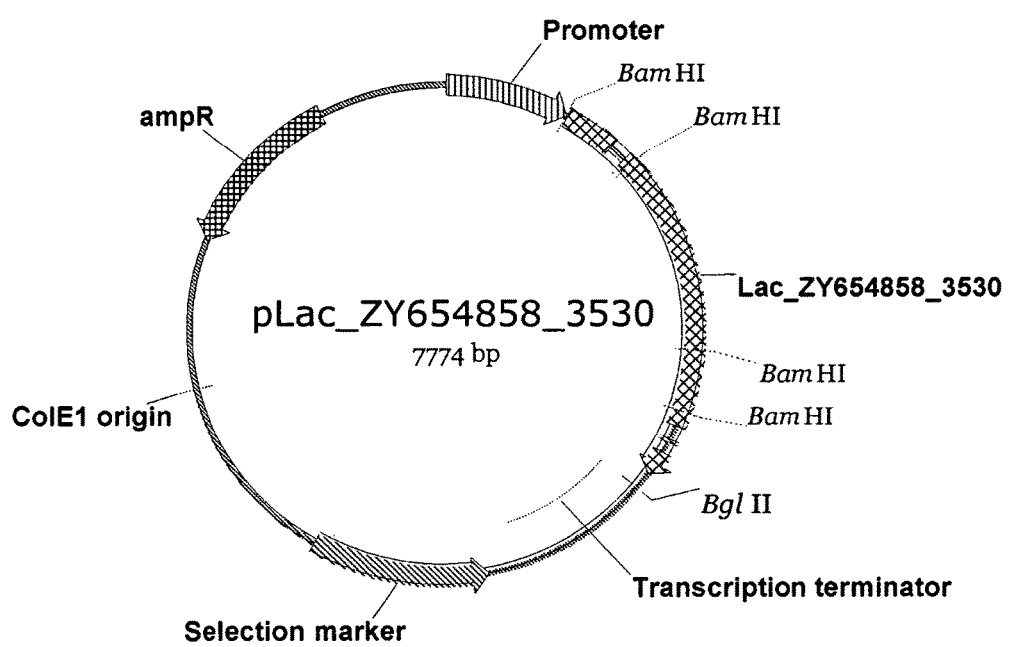
FIG. 5 shows a restriction map of pLac_ZY654858_3530.
Figure 6:
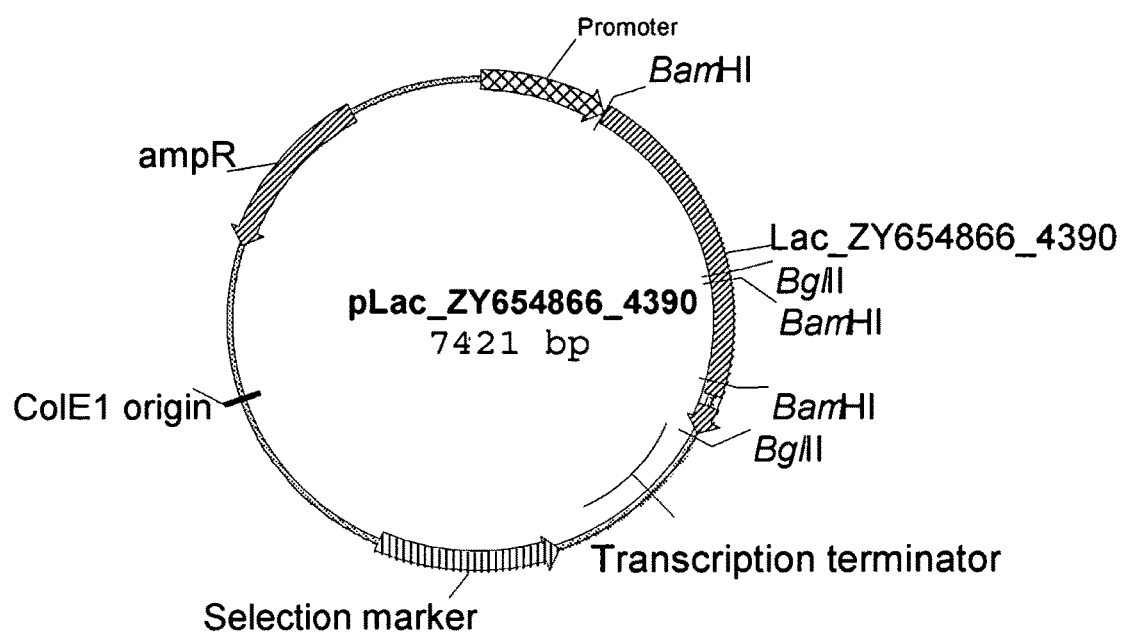
FIG. 6 shows a restriction map of pLac_ZY654866_4390.

| | Plasmids | |
|---|---|---|
| Gene name | Plasmid | DNA map |
| Lac_ZY654923_8142 | pLac_ZY654923_8142 | FIG. 4 |
| Lac_ZY654858_3530 | pLac_ZY654858_3530 | FIG. 5 |
| Lac_ZY654866_4390 | pLac_ZY654866_4390 | FIG. 6 |

Each PCR product and the digested vector were ligated together using an IN-FUSION® CF Dry-down Cloning Kit resulting in the plasmids shown in Table 2: pLac_ZY654923_8142 (FIG. 4), pLac_ZY654858_3530 (FIG. 5) and pLac_ZY654866_4390 (FIG. 6) in which transcription of the *Rhizomucor pusillus* laccase coding sequences was under the control of an *Aspergillus oryzae* alpha-amylase gene promoter. In brief, 30 ng of pPFJO355, digested with Bam HI and Bgl II, and 60 ng of each purified *Rhizomucor pusillus* laccase PCR product were added to reaction vials and resuspended in a final volume of 10 µl by addition of deionized water. The reactions were incubated at 37° C. for 15 minutes and then 50° C. for 15 minutes. Three µl of the reactions were used to transform *E. coli* TOP10 competent cells. *E. coli* transformants containing expression constructs were detected by colony PCR as described in Example 3. Plasmid DNA was prepared from colonies showing inserts with the expected sizes using a QIAPREP® Spin Miniprep Kit. The *Rhizomucor pusillus* laccase coding sequences inserted in pLac_ZY654923_8142, pLac_ZY654858_3530, and pLac_ZY654866_4390 were confirmed by DNA sequencing using a 3730XL DNA Analyzer.

Example 7: Cloning of *Penicillium emersonii* Laccase Genes from Genomic DNA

Based on the DNA information (SEQ ID NOs: 13, 15, and 17) obtained from genome sequencing in Example 2, the oligonucleotide primers shown below were designed to amplify three laccase genes, PE04230003607, PE04230006528, and PE04230006530, from the genomic DNA of *Penicillium emersonii* NN051602. Primers were synthesized by Invitrogen, Beijing, China.

```
SEQID13 forward primer:
                                      (SEQ ID NO: 49)
ACACAACTGGGGATCCACCatggcgccaaaagggtcc SEQID13 reverse primer:
                                      (SEQ ID NO: 50)
GTCACCCTCTAGATCTcagatgccagaagacggactagg SEQID15 forward primer:
                                      (SEQ ID NO: 51)
ACACAACTGGGGATCCACCatgaaactctggtttccagtcttttgc SEQID15 reverse primer:
                                      (SEQ ID NO: 52)
GTCACCCTCTAGATCTcgataatgcggcatgccag
```

-continued

SEQID17 forward primer:
(SEQ ID NO: 53)
ACACAACTGGGGATCCACCatggggatagcacttagattactatatacaa
catat SEQID17 reverse primer:
(SEQ ID NO: 54)
GTCACCCTCTAGATCTacgtaaatctatcgactatcgtcgtct Lowercase characters of the forward primers represent the coding regions of the genes and lowercase characters of the reverse primers represent the flanking region of the genes, while capitalized characters represent regions homologous to the insertion sites of pPFJO355.

For each gene, 20 picomoles of each forward and reverse primer pair were used in a PCR reaction composed of 2 μl of *Penicillium emersonii* NN051602 genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase in a final volume of 50 μl. The amplifications were performed using a Peltier Thermal Cycler programmed for denaturing at 98° C. for 1 minute; 8 cycles of denaturing at 98° C. for 15 seconds, annealing at 65° C. for 30 seconds, with a 1° C. decrease per cycle, and elongation at 72° C. for 3 minutes 15 seconds; 22 cycles each at 98° C. for 15 seconds, 58° C. for 15 seconds, and 72° C. for 3 minutes 15 seconds; and a final extension at 72° C. for 5 minutes. The heat block then went to a 4° C. soak cycle.

The PCR products were isolated by 1.0% agarose gel electrophoresis using TBE buffer where a single product band of 2.1 kb (PE04230003607), 1.7 kb (PE04230006528), or 1.9 kb (PE04230006530) was visualized under UV light. The PCR products were then purified from solution using an ILLUSTRA® GFX® PCR DNA and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

TABLE 3

Figure 7:
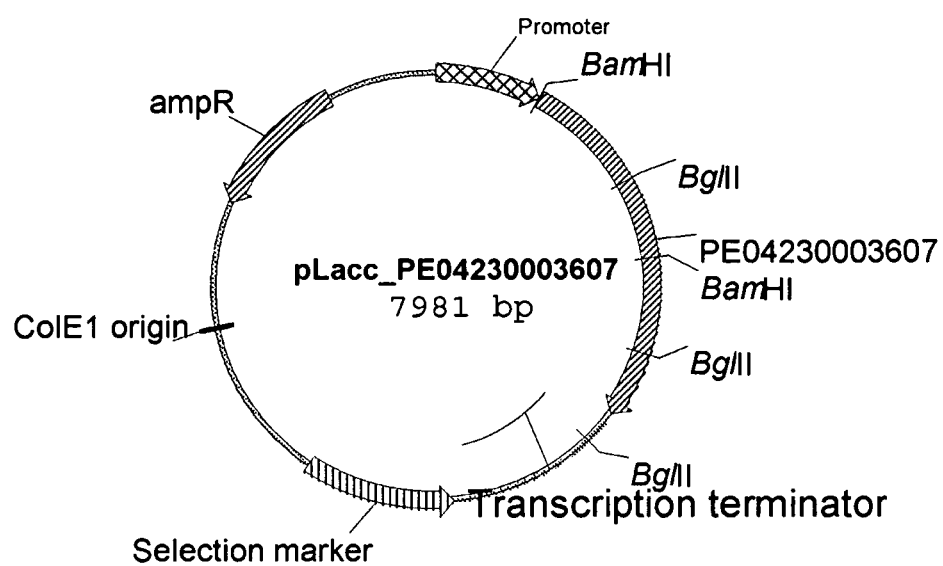
FIG. 7 shows a restriction map of pLacc_PE04230003607.
Figure 8:
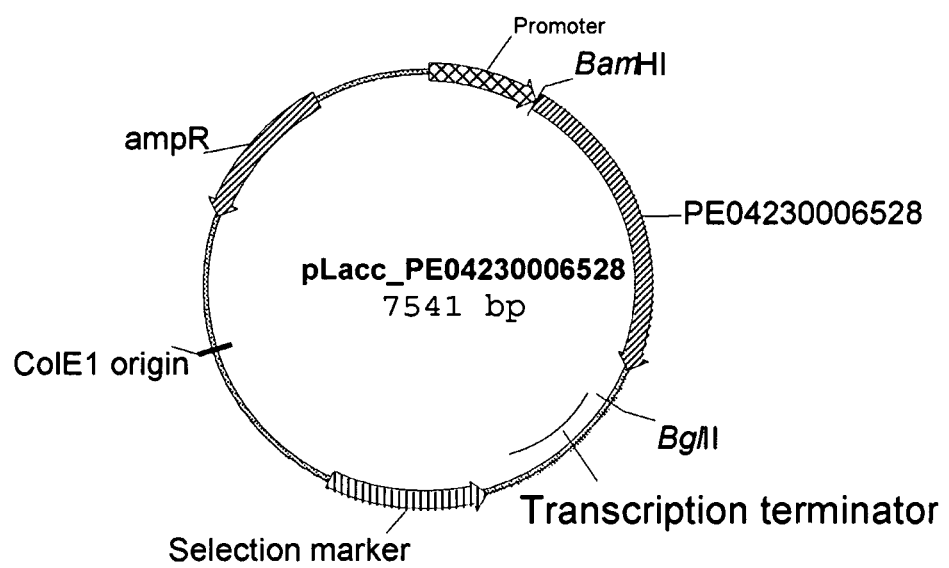
FIG. 8 shows a restriction map of pLacc_PE04230006528.
Figure 9:
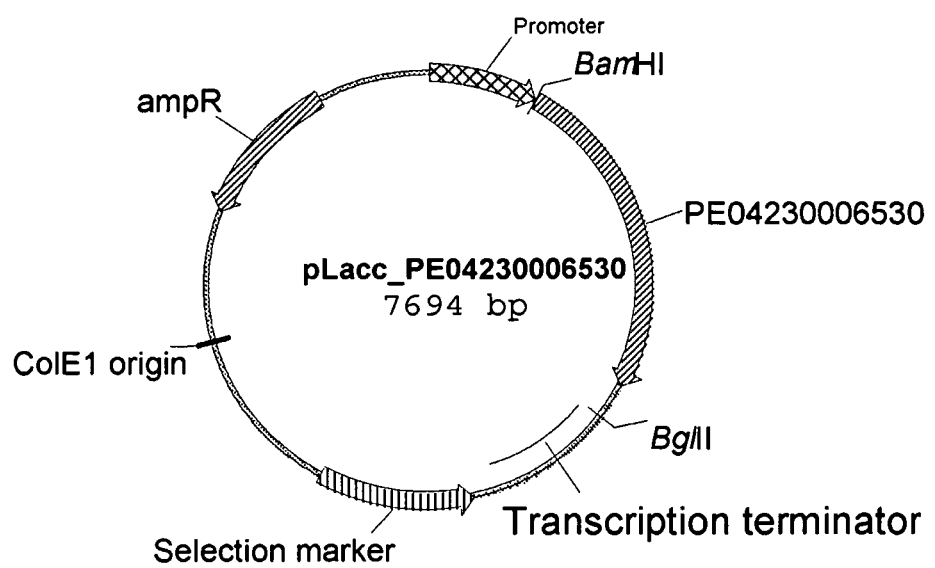
FIG. 9 shows a restriction map of pLacc_PE04230006530.

| Plasmids | | |
|---|---|---|
| Gene name | Plasmid | DNA map |
| PE04230003607 | pLacc_PE04230003607 | FIG. 7 |
| PE04230006528 | pLacc_PE04230006528 | FIG. 8 |
| PE04230006530 | pLacc_PE04230006530 | FIG. 9 |

Each PCR product and the digested vector were ligated together using an IN-FUSION® CF Dry-down Cloning Kit resulting in the plasmids shown in Table 3: pLacc_PE04230003607 (FIG. 7), pLacc_PE04230006528 (FIG. 8), and pLacc_PE04230006530 (FIG. 9) in which transcription of the *Penicillium emersonii* laccase coding sequences was under the control of an *Aspergillus oryzae* alpha-amylase gene promoter. In brief, 30 ng of pPFJO355, digested with Bam HI and Bgl II, and 60 ng of each purified *Penicillium emersonii* laccase PCR product were added to reaction vials and resuspended in a final volume of 10 μl by addition of deionized water. The reactions were incubated at 37° C. for 15 minutes and then 50° C. for 15 minutes. Three μl of the reactions were used to transform *E. coli* TOP10 competent cells. *E. coli* transformants containing expression constructs were detected by colony PCR as described in Example 3. Plasmid DNA was prepared from colonies showing inserts with the expected sizes using a QIAPREP® Spin Miniprep Kit. The *Penicillium emersonii* laccase coding sequences inserted in pLacc_PE04230003607, pLacc_PE04230006528, and pLacc_PE04230006530 were confirmed by DNA sequencing using a 3730XL DNA Analyzer.

Based on the DNA information (SEQ ID NO: 21) obtained from genome sequencing in Example 2, the oligonucleotide primers shown below were designed to amplify a laccase gene, lac_Pe2957, from the genomic DNA of *Penicillium emersonii* NN051602. Primers were synthesized by Invitrogen, Beijing, China.

SEQ ID 21 forward primer:
(SEQ ID NO: 55)
ACACAACTGGGGATCCACCatggcctcgctgatg

SEQ ID 21 reverse primer:
(SEQ ID NO: 56)
GTCACCCTCTAGATCTcgtggatcatggatcatgcttataag Lowercase characters of the forward primer represent the coding regions of the gens and lowercase characters of the reverse primer represent the flanking region of the gene, while capitalized characters represent regions homologous to the insertion sites of pCaHj505.

Twenty picomoles of each forward and reverse primer pair were used in a PCR reaction composed of 2 μl of *Penicillium emersonii* NN051602 genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase in a final volume of 50 μl. The amplifications were performed using a Peltier Thermal Cycler programmed for denaturing at 98° C. for 1 minute; 10 cycles of denaturing at 98° C. for 30 seconds, annealing at 65° C. for 30 seconds, with a 1° C. decrease per cycle, and elongation at 72° C. for 2 minutes; 24 cycles each at 98° C. for 30 seconds, 55° C. for 30 seconds, and 72° C. for 2 minutes; and a final extension at 72° C. for 5 minutes. The heat block then went to a 4° C. soak cycle.

The PCR products were isolated by 1.0% agarose gel electrophoresis using TBE buffer where a single product band of 2 kb (lac_Pe2957) was visualized under UV light. The PCR products were then purified from solution using an ILLUSTRA™ GFX™ PCR and Gel Band Purification Kit according to the manufacturer's instructions.

Plasmid pCaHj505 was digested with Bam HI and Bgl II, isolated by 1.0% agarose gel electrophoresis using TBE buffer, and purified using an ILLUSTRA™ GFX™ PCR and Gel Band Purification Kit according to the manufacturer's instructions.

TABLE 4

Figure 10:
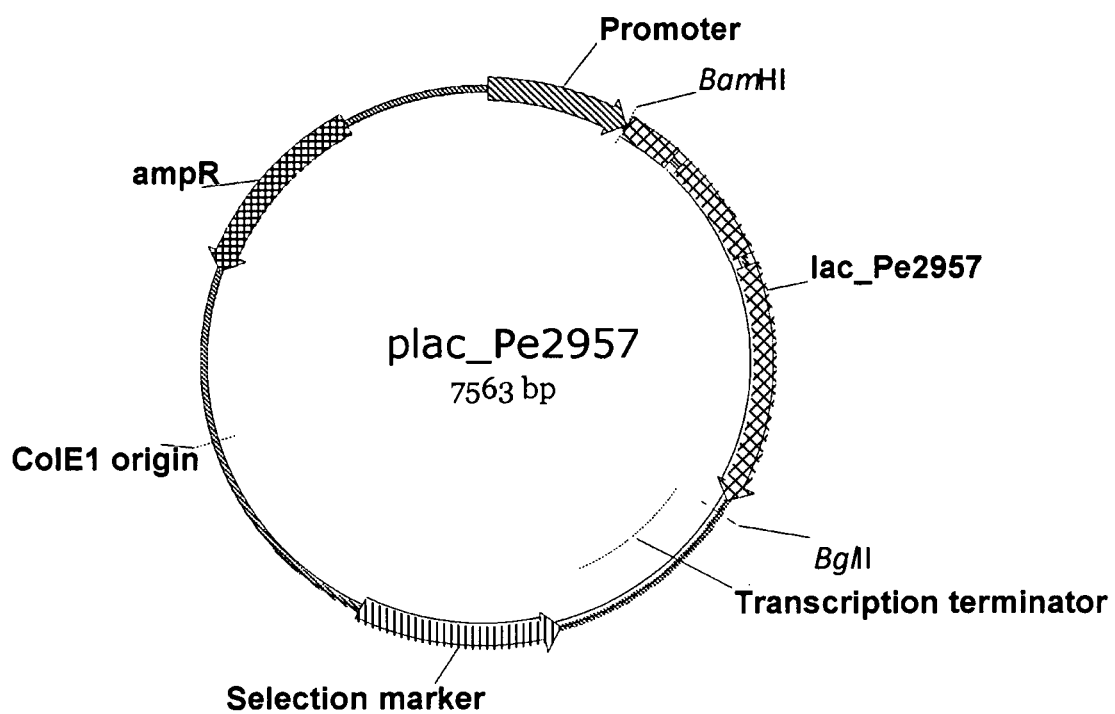
FIG. 10 shows a restriction map of p505-lac_Pe2957.

| Plasmid | | |
|---|---|---|
| Gene name | Plasmid | DNA map |
| lac_Pe2957 | p505-lac_Pe2957 | FIG. 10 |

The PCR product and the digested vector were ligated together using an IN-FUSIONS CF Dry-down Cloning Kit resulting in the plasmids shown in Table 4: p505-lac_Pe2957 (FIG. 10) in which transcription of the *Penicillium emersonii* laccase coding sequences was under the control of an *Aspergillus oryzae* alpha-amylase gene promoter. In brief, 30 ng of pCaHj505, digested with Bam HI and Bgl II, and 60 ng of each purified *Penicillium emersonii* laccase PCR product were added to reaction vials and resuspended in a final volume of 10 µl by addition of deionized water. The reactions were incubated at 37° C. for 15 minutes and then 50° C. for 15 minutes. Three µl of the reactions were used to transform *E. coli* TOP10 competent cells. *E. coli* transformants containing expression constructs were detected by colony PCR as described in Example 3. Plasmid DNA was prepared from colonies showing inserts with the expected sizes using a QIAprep® Spin Miniprep Kit. The *Penicillium emersonii* laccase coding sequence inserted in p505-lac_Pe2957 was confirmed by DNA sequencing using a 3730XL DNA Analyzer.

Example 8: Expression of *Penicillium emersonii* Laccase Coding Sequences in *Aspergillus oryzae*

*Aspergillus oryzae* HowB101 (WO 95/035385) protoplasts prepared according to the method of Christensen et al., 1988, supra, were transformed with 3 µg of pLacc_PE04230003607, pLacc_PE04230006528, or pLacc_PE04230006530. The transformations each yielded about 50 transformants. Eight transformants from each transformation were isolated to individual Minimal medium plates.

Four transformants from each transformation were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM ME) according to the manufacturers instructions. The resulting gel was stained with INSTANTBLUE®. SDS-PAGE profiles of the cultures showed transformants of pLacc_PE04230003607 had a major protein band at 90 kDa, transformants of pLacc_PE04230006528 had a major protein band at 96 kDa, and transformants of pLacc_PE04230006530 had a major protein band at 90 kDa. One transformant was selected from each transformation as an expression strain and designated *Aspergillus oryzae* O7MEX for pLacc_PE04230003607, *Aspergillus oryzae* O7MEY for pLacc_PE04230006528, and *Aspergillus oryzae* O7MEZ for pLacc_PE04230006530.

Slants of *Aspergillus oryzae* O7MEX, *Aspergillus oryzae* O7MEY, and *Aspergillus oryzae* O7MEZ were washed with 10 ml of YPM and each separately inoculated into 2-liter flasks each containing 400 ml of YPM medium. The cultures were harvested on day 3 and filtered using a 0.45 µm DURAPORE® Membrane.

*Aspergillus oryzae* MT3568 protoplasts prepared according to the method of Christensen et al., 1988, supra, were transformed with 3 µg of p505-lac_Pe2957. The transformation yielded about 50 transformants. Eight transformants were isolated to individual Minimal medium plates.

Four transformants were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES according to the manufacturer's instructions. The resulting gel was stained with INSTANTBLUE®. SDS-PAGE profiles of the cultures showed transformants of p505-lac_Pe2957 had a major protein band at 90 kDa. One transformant was selected as an expression strain and designated *Aspergillus oryzae* O229DJ for p505-lac_Pe2957.

Example 9: Cloning of *Thermoascus aurantiacus* Laccase Genes from Genomic DNA Based on the DNA information (SEQ ID NOs: 23 and 25) obtained from genome sequencing in Example 2, the oligonucleotide primers shown below were designed to amplify three laccase genes, lac_Ta7541 and lac_Ta4809, from the genomic DNA of *Thermoascus aurantiacus* NN044936. Primers were synthesized by Invitrogen, Beijing, China.

SEQID23 forward primer:
(SEQ ID NO: 57)
ACACAACTGGGGATCCACCatgtctttcgttaactcactattccttctc SEQID23 reverse primer:
(SEQ ID NO: 58)
GTCACCCTCTAGATCTcagtgactgcaacttcaaacaagc SEQID25 forward primer:
(SEQ ID NO: 59)
ACACAACTGGGGATCCACCatggcaccactaaggtcgcttc SEQID25 reverse primer:
(SEQ ID NO: 60)
GTCACCCTCTAGATCTacagaaaataccgctacaggaacaagc Lowercase characters of the forward primers represent the coding regions of the genes and lowercase characters of the reverse primers represent the flanking region of the genes, while capitalized characters represent regions homologous to the insertion sites of pCaHj505.

For each gene, 20 picomoles of each forward and reverse primer pair were used in a PCR reaction composed of 2 µl of *Thermoascus aurantiacus* NN044936 genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase in a final volume of 50 µl. The amplifications were performed using a Peltier Thermal Cycler programmed for denaturing at 98° C. for 1 minute; 10 cycles of denaturing at 98° C. for 30 seconds, annealing at 65° C. for 30 seconds, with a 1° C. decrease per cycle, and elongation at 72° C. for 2 minutes; 24 cycles each at 98° C. for 30 seconds, 55° C. for 30 seconds, and 72° C. for 2 minutes; and a final extension at 72° C. for 5 minutes. The heat block then went to a 4° C. soak cycle.

The PCR products were isolated by 1.0% agarose gel electrophoresis using TBE buffer where a single product band of 2.2 kb (lac_Ta7541), or 2.1 kb (lac_Ta4809) was visualized under UV light. The PCR products were then purified from solution using an ILLUSTRA™ GFX™ PCR and Gel Band Purification Kit according to the manufacturer's instructions.

Plasmid pCaHj505 was digested with Bam HI and Bgl II, isolated by 1.0% agarose gel electrophoresis using TBE buffer, and purified using an ILLUSTRA™ GFX™ PCR and Gel Band Purification Kit according to the manufacturer's instructions.

TABLE 5

Figure 11:
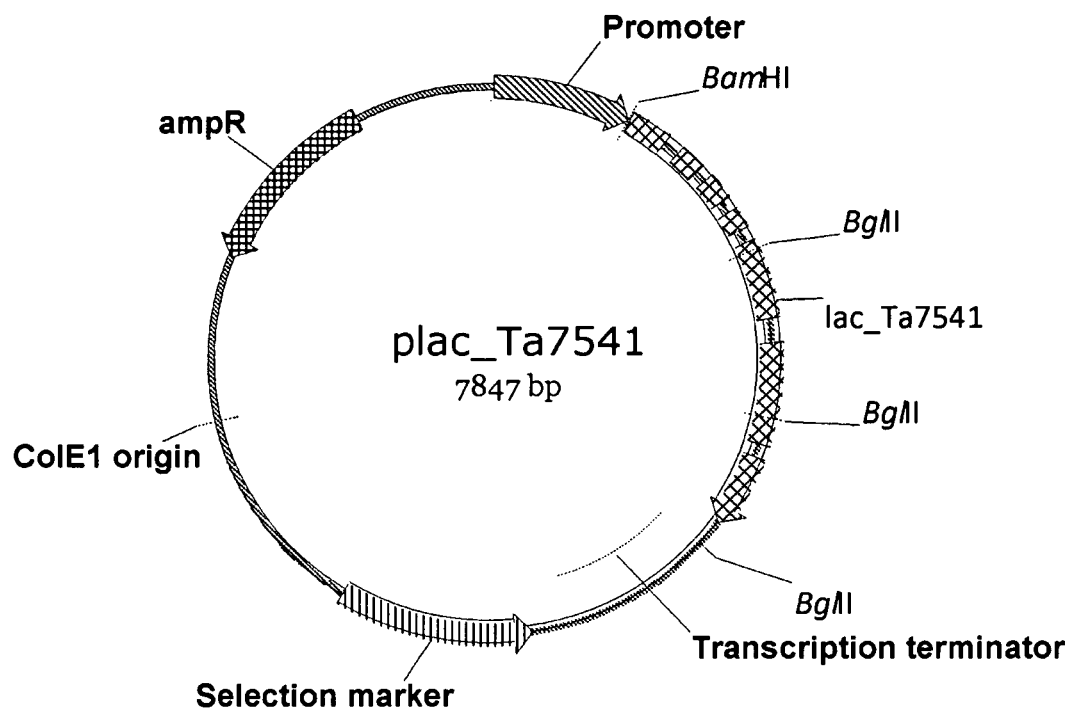
FIG. 11 shows a restriction map of p505-lac_Ta7541.
Figure 12:
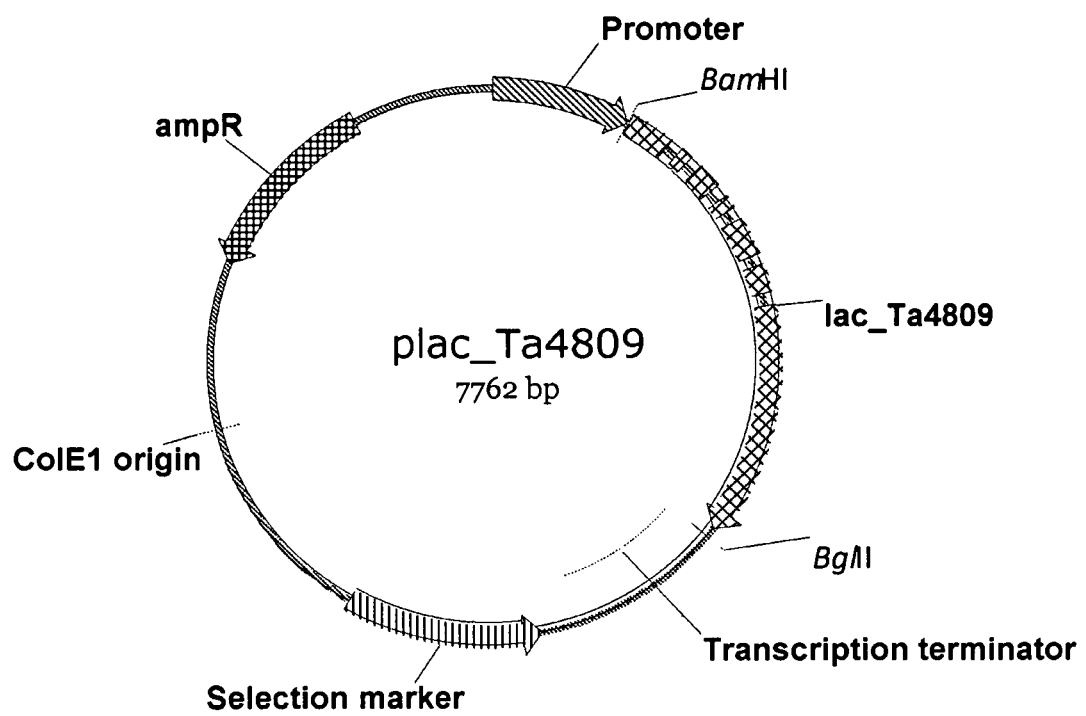
FIG. 12 shows a restriction map of p505-lac_Ta4809.

| Plasmids | | |
|---|---|---|
| Gene name | Plasmid | DNA map |
| lac_Ta7541 | p505-lac_Ta7541 | FIG. 11 |
| lac_Ta4809 | p505-lac_Ta4809 | FIG. 12 |

Each PCR product and the digested vector were ligated together using an IN-FUSION® CF Dry-down Cloning Kit resulting in the plasmids shown in Table 5: p505-lac_Ta7541 (FIG. 11) and p505-lac_Ta4809 (FIG. 12) in which transcription of the *Thermoascus aurantiacus* laccase coding sequences was under the control of an *Aspergillus oryzae* alpha-amylase gene promoter. In brief, 30 ng of pCaHj505, digested with Bam HI and Bgl II, and 60 ng of each purified Thermoascus aurantiacus laccase PCR product were added to reaction vials and resuspended in a final volume of 10 μl by addition of deionized water. The reactions were incubated at 37° C. for 15 minutes and then 50° C. for 15 minutes. Three μl of the reactions were used to transform *E. coli* TOP10 competent cells. *E. coli* transformants containing expression constructs were detected by colony PCR as described in Example 3. Plasmid DNA was prepared from colonies showing inserts with the expected sizes using a QIAprep® Spin Miniprep Kit. The *Thermoascus aurantiacus* laccase coding sequences inserted in p505-lac_Ta7541, and p505-lac_Ta4809 were confirmed by DNA sequencing using a 3730XL DNA Analyzer.

Example 10: Expression of *Thermoascus aurantiacus* Laccase Coding Sequences in *Aspergillus oryzae*

*Aspergillus oryzae* MT3568 protoplasts prepared according to the method of Christensen et al., 1988, supra, were transformed with 3 μg of p505-lac_Ta7541, and p505-lac_Ta4809. The transformations each yielded about 50 transformants. Eight transformants from each transformation were isolated to individual Minimal medium plates.

Four transformants from each transformation were inoculated separately into 3 ml of YPM medium in a 24-well plate and incubated at 30° C. with agitation at 150 rpm. After 3 days incubation, 20 μl of supernatant from each culture were analyzed by SDS-PAGE using a NUPAGE® NOVEX® 4-12% Bis-Tris Gel with 50 mM MES according to the manufacturer's instructions. The resulting gel was stained with INSTANTBLUE®. SDS-PAGE profiles of the cultures showed transformants of p505-lac_Ta7541 and p505-lac_Ta4809 each had a major protein band at 90 kDa. One transformant was selected from each transformation as an expression strain and designated *Aspergillus oryzae* O229DM for p505-lac_Ta7541 and *Aspergillus oryzae* O229DK for p505-lac_Ta4809.

Example 11: Cloning of *Corynascus thermophilus* Laccase Genes from Genomic DNA

Based on the DNA information (SEQ ID NOs: 27, 29, and 31) obtained from genome sequencing in Example 2, the oligonucleotide primers shown below were designed to amplify three laccase genes, lac_Mf7999, lac_Mf1582, and lac_Mf0715, from the genomic DNA of *Corynascus thermophilus* strain NN000308. Primers were synthesized by Invitrogen, Beijing, China.

```
SEQID27 forward primer:
                              (SEQ ID NO: 61)
ACACAACTGGGGATCCACCatgtttcgaccggcc SEQID27 reverse primer:
                              (SEQ ID NO: 62)
GTCACCCTCTAGATCTgtctcaaacggtctcaaagggaag SEQID29 forward primer:
                              (SEQ ID NO: 63)
ACACAACTGGGGATCCACCatggctgcaaggtgtcttgg SEQID29 reverse primer:
                              (SEQ ID NO: 64)
GTCACCCTCTAGATCTggaataccgcgattaaacggtg SEQID31 forward primer:
                              (SEQ ID NO: 65)
ACACAACTGGGGATCCACCatgaaaccgttcatcagcg SEQID31 reverse primer:
                              (SEQ ID NO: 66)
GTCACCCTCTAGATCTcttccccatcttctgtcagtttg
```

Lowercase characters of the forward primers represent the coding regions of the genes and lowercase characters of the reverse primers represent the flanking region of the genes, while capitalized characters represent regions homologous to the insertion sites of pCaHj505 (WO 1998/011203). The expression vector pCaHj505 contains the TAKA-amylase promoter derived from *Aspergillus oryzae* and the *Aspergillus niger* glucoamylase transcription terminator elements. Furthermore pCaHj505 had pUC19 derived sequences for selection and propagation in *E. coli*, and an amdS gene, which encoded an acetoamidase gene derived from *Aspergillus nidulans* for selection of an amdS+ *Aspergillus* transformant.

For each gene, 20 picomoles of each forward and reverse primer pair were used in a PCR reaction composed of 2 μl of *Corynascus thermophilus* strain NN000308 genomic DNA, 10 μl of 5×GC Buffer, 1.5 μl of DMSO, 2.5 mM each of dATP, dTTP, dGTP, and dCTP, and 0.6 unit of PHUSION™ High-Fidelity DNA Polymerase in a final volume of 50 μl. The amplifications were performed using a Peltier Thermal Cycler programmed for denaturing at 98° C. for 1 minute; 10 cycles of denaturing at 98° C. for 30 seconds, annealing at 65° C. for 30 seconds, with a 1° C. decrease per cycle, and elongation at 72° C. for 2 minutes; 24 cycles each at 98° C. for 30 seconds, 55° C. for 30 seconds, and 72° C. for 2 minutes; and a final extension at 72° C. for 5 minutes. The heat block then went to a 4° C. soak cycle.

The PCR products were isolated by 1.0% agarose gel electrophoresis using TBE buffer where a single product band of 2 kb (lac_Mf7999), 2 kb (lac_Mf1582), or 2.4 kb (lac_Mf0715) was visualized under UV light. The PCR products were then purified from solution using an ILLUSTRA™ GFX™ PCR and Gel Band Purification Kit according to the manufacturers instructions.

Plasmid pCaHj505 was digested with Bam HI and Bgl II, isolated by 1.0% agarose gel electrophoresis using TBE buffer, and purified using an ILLUSTRA™ GFX™ PCR and Gel Band Purification Kit according to the manufacturers instructions.

TABLE 6

Figure 13:
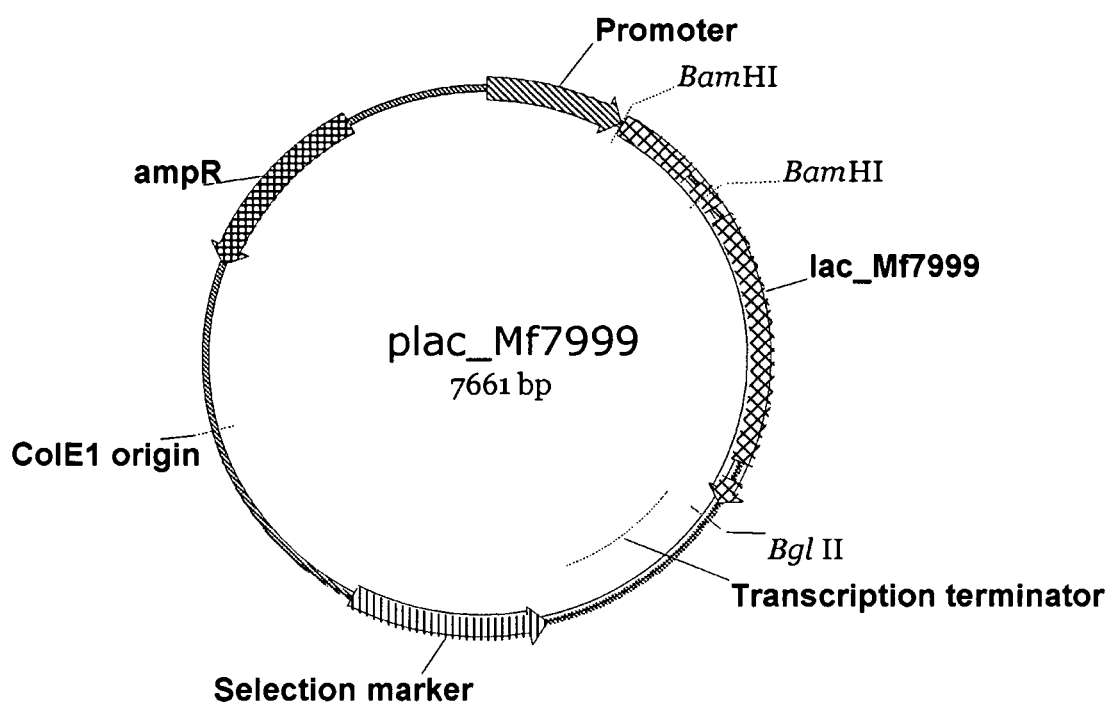
FIG. 13 shows a restriction map of p505-lac_Mf7999.
Figure 14:
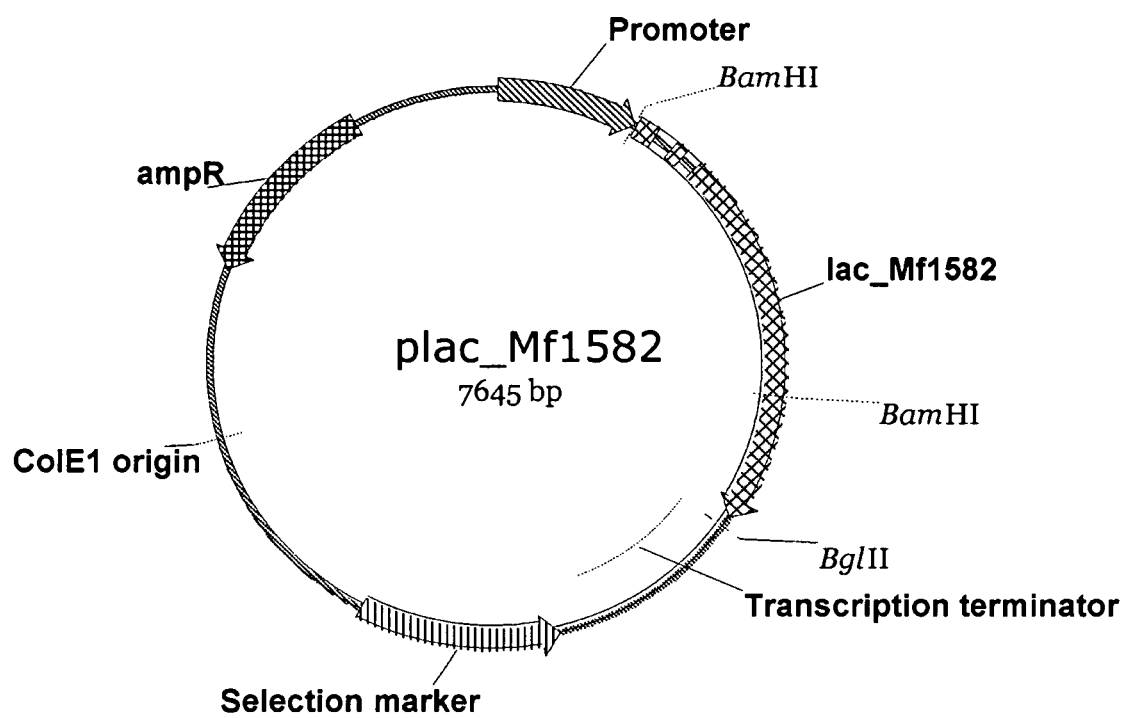
FIG. 14 shows a restriction map of p505-lac_Mf1582.
Figure 15:
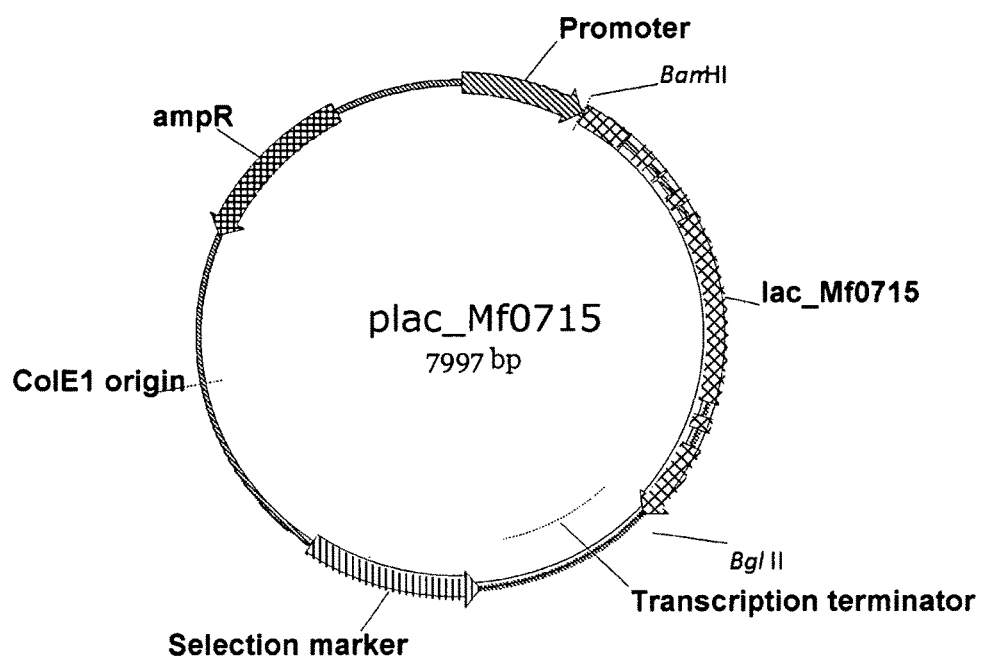
FIG. 15 shows a restriction map of p505-lac_Mf0715.

| Plasmids | | |
| --- | --- | --- |
| Gene name | Plasmid | DNA map |
| lac_Mf7999 | p505-lac_Mf7999 | FIG. 13 |
| lac_Mf1582 | p505-lac_Mf1582 | FIG. 14 |
| lac_Mf0715 | p505-lac_Mf0715 | FIG. 15 |

Each PCR product and the digested vector were ligated together using an IN-FUSION® CF Dry-down Cloning Kit resulting in the plasmids shown in Table 6: p505-lac_Mf7999 (FIG. 13), p505-lac_Mf1582 (FIG. 14), and p505-lac_Mf0715 (FIG. 15) in which transcription of the *Corynascus thermophilus* laccase coding sequences was under the control of an *Aspergillus oryzae* alpha-amylase gene promoter. In brief, 30 ng of pCaHj505, digested with Bam HI and Bgl II, and 60 ng of each purified *Corynascus thermophilus* laccase PCR product were added to reaction vials and resuspended in a final volume of 10 μl by addition of deionized water. The reactions were incubated at 37° C. for 15 minutes and then 50° C. for 15 minutes. Three μl of the reactions were used to transform *E. coli* TOP10 competent cells. *E. coli* transformants containing expression constructs were detected by colony PCR as described in Example 3. Plasmid DNA was prepared from colonies showing inserts with the expected sizes using a QIAPREP® Spin Miniprep Kit. The *Corynascus thermophiles* laccase coding sequences inserted in p505-lac_Mf7999, p505-lac_Mf1582, and p505-lac_Mf0715 were confirmed by DNA sequencing using a 3730XL DNA Analyzer.

Example 12: Expression of *Corynascus thermophilus* Laccase Coding Sequences in *Aspergillus oryzae*

*Aspergillus oryzae* MT3568 protoplasts prepared according to the method of Christensen et al., 1988, supra, were transformed with 3 µg of p505-lac_Mf7999, p505-lac_Mf1582, and p505-lac_Mf0715. The transformations each yielded about 50 transformants. Eight transformants from each transformation were isolated to individual Minimal medium plates.

Four transformants from each transformation were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES according to the manufacturer's instructions. The resulting gel was stained with INSTANTBLUE®. SDS-PAGE profiles of the cultures showed transformants of p505-lac_Mf1582 had a major protein band at 80 kDa, and transformants of p505-lac_Mf0715 had a major protein band at 75 kDa. One transformant was selected from each transformation as an expression strain and designated *Aspergillus oryzae* O229DG for p505-lac_Mf1582 and *Aspergillus oryzae* O229DF for p505-lac_Mf0715.

Example 13: Cloning of *Penicillium oxalicum* Laccase Genes from Genomic DNA

Based on the DNA information (SEQ ID NOs: 33 and 35) obtained from genome sequencing in Example 2, the oligonucleotide primers shown below were designed to amplify three laccase genes, lac_Po1328 and lac_Po6721, and lac_Po3087, from the genomic DNA of *Penicillium oxalicum* strain NN051380. Primers were synthesized by Invitrogen, Beijing, China.

```
SEQID33 forward primer:
                                        (SEQ ID NO: 67)
ACACAACTGGGGATCCACCatgaacgttttgatttacctcctttatg SEQID33 reverse primer:
                                        (SEQ ID NO: 68)
GTCACCCTCTAGATCTgagtttcacagaaaaactagaaacttcaagg SEQID35 forward primer:
                                        (SEQ ID NO: 69)
ACACAACTGGGGATCCACCatggctccattgcgcactc SEQID35 reverse primer:
                                        (SEQ ID NO: 70)
GTCACCCTCTAGATCTagccatccgactcgacgatag
```

Lowercase characters of the forward primers represent the coding regions of the genes and lowercase characters of the reverse primers represent the flanking region of the genes, while capitalized characters represent regions homologous to the insertion sites of pCaHj505.

For each gene, 20 picomoles of each forward and reverse primer pair were used in a PCR reaction composed of 2 µl of *Penicillium oxalicum*. NN051380 genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase in a final volume of 50 µl. The amplifications were performed using a Peltier Thermal Cycler programmed for denaturing at 98° C. for 1 minute; 10 cycles of denaturing at 98° C. for 30 seconds, annealing at 65° C. for 30 seconds, with a 1° C. decrease per cycle, and elongation at 72° C. for 2 minutes; 24 cycles each at 98° C. for 30 seconds, 55° C. for 30 seconds, and 72° C. for 2 minutes; and a final extension at 72° C. for 5 minutes. The heat block then went to a 4° C. soak cycle.

The PCR products were isolated by 1.0% agarose gel electrophoresis using TBE buffer where a single product band of 2 kb (lac_Po1328) or 2.1 kb (lac_Po6721) was visualized under UV light. The PCR products were then purified from solution using an ILLUSTRA™ GFX™ PCR and Gel Band Purification Kit according to the manufacturer's instructions.

Plasmid pCaHj505 was digested with Bam HI and Bgl II, isolated by 1.0% agarose gel electrophoresis using TBE buffer, and purified using an ILLUSTRA™ GFX™ PCR and Gel Band Purification Kit according to the manufacturer's instructions.

TABLE 7

Figure 16:
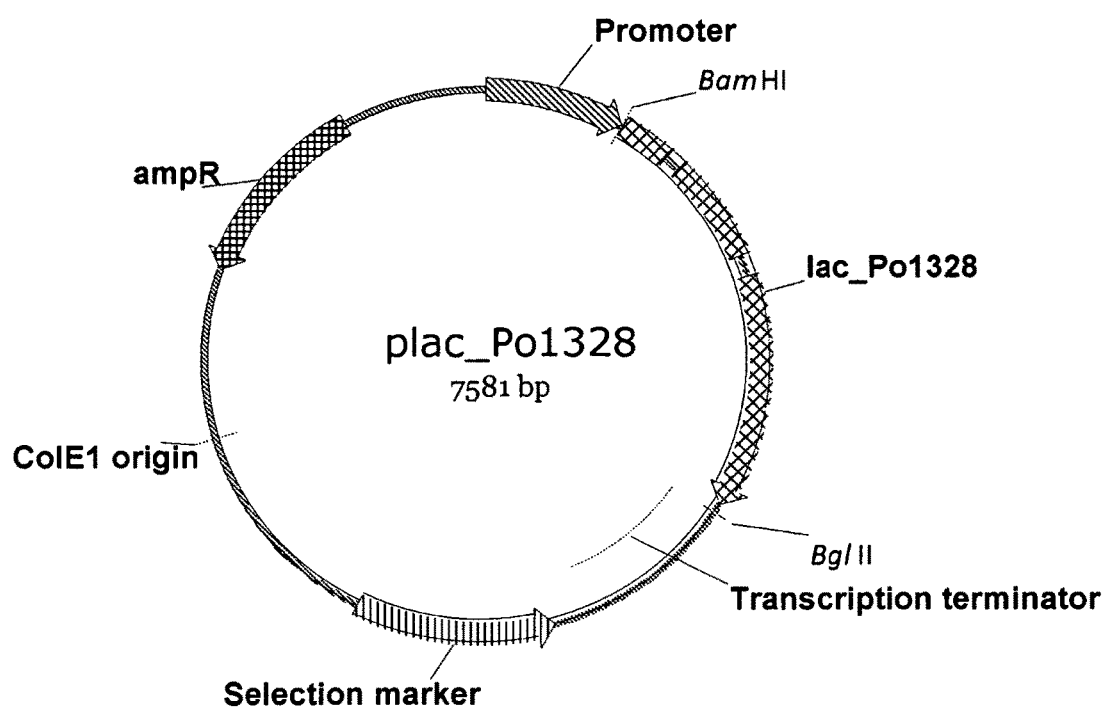
FIG. 16 shows a restriction map of p505-lac_Po1328.
Figure 17:
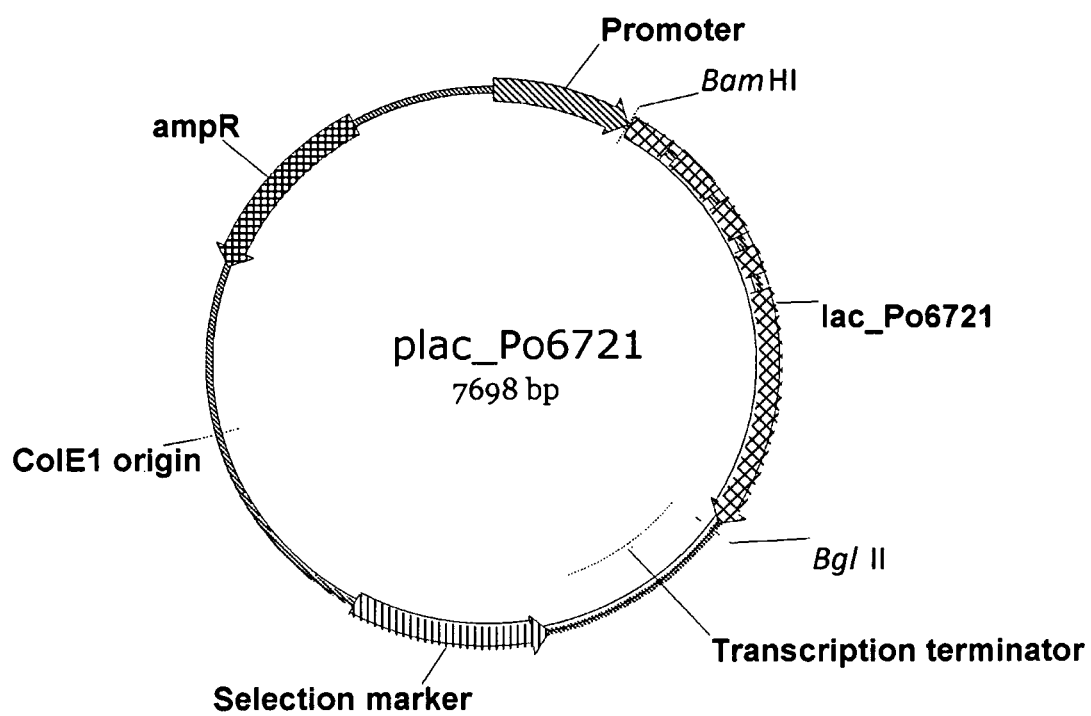
FIG. 17 shows a restriction map of p505-lac_Po6721.

| | Plasmids | |
|---|---|---|
| Gene name | Plasmid | DNA map |
| lac_Po1328 | p505-lac_Po1328 | FIG. 16 |
| lac_Po6721 | p505-lac_Po6721 | FIG. 17 |

Each PCR product and the digested vector were ligated together using an IN-FUSION® CF Dry-down Cloning Kit resulting in the plasmids shown in Table 7: p505-lac_Po1328 (FIG. 16) and p505-lac_Po6721 (FIG. 17) in which transcription of the *Penicillium oxalicum* laccase coding sequences was under the control of an *Aspergillus oryzae* alpha-amylase gene promoter. In brief, 30 ng of pCaHj505, digested with Bam HI and Bgl II, and 60 ng of each purified *Penicillium oxalicum* laccase PCR product were added to reaction vials and resuspended in a final volume of 10 µl by addition of deionized water. The reactions were incubated at 37° C. for 15 minutes and then 50° C. for 15 minutes. Three µl of the reactions were used to transform *E. coli* TOP10 competent cells. *E. coli* transformants containing expression constructs were detected by colony PCR as described in Example 3. Plasmid DNA was prepared from colonies showing inserts with the expected sizes using a QIAPREP® Spin Miniprep Kit. The *Penicillium oxalicum* laccase coding sequences inserted in p505-lac_Po1328 and p505-lac_Po6721 were confirmed by DNA sequencing using a 3730XL DNA Analyzer.

Example 14: Expression of *Penicillium oxalicum* Laccase Coding Sequences in *Aspergillus oryzae*

*Aspergillus oryzae* MT3568 protoplasts prepared according to the method of Christensen et al., 1988, supra, were transformed with 3 µg of p505-lac_Po1328. The transformations each yielded about 50 transformants. Eight transformants from each transformation were isolated to individual Minimal medium plates.

Four transformants from each transformation were inoculated separately into 3 ml of YPM medium in a 24-well plate and incubated at 30° C. with agitation at 150 rpm. After 3 days incubation, 20 µl of supernatant from each culture were analyzed by SDS-PAGE using a NUPAGE® NOVEX® 4-12% Bis-Tris Gel with 50 mM MES according to the manufacturers instructions. The resulting gel was stained with Instantblue. SDS-PAGE profiles of the cultures showed transformants of p505-lac_Po1328 had a major protein band at 80 kDa. One transformant was selected an expression strain and designated *Aspergillus oryzae* O229DE for p505-lac_Po1328.

Example 15: Assay for Laccase Activity

The activity of laccase was determined using 2,2'-azino-bis(3-ethylbenzothiazoline-6-sulfonic acid)diammonium salt, (ABTS, CAS number: 30931-67-0) as substrate. A 3.0 mM stock solution of the ABTS was prepared by mixing 16.5 mg of the ABTS with 10 ml of 100 mM sodium acetate pH 4. The reaction was started by adding 100 µl of laccase sample into 60 µl of the ABTS stock solution. A substrate control and enzyme control were included. The reaction was incubated at room temperature for 10 minutes. Absorbance at 405 nm was measured using a SPECTRAMAX® Microplate Reader (Molecular Devices, Sunnyvale, Calif., USA), and the result was used to calculate the activity of laccase.

The P24GU5 laccase (Example 10, O229DM) showed a laccase activity with an OD at 405 nm of 2.3235. The P33BS6 laccase (Example 12, O229DF) showed a laccase activity with an OD at 405 nm of 1.6606.

Example 16: Characterization of the Genomic DNAs Encoding Polypeptides Having Laccase Activity The genomic DNA sequence and deduced amino acid sequence of a *Malbranchea cinnamomea* laccase coding sequence are shown in SEQ ID NO: 1 (D82JWT) and SEQ ID NO: 2 (P24DW3), respectively. The coding sequence is 1947 bp including the stop codon, which is interrupted by 2 introns of 89 bp (nucleotides 242 to 330) and 82 bp (nucleotides 800 to 881). The encoded predicted protein is 591 amino acids. Using the SignalP program (Nielsen et al., 1997, supra), a signal peptide of 20 residues was predicted. The predicted mature protein contains 571 amino acids with a predicted molecular mass of 63.67 kDa and a predicted isoelectric point of 4.76.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Malbranchea cinnamomea* mature polypeptide having laccase activity shares 49.91% identity (excluding gaps) to the deduced amino acid sequence of a laccase from *Aspergillus fumigatus* (GENESEQP ABB80180).

The genomic DNA sequence and deduced amino acid sequence of another *Malbranchea cinnamomea* laccase coding sequence are shown in SEQ ID NO: 3 (D82MAT) and SEQ ID NO: 4 (P24EKS), respectively. The coding sequence is 2251 bp including the stop codon, which is interrupted by 5 introns of 103 bp (nucleotides 208 to 310), 70 bp (nucleotides 520 to 589), 56 bp (nucleotides 650 to 705), 73 bp (nucleotides 877 to 949), and 74 bp (nucleotides 1076 to 1149). The encoded predicted protein is 610 amino acids. Using the SignalP program (Nielsen et al., 1997, supra), a signal peptide of 25 residues was predicted. The predicted mature protein contains 599 amino acids with a predicted molecular mass of 67.44 kDa and a predicted isoelectric point of 5.30.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* mature polypeptide having laccase activity shares 82.98% identity (excluding gaps) to the deduced amino acid sequence of an oxidase from *Trichophyton verrucosum* (UNIPROT D4DBW4).

The genomic DNA sequence and deduced amino acid sequence of another *Malbranchea cinnamomea* laccase coding sequence are shown in SEQ ID NO: 5 (D82MAP) and SEQ ID NO: 6 (P24EKN), respectively. The coding sequence is 2138 bp including the stop codon, which is interrupted by 5 introns of 71 bp (nucleotides 202 to 272), 79 bp (nucleotides 425 to 503), 67 bp (nucleotides 557 to 623), 68 bp (1577 to 1644), and 95 bp (nucleotides 1857 to 1951). The encoded predicted protein is 585 amino acids. Using the SignalP program (Nielsen et al., 1997, supra), a signal peptide of 19 residues was predicted. The predicted mature protein contains 566 amino acids with a predicted molecular mass of 63.9 kDa and a predicted isoelectric point of 5.85.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* mature polypeptide having laccase activity shares 53.97% identity (excluding gaps) to the deduced amino acid sequence of a laccase from *Helotiaceas* sp. (UNIPROT A8Y7S9).

The genomic DNA sequence and deduced amino acid sequence of a *Rhizomucor pusillus* laccase coding sequence are shown in SEQ ID NO: 7 (D82NBW) and SEQ ID NO: 8 (P25F2C), respectively. The coding sequence is 1889 bp including the stop codon, which is interrupted by 2 introns of 60 bp (nucleotides 1579 to 1638) and 56 bp (nucleotides 1723 to 1778). The encoded predicted protein is 590 amino acids. Using the SignalP program (Nielsen et al., 1997, supra), a signal peptide of 23 residues was predicted. The predicted mature protein contains 567 amino acids with a predicted molecular mass of 65.2 kDa and a predicted isoelectric point of 5.92.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Rhizomucor pusillus* mature polypeptide having laccase activity shares 37.99% identity (excluding gaps) to the deduced amino acid sequence of a laccase from *Oryza sativa* (GENESEQP AWL07250).

The genomic DNA sequence and deduced amino acid sequence of another *Rhizomucor pusillus* laccase coding sequence are shown in SEQ ID NO: 9 (D82NBX) and SEQ ID NO: 10 (P24F2D), respectively. The coding sequence is 2079 bp including the stop codon, which is interrupted by 3 introns of 90 bp (nucleotides 266 to 355), 74 bp (nucleotides 1801 to 1875) and 60 bp (nucleotides 1892 to 1951). The encoded predicted protein is 617 amino acids. Using the SignalP program (Nielsen et al., 1997, supra), a signal peptide of 19 residues was predicted. The predicted mature protein contains 598 amino acids with a predicted molecular mass of 77.08 kDa and a predicted isoelectric point of 6.30.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Rhizomucor pusillus* mature polypeptide having laccase activity shares 38.96% identity (excluding gaps) to the deduced amino acid sequence of a laccase from *Oryza sativa* (UNIPROT Q5N9X2).

The genomic DNA sequence and deduced amino acid sequence of another *Rhizomucor pusillus* laccase coding sequence are shown in SEQ ID NO: 11 (D82NBY) and SEQ ID NO: 12 (P24F2E), respectively. The coding sequence is 1791 bp including the stop codon, which is interrupted by 1 intron of 73 bp (nucleotides 1591 to 1650). The encoded predicted protein is 576 amino acids. Using the SignalP program (Nielsen et at, 1997, supra), a signal peptide of 23 residues was predicted. The predicted mature protein contains 553 amino acids with a predicted molecular mass of 62.66 kDa and a predicted isoelectric point of 5.63.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Rhizomucor pusillus* mature polypeptide having laccase activity shares 41.12% identity (excluding gaps) to the deduced amino acid sequence of a protein from *Sorghum bicolor* (UNIPROT C5XB99).

The genomic DNA sequence and deduced amino acid sequence of a *Penicillium emersonii* laccase coding sequence are shown in SEQ ID NO: 13 (D82XFE) and SEQ ID NO: 14 (P24JJR), respectively. The coding sequence is 2166 bp including the stop codon, which is interrupted by 6 introns of 60 bp (nucleotides 196 to 255), 59 bp (nucleotides 312 to 370), 60 bp (nucleotides 482 to 541), 50 bp (nucleotides 602 to 651), 62 bp (nucleotides 823 to 884), and 54 bp (nucleotides 1011 to 1064). The encoded predicted protein is 606 amino acids. Using the SignalP program (Nielsen et al., 1997, supra), a signal peptide of 21 residues was predicted. The predicted mature protein contains 585 amino acids with a predicted molecular mass of 65.62 kDa and a predicted isoelectric point of 5.07.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium emersonii* mature polypeptide having laccase activity shares 65% identity (excluding gaps) to the deduced amino acid sequence of an oxidase from *Aspergillus oryzae* (UNIPROT Q2UA47).

The genomic DNA sequence and deduced amino acid sequence of another *Penicillium emersonii* laccase coding sequence are shown in SEQ ID NO: 15 (D82TPR) and SEQ ID NO: 16 (P24J2K), respectively. The coding sequence is 1726 bp including the stop codon, which is interrupted by 1 intron of 46 bp (nucleotides 866 to 911). The encoded predicted protein is 559 amino acids. Using the SignalP program (Nielsen et al., 1997, supra), a signal peptide of 16 residues was predicted. The predicted mature protein contains 543 amino acids with a predicted molecular mass of 59.74 kDa and a predicted isoelectric point of 4.44.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium emersonii* mature polypeptide having laccase activity shares 67.3% identity (excluding gaps) to the deduced amino acid sequence of a multicopper oxidase from *Aspergillus oryzae* (UNIPROT Q2UV32).

The genomic DNA sequence and deduced amino acid sequence of another *Penicillium emersonii* laccase coding sequence are shown in SEQ ID NO: 17 (D82T79) and SEQ ID NO: 18 (P24HYC), respectively. The coding sequence is 1879 bp including the stop codon, which is interrupted by 1 intron of 67 bp (nucleotides 289 to 355). The encoded predicted protein is 603 amino acids. Using the SignalP program (Nielsen et al., 1997, *Protein Engineering* 10: 1-6), a signal peptide of 23 residues was predicted. The predicted mature protein contains 580 amino acids with a predicted molecular mass of 64.60 kDa and a predicted isoelectric point of 4.86.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Penicillium emersonii* mature polypeptide having laccase activity shares 58.3% identity (excluding gaps) to the deduced amino acid sequence of a protein from *Aspergillus nidulans* (GENESEQP ATZ56392).

The genomic DNA sequence and deduced amino acid sequence of another *Penicillium emersonii* laccase coding sequence are shown in SEQ ID NO: 19 (D82XFD) and SEQ ID NO: 20 (P24JJQ), respectively. The coding sequence is 1926 bp including the stop codon, which is interrupted by 3 introns of 60 bp (nucleotides 343 to 402), 55 bp (nucleotides 898 to 952), and 65 bp (nucleotides 1174 to 1238). The encoded predicted protein is 581 amino acids. Using the SignalP program (Nielsen et al., 1997, supra), a signal peptide of 20 residues was predicted. The predicted mature protein contains 561 amino acids with a predicted molecular mass of 63.97 kDa and a predicted isoelectric point of 5.06.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium emersonii* mature polypeptide having laccase activity shares 66.6% identity (excluding gaps) to the deduced amino acid sequence of an oxidase from *Trichophyton verrucosum* (UNIPROT D4DJ87).

The genomic DNA sequence and deduced amino acid sequence of another *Penicillium emersonii* laccase coding sequence are shown in SEQ ID NO: 21 (D82TPQ) and SEQ ID NO: 22 (P24J2J), respectively. The coding sequence is 1892 bp including the stop codon, which is interrupted by 2 introns of 54 bp (nucleotides 239 to 292) and 47 bp (nucleotides 774 to 820). The encoded predicted protein is 596 amino acids. Using the SignalP program (Nielsen et al., 1997, supra), a signal peptide of 19 residues was predicted. The predicted mature protein contains 577 amino acids with a predicted molecular mass of 65.65 kDa and a predicted isoelectric point of 4.88.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium emersonii* mature polypeptide having laccase activity shares 58.7% identity (excluding gaps) to the deduced amino acid sequence of a laccase from *Aspergillus fumigatus* (GENESEQP ABB80180).

The genomic DNA sequence and deduced amino acid sequence of a *Thermoascus aurantiacus* laccase coding sequence are shown in SEQ ID NO: 23 (D82RVX) and SEQ ID NO: 24 (P24GU5), respectively. The coding sequence is 2115 bp including the stop codon, which is interrupted by 6 introns of 76 bp (nucleotides 187 to 262), 56 bp (nucleotides 381 to 436), 59 bp (nucleotides 556 to 614), 60 bp (nucleotides 712 to 771), 111 bp (nucleotides 1135 to 1245), and 61 bp (nucleotides 1714 to 1774). The encoded predicted protein is 563 amino acids. Using the SignalP program (Nielsen et al., 1997, supra), a signal peptide of 20 residues was predicted. The predicted mature protein contains 543 amino acids with a predicted molecular mass of 59.81 kDa and a predicted isoelectric point of 4.40.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Thermoascus aurantiacus* mature polypeptide having laccase activity shares 59.1% identity (excluding gaps) to the deduced amino acid sequence of a laccase from *Cryphonectria parasitica* (GENESEQP AXB70702).

The genomic DNA sequence and deduced amino acid sequence of another. *Thermoascus aurantiacus* laccase coding sequence are shown in SEQ ID NO: 25, (D82RW4) and SEQ ID NO: 26 (P24GU8), respectively. The coding sequence is 2111 bp including the stop codon, which is interrupted by 6 introns of 56 bp (nucleotides 196 to 251), 56 bp (nucleotides 308 to 363), 57 bp (nucleotides 475 to 531), 54 bp (nucleotides 592 to 645), 48 bp (nucleotides 817 to 1864), and 58 bp (nucleotides 991 to 1048). The encoded predicted protein is 593 amino acids. Using the SignalP program (Nielsen et al., 1997, supra), a signal peptide of 21 residues was predicted. The predicted mature protein contains 572 amino acids with a predicted molecular mass of 64.31 kDa and a predicted isoelectric point of 4.94.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Thermoascus aurantiacus* genomic DNA encoding a multicopper oxidase shares 65.3% identity (excluding gaps) to the deduced amino acid sequence of a multicopper oxidase from *Aspergillus oryzae* (UNIPROT Q2UA47).

The genomic DNA sequence and deduced amino acid sequence of a *Corynascus thermophilus* laccase coding sequence are shown in SEQ ID NO: 27 (D14E4X) and SEQ ID NO: 28 (P33BS4), respectively: The coding sequence is 1967 bp including the stop codon, which is interrupted by 3 introns of 62 bp (nucleotides 371 to 432), 59 bp (nucleotides 554 to 612), and 91 bp (nucleotides 1759 to 1849). The encoded predicted protein is 584 amino acids. Using the SignalP program (Nielsen et al., 1997, supra), a signal peptide of 22 residues was predicted. The predicted mature protein contains 562 amino acids with a predicted molecular mass of 62.97 kDa and a predicted isoelectric point of 5.54.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* mature polypeptide having laccase activity shares 73.48% identity (excluding gaps) to the deduced amino acid sequence of a protein from *Chaetomium globosum* (UNIPROT Q2HGW1).

The genomic DNA sequence and deduced amino acid sequence of another *Corynascus thermophilus* laccase coding sequence are shown in SEQ ID NO: 29 (D14E4Y) and SEQ ID NO: 30 (P33BS5), respectively. The coding sequence is 1990 bp including the stop codon, which is interrupted by 2 introns of 94 bp (nucleotides 93 to 186) and 75 bp (nucleotides 245 to 319). The encoded predicted protein is 606 amino acids. Using the SignalP program (Nielsen et al., 1997, supra), a signal peptide of 22 residues was predicted. The predicted mature protein contains 584 amino acids with a predicted molecular mass of 65.69 kDa and a predicted isoelectric point of 5.37.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* mature polypeptide having laccase activity shares 67.6% identity (excluding gaps) to the deduced amino acid sequence of a laccase from *Leptosphaeria maculans* (UNIPROT ESAE29).

The genomic. DNA sequence and deduced amino acid sequence of another *Corynascus thermophilus* laccase coding sequence are shown in SEQ ID NO: 31 (D14E4Z) and SEQ ID NO: 32 (P33BS6), respectively. The coding sequence is 2355 bp including the stop codon, which is interrupted by 6 introns of 85 bp (nucleotides 253 to 337), 73 bp (nucleotides 417 to 489), 103 bp (nucleotides 502 to 604), 67 bp (nucleotides 675 to 741), 75 bp (nucleotides 1706 to 1780) and 92 bp (nucleotides 1850 to 1941). The encoded predicted protein is 619 amino acids. Using the SignalP program (Nielsen et al., 1997, supra), a signal peptide of 21 residues was predicted. The predicted mature protein contains 598 amino acids with a predicted molecular mass of 67.19 kDa and a predicted isoelectric point of 5.13.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Corynascus thermophilus* mature polypeptide having laccase activity shares 68.29% identity (excluding gaps) to the deduced amino acid sequence of a laccase from *Myceliophthora thermophila* (GENESEQP AEF76888).

The genomic DNA sequence and deduced amino acid sequence of a *Penicillium oxalicum* laccase coding sequence are shown in SEQ ID NO: 33 (D14E5I) and SEQ ID NO:

34 (P33BS7), respectively. The coding sequence is 1927 bp including the stop codon, which is interrupted by 2 introns of 73 bp (nucleotides 233 to 305) and 96 bp (nucleotides 781 to 876). The encoded predicted protein is 585 amino acids. Using the SignalP program (Nielsen et al., 1997, supra), a signal peptide of 17 residues was predicted. The predicted mature protein contains 568 amino acids with a predicted molecular mass of 62.69 kDa and a predicted isoelectric point of 5.90.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium oxalicum* mature polypeptide having laccase activity shares 61.44% identity (excluding gaps) to the deduced amino acid sequence of a laccase from *Penicillium chrysogenum* (UNIPROT B6GYH8).

The genomic DNA sequence and deduced amino acid sequence of another *Penicillium oxalicum* laccase coding sequence are shown in SEQ ID NO: 35 (D14E55) and SEQ ID NO: 36 (P33BSB), respectively. The coding sequence is 2053 bp including the stop codon, which is interrupted by 4 introns of 53 bp (nucleotides 196 to 248), 50 bp (nucleotides 476 to 525), 62 bp (nucleotides 697 to 758), and 73 bp (nucleotides 885 to 957). The encoded predicted protein is 604 amino acids. Using the SignalP program (Nielsen et al., 1997, supra), a signal peptide of 21 residues was predicted. The predicted mature protein contains 583 amino acids with a predicted molecular mass of 65.48 kDa and a predicted isoelectric point of 5.11.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Penicillium oxalicum* mature polypeptide having laccase activity shares 62.7% identity (excluding gaps) to the deduced amino acid sequence of a multicopper oxidase from *Aspergillus oryzae* (UNIPROT Q2UA47).

The present invention is further described by the following numbered paragraphs:

[1] An isolated polypeptide having laccase activity, selected from the group consisting of: (a) a polypeptide having at least 60% sequence identity to the mature polypeptide of SEQ ID NO: 2, SEQ ID NO: 6, SEQ ID NO: 8, SEQ ID NO: 10, SEQ ID NO: 12, SEQ ID NO:18, SEQ ID NO: 22, or SEQ ID NO: 24; at least 65% sequence identity to the mature polypeptide of SEQ ID NO: 34 or SEQ ID NO: 36; at least 70% sequence identity to the mature polypeptide of SEQ ID NO: 14, SEQ ID NO: 16, SEQ ID NO: 20, SEQ ID NO: 26, SEQ ID NO: 30, or SEQ ID NO: 32; at least 75% sequence identity to the mature polypeptide of SEQ ID NO: 28; or at least 85% sequence identity to the mature polypeptide of SEQ ID NO: 4; (b) a polypeptide encoded by a polynucleotide that hybridizes under at least medium-high stringency conditions with (i) the mature polypeptide coding sequence of SEQ ID NO: 1, SEQ ID NO: 5, SEQ ID NO: 7, SEQ ID NO: 9, SEQ ID NO: 11, SEQ ID NO:17, SEQ ID NO: 21, SEQ ID NO: 23, SEQ ID NO: 33, or SEQ ID NO: 35, (ii) the cDNA sequence thereof, or (iii) the full-length complement of (i) or (ii); or at least high stringency conditions with (i) the mature polypeptide coding sequence of SEQ ID NO: 13, SEQ ID NO: 15, SEQ ID NO: 19, SEQ ID NO: 25, SEQ ID NO: 27, SEQ ID NO: 29, or SEQ ID NO: 31, (ii) the cDNA sequence thereof, or (iii) the full-length complement of (i) or (ii); or at least very high stringency conditions with (i) the mature polypeptide coding sequence of SEQ ID NO: 3, (ii) the cDNA sequence thereof, or (iii) the full-length complement of (i) or (ii); (c) a polypeptide encoded by a polynucleotide having at least 60% sequence identity to the mature polypeptide coding sequence of SEQ ID NO: 1, SEQ ID NO: 5, SEQ ID NO: 7, SEQ ID NO: 9, SEQ ID NO: 11, SEQ ID NO:17, SEQ ID NO: 21, or SEQ ID NO: 23, or the cDNA sequences thereof; at least 65% sequence identity to the mature polypeptide coding sequence of SEQ ID NO: 33 or SEQ ID NO: 35, or the cDNA sequences thereof; at least 70% sequence identity to the mature polypeptide coding sequence of SEQ ID NO: 13, SEQ ID NO: 15, SEQ ID NO: 19, SEQ ID NO: 25, SEQ ID NO: 29, or SEQ ID NO: 31, or the cDNA sequences thereof; at least 75% sequence identity to the mature polypeptide coding sequence of SEQ ID NO: 27 or the cDNA sequence thereof; or at least 85% sequence identity to the mature polypeptide coding sequence of SEQ ID NO: 3 or the cDNA sequence thereof; (d) a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36 comprising a substitution, deletion, and/or insertion at one or more (e.g., several) positions; and (e) a fragment of the polypeptide of (a), (b), (c), or (d) that has laccase activity.

[2] The polypeptide of paragraph 1, having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2, SEQ ID NO: 6, SEQ ID NO: 8, SEQ ID NO: 10, SEQ ID NO: 12, SEQ ID NO:18, SEQ ID NO: 22, or SEQ ID NO: 24; at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 34 or SEQ ID NO: 36; at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 14, SEQ ID NO: 16, SEQ ID NO: 20, SEQ ID NO: 26, SEQ ID NO: 30, or SEQ ID NO: 32; at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 28; or at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to mature polypeptide of SEQ ID NO: 4.

[3] The polypeptide of paragraph 1, which is encoded by a polynucleotide that hybridizes under medium-high, high, or very high stringency conditions with (i) the mature polypeptide coding sequence of SEQ ID NO: 1, SEQ ID NO: 5, SEQ ID NO: 7, SEQ ID NO: 9, SEQ ID NO: 11, SEQ ID NO:17, SEQ ID NO: 21, SEQ ID NO: 23, SEQ ID NO: 33, or SEQ ID NO: 35, (ii) the cDNA sequence thereof, or (iii) the full-length complement of (i) or (ii); or high or very high stringency conditions with (i) the mature polypeptide coding sequence of SEQ ID NO: 13, SEQ ID NO: 15, SEQ ID NO: 19, SEQ ID NO: 25, SEQ ID NO: 27, SEQ ID NO: 29, or SEQ ID NO: 31; (ii) the cDNA sequence thereof, or (iii) the full-length complement of (i) or (ii); or very high stringency conditions with (i) the mature polypeptide coding sequence of SEQ ID NO: 3, (ii) the cDNA sequence thereof, or (iii) the full-length complement of (i) or (ii).

[4] The polypeptide of paragraph 1, which is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, SEQ ID NO: 5, SEQ ID NO: 7, SEQ ID NO: 9, SEQ ID NO: 11, SEQ ID NO:17, SEQ ID NO: 21, or SEQ ID NO: 23, or the cDNA sequences thereof; at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 33 or SEQ. ID NO: 35, or the cDNA sequences thereof; at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 13, SEQ ID NO: 15, SEQ ID NO: 19, SEQ ID NO: 25, SEQ ID NO: 29, or SEQ ID NO: 31, or the cDNA sequences thereof; at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 27 or the cDNA sequence thereof; or at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to mature polypeptide coding sequence of SEQ ID NO: 3 or the cDNA sequence thereof.

[5] The polypeptide of any of paragraphs 1-4, comprising or consisting of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36.

[6] The polypeptide of paragraph 5, wherein the mature polypeptide is amino acids 21 to 591 of SEQ ID NO: 2, amino acids 26 to 610 of SEQ ID NO: 4, amino acids 20 to 585 of SEQ ID NO: 6, amino acids 24 to 590 of SEQ ID NO: 8, amino acids 20 to 617 of SEQ ID NO: 10, amino acids 24 to 576 of SEQ ID NO: 12, amino acids 22 to 606 of SEQ ID NO: 14, amino acids 17 to 559 of SEQ ID NO: 16, amino acids 24 to 603 of SEQ ID NO: 18, amino acids 21 to 581 of SEQ ID NO: 20, amino acids 20 to 596 of SEQ ID NO: 22, amino acids 21 to 563 of SEQ ID NO: 24, amino acids 22 to 593 of SEQ ID NO: 26, amino acids 23 to 584 of SEQ ID NO: 28, amino acids 23 to 606 of SEQ ID NO: 30, amino acids 22 to 619 of SEQ ID NO: 32, amino acids 18 to 585 of SEQ ID NO: 34, amino acids 22 to 604 of SEQ ID NO: 36.

[7] The polypeptide of paragraph 1, which is a variant of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36 comprising a substitution, deletion, and/or insertion at one or more positions.

[8] The polypeptide of paragraph 1, which is a fragment of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36, wherein the fragment has laccase activity.

[9] A composition comprising the polypeptide of any of paragraphs 1-8.

[10] An isolated polynucleotide encoding the polypeptide of any of paragraphs 1-8.

[11] A nucleic acid construct or expression vector comprising the polynucleotide of paragraph 10 operably linked to one or more control sequences that direct the production of the polypeptide in an expression host.

[12] A recombinant host cell comprising the polynucleotide of paragraph 10 operably linked to one or more control sequences that direct the production of the polypeptide.

[13] A method of producing the polypeptide of any of paragraphs 1-8, comprising: cultivating a cell, which in its wild-type form produces the polypeptide, under conditions conducive for production of the polypeptide.

[14] The method of paragraph 13, further comprising recovering the polypeptide.

[15] A method of producing a polypeptide having laccase activity, comprising: cultivating the host cell of paragraph 12 under conditions conducive for production of the polypeptide.

[16] The method of paragraph 15, further comprising recovering the polypeptide.

[17] A transgenic plant, plant part or plant cell transformed with a polynucleotide encoding the polypeptide of any of paragraphs 1-8.

[18] A method of producing a polypeptide having laccase activity, comprising: cultivating the transgenic plant or plant cell of paragraph 17 under conditions conducive for production of the polypeptide.

[19] The method of paragraph 18, further comprising recovering the polypeptide.

[20] A method of producing a mutant of a parent cell, comprising inactivating a polynucleotide encoding the polypeptide of any of paragraphs 1-8, which results in the mutant producing less of the polypeptide than the parent cell.

[21] A mutant cell produced by the method of paragraph 20.

[22] The mutant cell of paragraph 21, further comprising a gene encoding a native or heterologous protein.

[23] A method of producing a protein, comprising: cultivating the mutant cell of paragraph 21 or 22 under conditions conducive for production of the protein.

[24] The method of paragraph 23, further comprising recovering the protein.

[25] A double-stranded inhibitory RNA (dsRNA) molecule comprising a subsequence of the polynucleotide of paragraph 10, wherein optionally the dsRNA is an siRNA or an miRNA molecule.

[26] The double-stranded inhibitory RNA (dsRNA) molecule of paragraph 25, which is about 15, 16, 17, 18, 19, 20, 21, 22, 23, 24, 25 or more duplex nucleotides in length.

[27] An method of inhibiting the expression of a polypeptide having laccase activity in a cell, comprising administering to the cell or expressing in the cell the double-stranded inhibitory RNA (dsRNA) molecule of paragraph 25 or 26.

[28] A cell produced by the method of paragraph 27.

[29] The cell of paragraph 28, further comprising a gene encoding a native or heterologous protein.

[30] A method of producing a protein, comprising: cultivating the cell of paragraph 28 or 29 under conditions conducive for production of the protein.

[31] The method of paragraph 30, further comprising recovering the protein.

[32] An isolated polynucleotide encoding a signal peptide comprising or consisting of amino acids 1 to 20 of SEQ ID NO: 2, amino acids 1 to 25 of SEQ ID NO: 4, amino acids 1 to 19 of SEQ ID NO: 6, amino acids 1 to 23 of SEQ ID NO: 8, amino acids 1 to 19 of SEQ ID NO: 10, amino acids 1 to 23 of SEQ ID NO: 12, amino acids 1 to 21 of SEQ ID NO: 14, amino acids 1 to 16 of SEQ ID NO: 16, amino acids 1 to 23 of SEQ ID NO: 18, amino acids 1 to 20 of SEQ ID NO: 20, amino acids 1 to 19 of SEQ ID NO: 22, amino acids 1 to 20 of SEQ ID NO: 24, amino acids 1 to 21 of SEQ ID NO: 26, amino acids 1 to 22 of SEQ ID NO: 28, amino acids 1 to 22 of SEQ ID NO: 30, amino acids 1 to 21 of SEQ ID NO: 32, amino acids 1 to 17 of SEQ ID NO: 34, or amino acids 1 to 21 of SEQ ID NO: 36.

[33] A nucleic acid construct or expression vector comprising a gene encoding a protein operably linked to the polynucleotide of paragraph 32, wherein the gene is foreign to the polynucleotide encoding the signal peptide.

[34] A recombinant host cell comprising a gene encoding a protein operably linked to the polynucleotide of paragraph 32, wherein the gene is foreign to the polynucleotide encoding the signal peptide.

[35] A method of producing a protein, comprising: cultivating a recombinant host cell comprising a gene encoding a protein operably linked to the polynucleotide of paragraph 32, wherein the gene is foreign to the polynucleotide encoding the signal peptide, under conditions conducive for production of the protein.

[36] The method of paragraph 35, further comprising recovering the protein.

[37] A process for degrading a cellulosic material, comprising: treating the cellulosic material with an enzyme composition in the presence of the polypeptide having laccase activity of any of paragraphs 1-8.

[38] The process of paragraph 37, wherein the cellulosic material is pretreated.

[39] The process of paragraph 37 or 38, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[40] The process of paragraph 39, wherein the cellulase is one or more enzymes selected from the group consisting of an endoglucanase, a cellobiohydrolase, and a beta-glucosidase.

[41] The process of paragraph 39, wherein the hemicellulase is one or more enzymes selected from the group consisting of a xylanase, an acetylxylan esterase, a feruloyl esterase, an arabinofuranosidase, a xylosidase, and a glucuronidase.

[42] The process of any of paragraphs 37-41, wherein the enzyme composition comprises a mediator of laccase activity.

[43] The process of any of paragraphs 37-42, further comprising recovering the degraded cellulosic material.

[44] The process of paragraph 43, wherein the degraded cellulosic material is a sugar.

[45] The process of paragraph 44, wherein the sugar is selected from the group consisting of glucose, xylose, mannose, galactose, and arabinose.

[46] A process for producing a fermentation product, comprising: (a) saccharifying a cellulosic material with an enzyme composition in the presence of the polypeptide having laccase activity of any of paragraphs 1-8; (b) fermenting the saccharified cellulosic material with one or more fermenting microorganisms to produce the fermentation product; and (c) recovering the fermentation product from the fermentation.

[47] The process of paragraph 46, wherein the cellulosic material is pretreated.

[48] The process of paragraph 46 or 47, wherein the enzyme composition comprises the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[49] The process of paragraph 48, wherein the cellulase is one or more enzymes selected from the group consisting of an endoglucanase, a cellobiohydrolase, and a beta-glucosidase.

[50] The process of paragraph 48, wherein the hemicellulase is one or more enzymes selected from the group consisting of a xylanase, an acetylxylan esterase, a feruloyl esterase, an arabinofuranosidase, a xylosidase, and, a glucuronidase.

[51] The process of any of paragraphs 46-50, wherein the enzyme composition comprises a mediator of laccase activity.

[52] The process of any of paragraphs 46-51, wherein steps (a) and (b) are performed simultaneously in a simultaneous saccharification and fermentation.

[53] The process of any of paragraphs 46-52, wherein the fermentation product is an alcohol, an alkane, a cycloalkane, an alkene, an amino acid, a gas, isoprene, a ketone, an organic acid, or polyketide.

[54] A process of fermenting a cellulosic material, comprising: fermenting the cellulosic material with one or more fermenting microorganisms, wherein the cellulosic material is saccharified with an enzyme composition in the presence of the polypeptide having laccase activity of any of paragraphs 1-8.

[55] The process of paragraph 54, wherein the fermenting of the cellulosic material produces a fermentation product.

[56] The process of paragraph 55, further comprising recovering the fermentation product from the fermentation.

[57] The process of paragraph 55 or 56, wherein the fermentation product is an alcohol, an alkane, a cycloalkane, an alkene, an amino acid, a gas, isoprene, a ketone, an organic acid, or polyketide.

[58] The process of any of paragraphs 54-57, wherein the cellulosic material is pretreated before saccharification.

[59] The process of any of paragraphs 54-58, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[60] The process of paragraph 59, wherein the cellulase is one or more enzymes selected from the group consisting of an endoglucanase, a cellobiohydrolase, and a beta-glucosidase.

[61] The process of paragraph 59, wherein the hemicellulase is one or more enzymes selected from the group consisting of a xylanase, an acetylxylan esterase, a feruloyl esterase, an arabinofuranosidase, a xylosidase, and a glucuronidase.

[62] The process of any of paragraphs 54-61, wherein the enzyme composition comprises a mediator of laccase activity.

[63] A process for detoxifying pre-treated lignocellulose-containing material comprising subjecting the pre-treated lignocellulose-containing material to the polypeptide of any of paragraphs 1-8.

[64] A process of producing a fermentation product, comprising: (a) pretreating a cellulosic material, (b) detoxifying the pretreated cellulosic material with the polypeptide having laccase activity of any of paragraphs 1-8; (c) saccharifying the detoxified cellulosic material with an enzyme composition optionally in the presence of the polypeptide having laccase activity; (d) fermenting the saccharified cellulosic material with one or more (e.g., several) fermenting microorganisms to produce the fermentation product; and (e) recovering the fermentation product from the fermentation.

[65] The process of paragraph 64, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[66] The process of paragraph 65, wherein the cellulase is one or more enzymes selected from the group consisting of an endoglucanase, a cellobiohydrolase, and a beta-glucosidase.

[67] The process of paragraph 65, wherein the hemicellulase is one or more enzymes selected from the group consisting of a xylanase, an acetylxylan esterase, a feruloyl esterase, an arabinofuranosidase, a xylosidase, and a glucuronidase.

[68] The process of any of paragraphs 64-67, wherein the enzyme composition comprises a mediator of laccase activity.

[69] The process of any of paragraphs 64-68, wherein steps (c) and (d) are performed simultaneously in a simultaneous saccharification and fermentation.

[70] The process of any of paragraphs 64-69, wherein the fermentation product is an alcohol, an alkane, a cycloalkane, an alkene, an amino acid, a gas, isoprene, a ketone, an organic acid, or polyketide.

[71] A process of producing a fermentation product, comprising: (a) pretreating a cellulosic material, (b) saccharifying the pretreated cellulosic material with an enzyme composition in the presence of the polypeptide having laccase activity of any of paragraphs 1-8; (c) fermenting the saccharified cellulosic material with one or more (e.g., several) fermenting microorganisms to produce the fermentation product; and (d) recovering the fermentation product from the fermentation.

[72] The process of paragraph 71, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[73] The process of paragraph 72, wherein the cellulase is one or more enzymes selected from the group consisting of an endoglucanase, a cellobiohydrolase, and a beta-glucosidase.

[74] The process of paragraph 72, wherein the hemicellulase is one or more enzymes selected from the group consisting of a xylanase, an acetylxylan esterase, a feruloyl esterase, an arabinofuranosidase, a xylosidase, and a glucuronidase.

[75] The process of any of paragraphs 71-74, wherein the enzyme composition comprises a mediator of laccase activity.

[76] The process of any of paragraphs 71-75, wherein steps (b) and (c) are performed simultaneously in a simultaneous saccharification and fermentation.

[77] The process of any of paragraphs 71-76, wherein the fermentation product is an alcohol, an alkane, a cycloalkane, an alkene, an amino acid, a gas, isoprene, a ketone, an organic acid, or polyketide.

[78] A whole broth formulation or cell culture composition comprising the polypeptide of any of paragraphs 1-8.

[79] Use of the laccase of any of paragraphs 1-8 for oxidizing a substrate.

[80] Use of the laccase of paragraph 79 for dye transfer inhibition.

[81] Use of the laccase of paragraph 79 for bleaching textiles, in particular for bleaching denim.

[82] A detergent additive comprising the laccase of any of paragraphs 1-8 in the form of a non-dusting granulate, a stabilised liquid or a protected enzyme.

[83] The detergent additive of paragraph 82, which additionally comprises one or more other enzyme such as a protease, a lipase, an amylase, and/or a cellulase.

[84] A detergent composition comprising a laccase of any of paragraphs 1-8 and a surfactant.

[85] The detergent composition according to paragraph 84 which additionally comprises one or more other enzymes such as a protease, a lipase, an amylase and/or a cellulase.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process for degrading a cellulosic material, comprising: treating the cellulosic material with an enzyme composition in the presence of the polypeptide having laccase activity, selected from the group consisting of:
   (a) a polypeptide having at least 90% sequence identity to the mature polypeptide of SEQ ID NO: 24;
   (c) a polypeptide encoded by a polynucleotide having at least 90% sequence identity to the mature polypeptide coding sequence of SEQ ID NO: 23, or the cDNA sequences thereof.

2. The process of claim 1, wherein the polypeptide having laccase activity comprises or consists of the mature polypeptide of SEQ ID NO: 24.

3. The process of claim 2, wherein the mature polypeptide is amino acids 21 to 563 of SEQ ID NO: 24.

4. The process of claim 1, wherein the polypeptide having laccase activity is a variant of the mature polypeptide of SEQ ID NO: 24 comprising a substitution, deletion, and/or insertion at one or more positions and having at least 90% sequence identity to the mature polypeptide of SEQ ID NO: 24.

5. The process of claim 1, wherein the polypeptide having laccase activity is a fragment of the polypeptide having at least 90% sequence identity to the mature polypeptide of SEQ ID NO: 24.

* * * * *

SEQUENCE LISTING

<160> NUMBER OF SEQ ID NOS: 70

<210> SEQ ID NO 1
<211> LENGTH: 1947
<212> TYPE: DNA
<213> ORGANISM: Malbranchea cinnamomea

<400> SEQUENCE: 1

```
atgggtatct ctgcgatgtt ttatctttgc ctccttgccc tcgtggctcc ggtttggagc      60
aaaactgtct tttatgaact caagcttacc tgggagaaat acagcccaga cggccatgag     120
cgggacatga tcctcattaa cgggcaattc cctggcccgc gcttggaagc ggaccaggga     180
gacgaggtcc atgtcttagt caccaataac atgcccttgt atacatccgt tcacttccac     240
ggtacgtagt gtgaagggga tatagtcgat cagacggccc cgtgtaagcc ataaagcacg     300
tggctgacaa aatcccctc ccaaaaaaag gaatcgagca atatcggacg ctatggtcag     360
acggcacacc aggagtgacg caacggccca ttcacgccgg acaacaattc ttgtacaagt     420
gggttgcgac cgagtacggc agctactggt atcacgccca ctcaagaggc cagattgacg     480
acgggctctt cggtccgctc ctgatccggc ccaatacct cagacggttg cctttgcat      540
ctctcagctc gaactccatc gattctcgca agttgagccg ggcgtatgag aactcgaagg     600
ccatgattgt tggagactgg actcacgagc cgtcgcatga agtttgggac gtcgcacagg     660
cttccggagt agacatgata tgtccagaca gcattctcat caacgggaag ggatgggtca     720
aatgcccgac tccgaggag ctcgctgatc caggtccatt ggcccctatc ctgggaaatc      780
aaactttgac cgataagggg ttagttatta ttattttttt ttcctttttc attttttgttt    840
ttggtgattt tggatctgac tggctaattg actggtcgta gatgtcttcc acctgataac     900
gtgttgggtc aaggagacta cccacatgat tacgacaaac tgccagacaa atacttctat     960
atctgcgaag atacggaggg atcacaggag gtaattgaag tgtccagctc ccagggtggg    1020
ctcagtttgg actggatttc ccatgccgga atggacgcgt tgtccctctc ggtggacgaa    1080
cacccgcaaa tcgtgtatgc agttgacggt cgctttatcc agccgtacga ggtccatgca    1140
cttgtcatcg accccggtgc gagatactca gtcatgatca agctcgataa gcctgcggga    1200
cgaaagtact caatccgagt taccaataag ggggccaacc aggtcctggg aaccacagcg    1260
attcttcat acataggaga acccgatgac acgccgtcgc agccatatac tgacagattc    1320
ggttatctgg tttcggaaga cttgatcgag ttcaatgaag cattggcaat tccagatcca    1380
ccggttgtcc ctggaaccaa tgtcaaccaa acatttatat ttgatgttgg ccgttggaat    1440
gcttccttcc tctggacggt gaacggaatc gcaaggtttc ccgatctcga ctgggctgag    1500
gaccaggagc cactccttt cgatccttct aacgccttcg acctcaacgt aaccatcacg    1560
acctacaacg ataccggggt tgacatggtc ttccgcgcga accccatcca gcctcctcac    1620
ccaatccaca agcattcaaa caaagtcttt attctgggcc atggggaggg accattcccc    1680
tattccactg ttgcggaagc cattgctgcg gagcctgaaa atttcaacct tgagactcct    1740
ttactgaggg acacttggat ccctccacct gcggtcacag gaccaacctg gatagccgtg    1800
cggtaccatg tggtgaatcc gggagccagc ttcttgcact gtcacataaa tcctcattta    1860
gctgaggta tggcattggc aatcctggac ggcgtcgatg cttggccgga agttccaccc    1920
gagtacctga acgggaatgg gatgtga                                       1947
```

<210> SEQ ID NO 2
<211> LENGTH: 591

<212> TYPE: PRT
<213> ORGANISM: Malbranchea cinnamomea

<400> SEQUENCE: 2

```
Met Gly Ile Ser Ala Met Phe Tyr Leu Cys Leu Leu Ala Leu Val Ala
1               5                   10                  15

Pro Val Trp Ser Lys Thr Val Phe Tyr Glu Leu Lys Leu Thr Trp Glu
            20                  25                  30

Lys Tyr Ser Pro Asp Gly His Glu Arg Asp Met Ile Leu Ile Asn Gly
        35                  40                  45

Gln Phe Pro Gly Pro Arg Leu Glu Ala Asp Gln Gly Asp Glu Val His
    50                  55                  60

Val Leu Val Thr Asn Asn Met Pro Phe Asp Thr Ser Val His Phe His
65                  70                  75                  80

Gly Ile Glu Gln Tyr Arg Thr Leu Trp Ser Asp Gly Thr Pro Gly Val
                85                  90                  95

Thr Gln Arg Pro Ile His Ala Gly Gln Gln Phe Leu Tyr Lys Trp Val
            100                 105                 110

Ala Thr Glu Tyr Gly Ser Tyr Trp Tyr His Ala His Ser Arg Gly Gln
        115                 120                 125

Ile Asp Asp Gly Leu Phe Gly Pro Leu Leu Ile Arg Pro Asn Thr Leu
    130                 135                 140

Arg Arg Leu Pro Phe Ala Ser Leu Ser Ser Asn Ser Ile Asp Ser Arg
145                 150                 155                 160

Lys Leu Ser Arg Ala Tyr Glu Asn Ser Lys Ala Met Ile Val Gly Asp
                165                 170                 175

Trp Thr His Glu Pro Ser His Glu Val Trp Asp Val Ala Gln Ala Ser
            180                 185                 190

Gly Val Asp Met Ile Cys Pro Asp Ser Ile Leu Ile Asn Gly Lys Gly
        195                 200                 205

Trp Val Lys Cys Pro Thr Pro Glu Glu Leu Ala Asp Pro Gly Pro Leu
    210                 215                 220

Ala Pro Ile Leu Gly Asn Gln Thr Leu Thr Asp Lys Gly Cys Leu Pro
225                 230                 235                 240

Pro Asp Asn Val Leu Gly Gln Gly Asp Tyr Pro His Asp Tyr Asp Lys
                245                 250                 255

Leu Pro Asp Lys Tyr Phe Tyr Ile Cys Glu Asp Thr Glu Gly Ser Gln
            260                 265                 270

Glu Val Ile Glu Val Ser Ser Ser Gln Gly Trp Leu Ser Leu Asp Trp
        275                 280                 285

Ile Ser His Ala Gly Met Asp Ala Leu Ser Leu Ser Val Asp Glu His
    290                 295                 300

Pro Gln Ile Val Tyr Ala Val Asp Gly Arg Phe Ile Gln Pro Tyr Glu
305                 310                 315                 320

Val His Ala Leu Val Ile Asp Pro Gly Ala Arg Tyr Ser Val Met Ile
                325                 330                 335

Lys Leu Asp Lys Pro Ala Gly Arg Lys Tyr Ser Ile Arg Val Thr Asn
            340                 345                 350

Lys Gly Ala Asn Gln Val Leu Gly Thr Thr Ala Ile Leu Ser Tyr Ile
        355                 360                 365

Gly Glu Pro Asp Asp Thr Pro Ser Gln Pro Tyr Thr Asp Arg Phe Gly
    370                 375                 380

Tyr Leu Val Ser Glu Asp Leu Ile Glu Phe Asn Glu Ala Leu Ala Ile
385                 390                 395                 400
```

```
Pro Asp Pro Val Val Pro Gly Thr Asn Val Asn Gln Thr Phe Ile
            405                 410                 415

Phe Asp Val Gly Arg Trp Asn Ala Ser Phe Leu Trp Thr Val Asn Gly
            420                 425                 430

Ile Ala Arg Phe Pro Asp Leu Asp Trp Ala Glu Asp Gln Glu Pro Leu
            435                 440                 445

Leu Phe Asp Pro Ser Asn Ala Phe Asp Leu Asn Val Thr Ile Thr Thr
450                 455                 460

Tyr Asn Asp Thr Trp Val Asp Met Val Phe Arg Ala Asn Pro Ile Gln
465                 470                 475                 480

Pro Pro His Pro Ile His Lys His Ser Asn Lys Val Phe Ile Leu Gly
            485                 490                 495

His Gly Glu Gly Pro Phe Pro Tyr Ser Thr Val Ala Glu Ala Ile Ala
            500                 505                 510

Ala Glu Pro Glu Asn Phe Asn Leu Glu Thr Pro Leu Leu Arg Asp Thr
            515                 520                 525

Trp Ile Pro Pro Pro Ala Val Thr Gly Pro Thr Trp Ile Ala Val Arg
            530                 535                 540

Tyr His Val Val Asn Pro Gly Ala Ser Phe Leu His Cys His Ile Asn
545                 550                 555                 560

Pro His Leu Ala Gly Gly Met Ala Leu Ala Ile Leu Asp Gly Val Asp
            565                 570                 575

Ala Trp Pro Glu Val Pro Pro Glu Tyr Leu Asn Gly Asn Gly Met
            580                 585                 590

<210> SEQ ID NO 3
<211> LENGTH: 2251
<212> TYPE: DNA
<213> ORGANISM: Malbranchea cinnamomea

<400> SEQUENCE: 3
atgtgtgact cgcgggttcc agttactctt cttgcactcg tagtatttgc cgtgaccacg      60
ggaatggcga cggcaaagct cgttcaggaa gagttgacat tgacatggag cgtcggagcg     120
ccaaatggac agcccaggga gatgatcttc atgaacggcg aattcccggg gccaaccttc     180
atgtgggatg aagacgatga tatcgaggta aggcccggat ttgactgaat cgcaccggtg     240
tctcactgtg tcaaaagtg gaaaggcgag aatgcactaa cggattggcc caggtcactg      300
tgcataacag gatgccattc aacacgacga tacattggca tggactcctg tatggcccat     360
ccagctgttc cctaggcgca aaaggaagag tgccacttac tcggccagga tgcagggcac     420
gccctggtcc gacggtgttc caggtctaac tcagaagcca atcgaacctg ggcgtctttt      480
tatttatcgc ttcaaggcgt atccgtcggg aacacactgg taagattgcg tctttgagtt     540
tgatctgcct tttttttttt tggtcgttta aactcacgag aataataagg tggcattcac     600
actcccgcac gaccctgctt gatggattat atggtgctct gtatatcagg tacgaccgcc     660
aaaacctctt gacggaagtg tcgattctaa cccgatatct ccaagaccga accaagcaa      720 gccgtcccca tggcatttga tcagcaatga tgaaacggac attgcgagta tgcaaaaggc     780
cgtggctgat ccaaaggtga ttgtgatatc agactggacc cagtttaaat cgtgggaata     840
tatggaagcg caagcgaact cggggtatac aattttgtat gcctccctag cttcccccctt     900 tctctctctc tctctctccc ttccacaagc tcaaacttt actttatagc tgcgtggaca     960
gtctcctgat taatggtaag ggcagcgtct actgtcccgg tgaagacttt ctggtaaacc    1020
```

-continued

```
tcaccagcaa ctacatgaaa tgggcgatat atccccgcca cgtgaatgac aaagggtaga      1080
gcattttact ctcttttcag ccttgatttg gtgcaatgat atgaacaatg gctgaccctg      1140
ccgcgcaaga tgcctaccgt ttgtcaaatc aaccgaaaac aaatatctca aggcggccg       1200 gccagagaca attcccttgc atctgcagca gggatgtgtg ccatctgagg gcgatcgcac      1260
aatcattgag gtcgatcccg cggacggttg ggtgagtctc aattttgtgg atgccgcgac      1320
attcaagaca cctgtttttg ccatcgacga gcaccagatg tgggtatacg aagcagacgg      1380
gcaattcatc gagccccaaa aggttgacac ggtcaaaatt tacgccggcg agcggtactc      1440
agccatggtc aaactgacgg ggaaaccggg tcgcgactac accatccgtg tgatggacag      1500
cggcctgacc cagatcattg ggtcgtacgc cacgctgcgc tacaaatcgg ggaccggcga      1560
tgaagatggg gaaggtcgg tactcagtca gggcgttctc aactacgcg ggctcaacac        1620 aacgcaagtt gtcactctcg atcgaaatca cctgcctcca taccctccca cggcacccgc     1680
agaacacgcg gattctcttt atctcctcga cacgcatcgc gtgaagcacg cctggacgta     1740
taccatgaag ggcggggcga tgtacgaaga ggatcgtagt gcatatgcac cgctgctcta     1800
ctatcccgac tccgccgacg cactggacga gagtcttgtg atccgcacca agaacgacac     1860
gtggattgat cttgttgttc aggtcgggtc tctgcccgag cagccgcagg agtttcctca     1920
cgtcatgcac aaacattcag gcaaaacctg gcagattggc gccggggagg gacactggaa     1980
ctactcgtcg gtgaagagg cgatcaaggc agaaccgacc aagttcaacc tcaagaaccc      2040
caatttccgc gacaccttca tcacctcgtt cgatggccca tcgtggatag tgctgcggta     2100
ccactccaat aaccctgggc cttggttgat gcactgtcac tttgagattc atctgggtgg     2160
cggcatggcg attgcgatca tggacggtgt agatgcgtgg ccggaggtac cgccagagta     2220
cgcgccagac cagggaggat ttcccctctg a                                    2251
```

<210> SEQ ID NO 4
<211> LENGTH: 610
<212> TYPE: PRT
<213> ORGANISM: Malbranchea cinnamomea

<400> SEQUENCE: 4

Met Cys Asp Ser Arg Val Pro Val Thr Leu Ala Leu Val Val Phe
1               5                   10                  15

Ala Val Thr Thr Gly Met Ala Thr Ala Lys Leu Val Gln Glu Glu Leu
            20                  25                  30

Thr Leu Thr Trp Ser Val Gly Ala Pro Asn Gly Gln Pro Arg Glu Met
        35                  40                  45

Ile Phe Met Asn Gly Glu Phe Pro Gly Pro Thr Phe Met Trp Asp Glu
    50                  55                  60

Asp Asp Asp Ile Glu Val Thr Val His Asn Arg Met Pro Phe Asn Thr
65                  70                  75                  80

Thr Ile His Trp His Gly Leu Leu Met Gln Gly Thr Pro Trp Ser Asp
                85                  90                  95

Gly Val Pro Gly Leu Thr Gln Lys Pro Ile Glu Pro Gly Ala Ser Phe
            100                 105                 110

Ile Tyr Arg Phe Lys Ala Tyr Pro Ser Gly Thr His Trp Trp His Ser
        115                 120                 125

His Ser Arg Thr Thr Leu Leu Asp Gly Leu Tyr Gly Ala Leu Tyr Ile
    130                 135                 140

Arg Pro Lys Pro Ser Lys Pro Ser Pro Trp His Leu Ile Ser Asn Asp
145                 150                 155                 160

```
Glu Thr Asp Ile Ala Ser Met Gln Lys Ala Val Ala Asp Pro Lys Val
                165                 170                 175

Ile Val Ile Ser Asp Trp Thr Gln Phe Lys Ser Trp Glu Tyr Met Glu
            180                 185                 190

Ala Gln Ala Asn Ser Gly Tyr Thr Ile Phe Cys Val Asp Ser Leu Leu
        195                 200                 205

Ile Asn Gly Lys Gly Ser Val Tyr Cys Pro Gly Glu Asp Phe Leu Val
    210                 215                 220

Asn Leu Thr Ser Asn Tyr Met Lys Trp Ala Ile Tyr Pro Arg His Val
225                 230                 235                 240

Asn Asp Lys Gly Cys Leu Pro Phe Val Lys Ser Thr Glu Asn Lys Tyr
            245                 250                 255

Leu Lys Gly Gly Arg Pro Glu Thr Ile Pro Leu His Leu Gln Gln Gly
        260                 265                 270

Cys Val Pro Ser Glu Gly Asp Arg Thr Ile Ile Glu Val Asp Pro Ala
    275                 280                 285

Asp Gly Trp Val Ser Leu Asn Phe Val Asp Ala Ala Thr Phe Lys Thr
290                 295                 300

Pro Val Phe Ala Ile Asp Glu His Gln Met Trp Val Tyr Glu Ala Asp
305                 310                 315                 320

Gly Gln Phe Ile Glu Pro Gln Lys Val Asp Thr Val Lys Ile Tyr Ala
            325                 330                 335

Gly Glu Arg Tyr Ser Ala Met Val Lys Leu Thr Gly Lys Pro Gly Arg
        340                 345                 350

Asp Tyr Thr Ile Arg Val Met Asp Ser Gly Leu Thr Gln Ile Ile Gly
    355                 360                 365

Ser Tyr Ala Thr Leu Arg Tyr Lys Ser Gly Thr Gly Asp Glu Asp Gly
    370                 375                 380

Glu Arg Ser Val Leu Ser Gln Gly Val Leu Asn Tyr Gly Gly Leu Asn
385                 390                 395                 400

Thr Thr Gln Val Val Thr Leu Asp Arg Asn His Leu Pro Pro Tyr Pro
            405                 410                 415

Pro Thr Ala Pro Ala Glu His Ala Asp Ser Leu Tyr Leu Leu Asp Thr
        420                 425                 430

His Arg Val Lys His Ala Trp Thr Tyr Thr Met Lys Gly Gly Ala Met
    435                 440                 445

Tyr Glu Glu Asp Arg Ser Ala Tyr Ala Pro Leu Leu Tyr Tyr Pro Asp
450                 455                 460

Ser Ala Asp Ala Leu Asp Glu Ser Leu Val Ile Arg Thr Lys Asn Asp
465                 470                 475                 480

Thr Trp Ile Asp Leu Val Val Gln Val Gly Ser Leu Pro Glu Gln Pro
            485                 490                 495

Gln Glu Phe Pro His Val Met His Lys His Ser Gly Lys Thr Trp Gln
        500                 505                 510

Ile Gly Ala Gly Glu Gly His Trp Asn Tyr Ser Ser Val Glu Glu Ala
    515                 520                 525

Ile Lys Ala Glu Pro Thr Lys Phe Asn Leu Lys Asn Pro Asn Phe Arg
    530                 535                 540

Asp Thr Phe Ile Thr Ser Phe Asp Gly Pro Ser Trp Ile Val Leu Arg
545                 550                 555                 560

Tyr His Ser Asn Asn Pro Gly Pro Trp Leu Met His Cys His Phe Glu
            565                 570                 575
```

```
Ile His Leu Gly Gly Gly Met Ala Ile Ala Ile Met Asp Gly Val Asp
            580                 585                 590

Ala Trp Pro Glu Val Pro Pro Glu Tyr Ala Pro Asp Gln Gly Gly Phe
        595                 600                 605

Pro Leu
    610

<210> SEQ ID NO 5
<211> LENGTH: 2138
<212> TYPE: DNA
<213> ORGANISM: Malbranchea cinnamomea

<400> SEQUENCE: 5
```

| | | | | | |
|---|---|---|---|---|---|
| atgtatctgt | ccaaggaatt | cttctttgtc | caattggtct | tgtccttagc | agggggcagta | 60 |
| ccagctcctc | agcctggcct | gacctcgaat | gaacggcgga | gcccgtgtgg | gcattctgct | 120 |
| acatcgaggg | actgctgggg | agagtacagc | attgagaccg | actataccac | tgtggtgcct | 180 |
| gataccggtg | tggtcaggga | ggtactaaga | actcgttgaa | ttaatacggc | aagagtggtc | 240 |
| cgcgttctct | gcttatacct | tgtgattact | agtactggct | ggctgcgcag | aatatcactc | 300 |
| ttgcacctga | tggctattcg | cgccctgttc | ttgttttcaa | tgggacctat | ccggtccct | 360 |
| tgatagaagc | gaactggggc | gatacccttg | ttattcacgt | taaaaatgaa | atgcaacata | 420 |
| atgggttcgt | cgaaaatcta | cactttgatt | gatcgagact | gaataatcat | ccccttacgc | 480 |
| tgacatctgt | cctttgatgc | tagcaccgcg | gttcattggc | acggcatacg | ccaactcaac | 540 |
| tccaacagcg | aggatggtac | gttagtcgtg | attccaggag | agagatttga | ctgaatgatc | 600 |
| ccttcctaac | tcgagttcgc | aaggtgtccc | cggtactacg | caatgtccaa | ttgcccctgg | 660 |
| agagacaaga | acgtataaat | tccgtgccac | gcaatacggc | actgcatggt | accattctca | 720 |
| cttcagctct | cagctgggtg | atggtctata | cggccccttg | ataatccatg | gtccggctac | 780 |
| cgccaactac | gaccttgatc | tggggcccgt | ctttgtcact | gagtggttcc | atgacacctc | 840 |
| attcgtgctc | tgggagaggc | acaacaaaca | cggcggtttt | ccggtgaggc | caaactccgt | 900 |
| agcggataat | ggtttgatca | acggaaccaa | tgtgttctct | tgtgataagt | cggaggatcc | 960 |
| ggcatgcaaa | ggaacaggaa | aaagatccga | aaccacattc | atcccgggca | aaaagcatcg | 1020 |
| aattcgagtg | attgactcgc | aggttgatgg | atggatgcgc | ttttccattg | ataaccacaa | 1080 |
| actcactgtc | attgctgctg | atttggtgcc | aattgttccc | tatgagacag | aaagcatcat | 1140 |
| tctagcgccc | gggcagcggt | acgatgtgat | agtcgaggca | aatcaggaaa | ttggaaacta | 1200 |
| ctggatgaga | gctatctacc | agacgggatg | caatggcctc | aggattcata | caacgacat | 1260 |
| tcgtgccatt | gttcgatacg | aaggatccag | caaagaagac | cccacgacta | aacaatggga | 1320 |
| ctccattgac | gacaagtgca | agatgagcc | ctacgacaaa | ttattccat | acgtaaagaa | 1380 |
| ggatgtcgga | gcggctcacg | acaagagcca | actgaacatt | ggctggttct | atgaatggga | 1440 |
| cttggtcttc | cactggtcag | tcggcgggaa | agcgctaacc | ttggactggg | gcaatccaac | 1500 |
| gaacctgatg | attcacaaca | atgccacgga | tttcccaagg | gattacaacg | tctacaaaat | 1560 |
| cccgaccaaa | gatactgtac | gtaagacttg | aggctcgtgt | cattcctgat | acgctttacg | 1620 |
| aaggctttgt | taacttgcga | gcagtggacg | tactgggtta | tccaggattt | cacgtttgtc | 1680 |
| aacgcttacc | atcctttcca | cctccacggc | cacgacttcc | acatcttggc | tcaaggaaga | 1740 |
| ggcctttta | cacccttgac | agtcaaacta | accgcaagaa | accctcctcg | ccgtgacaca | 1800 |
| gcgacgctac | ttggcgccgg | ttaccttgtt | attgcttttg | aaagtgataa | tccagggtaa | 1860 |

-continued

```
ggggtcgccc accttttctg tccctgtgca tcaatgaaat gagctccgta taacttgaac    1920
agaaggactg actgaatgag tacgtatgca gatcgtggct catgcactgt catattgcct    1980
ggcatgcggg ccagagtatg cactccaat tcattgagcg agaggagaa ataccagcct      2040 tgatcaatcc gggtatggat gagttcaaac aggcgtgtgc caagtgggat gaatactacg    2100
caactgcccc ttacaagcaa gacgactcgg gaatctaa                            2138
```

<210> SEQ ID NO 6
<211> LENGTH: 585
<212> TYPE: PRT
<213> ORGANISM: Malbranchea cinnamomea

<400> SEQUENCE: 6

```
Met Tyr Leu Ser Lys Glu Phe Phe Val Gln Leu Val Leu Ser Leu
1               5                   10                  15

Ala Gly Ala Val Pro Ala Pro Gln Pro Gly Leu Thr Ser Asn Glu Arg
                20                  25                  30

Arg Ser Pro Cys Gly His Ser Ala Thr Ser Arg Asp Cys Trp Gly Glu
            35                  40                  45

Tyr Ser Ile Glu Thr Asp Tyr Thr Thr Val Val Pro Asp Thr Gly Val
50                  55                  60

Val Arg Glu Tyr Trp Leu Ala Ala Gln Asn Ile Thr Leu Ala Pro Asp
65                  70                  75                  80

Gly Tyr Ser Arg Pro Val Leu Val Phe Asn Gly Thr Tyr Pro Gly Pro
                85                  90                  95

Leu Ile Glu Ala Asn Trp Gly Asp Thr Leu Val Ile His Val Lys Asn
            100                 105                 110

Glu Met Gln His Asn Gly Thr Ala Val His Trp His Gly Ile Arg Gln
        115                 120                 125

Leu Asn Ser Asn Ser Glu Asp Gly Val Pro Gly Thr Thr Gln Cys Pro
130                 135                 140

Ile Ala Pro Gly Glu Thr Arg Thr Tyr Lys Phe Arg Ala Thr Gln Tyr
145                 150                 155                 160

Gly Thr Ala Trp Tyr His Ser His Phe Ser Ser Gln Leu Gly Asp Gly
                165                 170                 175

Leu Tyr Gly Pro Leu Ile Ile His Gly Pro Ala Thr Ala Asn Tyr Asp
            180                 185                 190

Leu Asp Leu Gly Pro Val Phe Val Thr Glu Trp Phe His Asp Thr Ser
        195                 200                 205

Phe Val Leu Trp Glu Arg His Asn Lys His Gly Phe Pro Val Arg
210                 215                 220

Pro Asn Ser Val Ala Asp Asn Gly Leu Ile Asn Gly Thr Asn Val Phe
225                 230                 235                 240

Ser Cys Asp Lys Ser Glu Asp Pro Ala Cys Lys Gly Thr Gly Lys Arg
                245                 250                 255

Ser Glu Thr Thr Phe Ile Pro Gly Lys Lys His Arg Ile Arg Val Ile
            260                 265                 270

Asp Ser Gln Val Asp Gly Trp Met Arg Phe Ser Ile Asp Asn His Lys
        275                 280                 285

Leu Thr Val Ile Ala Ala Asp Leu Val Pro Ile Val Pro Tyr Glu Thr
290                 295                 300

Glu Ser Ile Ile Leu Ala Pro Gly Gln Arg Tyr Asp Val Ile Val Glu
305                 310                 315                 320

Ala Asn Gln Glu Ile Gly Asn Tyr Trp Met Arg Ala Ile Tyr Gln Thr
```

```
              325                 330                 335
Gly Cys Asn Gly Leu Arg Ile His Asn Asn Asp Ile Arg Ala Ile Val
            340                 345                 350

Arg Tyr Glu Gly Ser Ser Lys Glu Asp Pro Thr Thr Lys Gln Trp Asp
        355                 360                 365

Ser Ile Asp Asp Lys Cys Lys Asp Glu Pro Tyr Asp Lys Leu Ile Pro
    370                 375                 380

Tyr Val Lys Lys Asp Val Gly Ala Ala His Asp Lys Ser Gln Leu Asn
385                 390                 395                 400

Ile Gly Trp Phe Tyr Glu Trp Asp Leu Val Phe His Trp Ser Val Gly
                405                 410                 415

Gly Lys Ala Leu Thr Leu Asp Trp Gly Asn Pro Thr Asn Leu Met Ile
            420                 425                 430

His Asn Asn Ala Thr Asp Phe Pro Arg Asp Tyr Asn Val Tyr Lys Ile
        435                 440                 445

Pro Thr Lys Asp Thr Trp Thr Tyr Trp Val Ile Gln Asp Phe Thr Phe
    450                 455                 460

Val Asn Ala Tyr His Pro Phe His Leu His Gly His Asp Phe His Ile
465                 470                 475                 480

Leu Ala Gln Gly Arg Gly Leu Phe Thr Pro Leu Thr Val Lys Leu Asn
                485                 490                 495

Arg Lys Asn Pro Pro Arg Arg Asp Thr Ala Thr Leu Leu Gly Ala Gly
            500                 505                 510

Tyr Leu Val Ile Ala Phe Glu Ser Asp Asn Pro Gly Ser Trp Leu Met
        515                 520                 525

His Cys His Ile Ala Trp His Ala Gly Gln Ser Met Ala Leu Gln Phe
    530                 535                 540

Ile Glu Arg Glu Gly Glu Ile Pro Ala Leu Ile Asn Pro Gly Met Asp
545                 550                 555                 560

Glu Phe Lys Gln Ala Cys Ala Lys Trp Asp Glu Tyr Tyr Ala Thr Ala
                565                 570                 575

Pro Tyr Lys Gln Asp Asp Ser Gly Ile
            580                 585

<210> SEQ ID NO 7
<211> LENGTH: 1889
<212> TYPE: DNA
<213> ORGANISM: Rhizomucor pusillus

<400> SEQUENCE: 7
atgtggtcac tgtattgtat actgctacta ctcgttggcc tgctacagca tccatatctt      60
gcatatgcaa gagagcgcac ctacgaaata gatctcacct gggtgaggt gaatccggac      120 tgttaccaag agtcttacac tcgtctgctt gtcaataacc aatttcctgc accacctatc     180
cgcgtcgcac gaaatgacaa ggttcgcatc atcgtcagaa actctatcga caccggcatg     240
cctgcaacaa ttcactatca tggcatcatg cagatcggca gcacagaaat ggatggtatg     300
cccaacgtta cccaagtcgc tattcagcct ggagaggaat tccaccacga attcagggtc     360
atcaaccaat caggcactta cttttaccac gctcacgtca actttcaaga taattcggta     420
tttgggcctt tcattgtata cgaagacaag gaatcttggc cttcagatag caagcatcca     480
aaatctctgc gcgatggtcc gtacttgtat catgacgagc ggatcataat gctatccgag     540
tggtggcatc aatctgaaca gaacaactc gactatgtct ttgggcccaa atatcgagga     600
atgataccag cacatagcta tctcattaac ggccggaccg tttacgatcc ttcaaatgta     660
```

```
accgatgaca cccactgcga aggttactcc gcgatcgatg tcgaacccgg caaaacatat    720
cgattgcgta ttataggatc tacaagcttc gccacacttg gatttgctat cgccaagcat    780
acaatgacag ttatcgaggt cgatggcggt ctcattaagc catatcgaac atcctacctg    840
gaagttgcat ctggacagcg attctccgtt ctcgttacgg cagaccagcc tcctgacagc    900
tatcttatca gcacgcgcac atactgggta gactacgcag ttgacaggaa tggtctggct    960
gttttccggt acaccaacga gcggccatac aggcaccaac gtgctcgtca cgactttgaa   1020
ccttatcgcc gcggacctgt ctccaaaccc caaatctttt cggcgacagc aagcaatgca   1080
agcaatccag aaatgtttgc cttccctcct gccaaaaatg aatggttctt ccggaatttt   1140
gagccccttg acagtcctga ccacgatttc acctctccgc cggatcgcac cgttgttctc   1200
actcctatcg aacgccgatt gccggacggt actgtccgct ggtttatcaa cgaacacgaa   1260
ccgccaacgt gggatgtgcc gctgctaacc cagctagcgc agctgaaaag aatagctgtc   1320
aacgagacag cagtgcactt gaacaggcaa tctatcctat ttgatggcta cgatcatttc   1380
aagcaagtat accctgtcat gtacaacgaa gttatcgact ttgtcataca aactaccact   1440
ttggaaggca ttggtatctg cgccggacac ccttggcaca cgcacggcta ttctcactac   1500
accattgcgc acggaccagg tgaatatgtc caccagcgcg acaaggatat ccggacatac   1560
aataacccca ttcccaaagt tagttttgca acctttttgat tgagcagtgc cttgagctaa   1620
caactgttac ctccttagga tatcacattt gtgtatcctg tgcaacctgc cgtgaatgct   1680
tcaggtatcc catgtggctg gacgaaaatt cgcatgttca tcgtaagtaa aagccgggct   1740
tgagctttca gcgacatttc tgacagtgga ttgcatagac gaatccggga ctgtgggcct   1800
tccattgcca catcactggt catatgttgc aaggcatgat aacagtcctt gaggctgcac   1860
cagagatgat tccgtacctt caaaagtaa                                      1889
```

<210> SEQ ID NO 8
<211> LENGTH: 590
<212> TYPE: PRT
<213> ORGANISM: Rhizomucor pusillus
<400> SEQUENCE: 8

```
Met Trp Ser Leu Tyr Cys Ile Leu Leu Leu Val Gly Leu Leu Gln
1               5                   10                  15

His Pro Tyr Leu Ala Tyr Ala Arg Glu Arg Thr Tyr Glu Ile Asp Leu
            20                  25                  30

Thr Leu Gly Glu Val Asn Pro Asp Cys Tyr Gln Glu Ser Tyr Thr Arg
        35                  40                  45

Leu Leu Val Asn Asn Gln Phe Pro Ala Pro Ile Arg Val Ala Arg
    50                  55                  60

Asn Asp Lys Val Arg Ile Ile Val Arg Asn Ser Ile Asp Thr Gly Met
65                  70                  75                  80

Pro Ala Thr Ile His Tyr His Gly Ile Met Gln Ile Gly Ser Thr Glu
                85                  90                  95

Met Asp Gly Met Pro Asn Val Thr Gln Val Ala Ile Gln Pro Gly Glu
            100                 105                 110

Glu Phe His His Glu Phe Arg Val Ile Asn Gln Ser Gly Thr Tyr Phe
        115                 120                 125

Tyr His Ala His Val Asn Phe Gln Asp Asn Ser Val Phe Gly Pro Phe
    130                 135                 140

Ile Val Tyr Glu Asp Lys Glu Ser Trp Pro Ser Asp Ser Lys His Pro
```

-continued

```
            145                 150                 155                 160
        Lys Ser Leu Arg Asp Gly Pro Tyr Leu Tyr His Asp Glu Arg Ile Ile
                        165                 170                 175
        Met Leu Ser Glu Trp Trp His Gln Ser Glu Gln Gln Leu Asp Tyr
                        180                 185                 190
        Val Phe Gly Pro Lys Tyr Arg Gly Met Ile Pro Ala His Ser Tyr Leu
                        195                 200                 205
        Ile Asn Gly Arg Thr Val Tyr Asp Pro Ser Asn Val Thr Asp Asp Thr
                210                 215                 220
        His Cys Glu Gly Tyr Ser Ala Ile Asp Val Glu Pro Gly Lys Thr Tyr
        225                 230                 235                 240
        Arg Leu Arg Ile Ile Gly Ser Thr Ser Phe Ala Thr Leu Gly Phe Ala
                        245                 250                 255
        Ile Ala Lys His Thr Met Thr Val Ile Glu Val Asp Gly Gly Leu Ile
                        260                 265                 270
        Lys Pro Tyr Arg Thr Ser Tyr Leu Glu Val Ala Ser Gly Gln Arg Phe
                        275                 280                 285
        Ser Val Leu Val Thr Ala Asp Gln Pro Pro Asp Ser Tyr Leu Ile Ser
                290                 295                 300
        Thr Arg Thr Tyr Trp Val Asp Tyr Ala Val Asp Arg Asn Gly Leu Ala
        305                 310                 315                 320
        Val Phe Arg Tyr Thr Asn Glu Arg Pro Tyr Arg His Gln Arg Ala Arg
                        325                 330                 335
        His Asp Phe Glu Pro Tyr Arg Arg Gly Pro Val Ser Lys Pro Gln Ile
                        340                 345                 350
        Phe Ser Ala Thr Ala Ser Asn Ala Ser Asn Pro Glu Met Phe Ala Phe
                        355                 360                 365
        Pro Pro Ala Lys Asn Glu Trp Phe Phe Pro Glu Phe Glu Pro Leu Asp
                        370                 375                 380
        Ser Pro Asp His Asp Phe Thr Ser Pro Pro Asp Arg Thr Val Val Leu
        385                 390                 395                 400
        Thr Pro Ile Glu Arg Arg Leu Pro Asp Gly Thr Val Arg Trp Phe Ile
                        405                 410                 415
        Asn Glu His Glu Pro Pro Thr Trp Asp Val Pro Leu Leu Thr Gln Leu
                        420                 425                 430
        Ala Gln Leu Lys Arg Ile Ala Val Asn Glu Thr Ala Val His Leu Asn
                        435                 440                 445
        Arg Gln Ser Ile Leu Phe Asp Gly Tyr Asp His Phe Lys Gln Val Tyr
                        450                 455                 460
        Pro Val Met Tyr Asn Glu Val Ile Asp Phe Val Ile Gln Thr Thr Thr
        465                 470                 475                 480
        Leu Glu Gly Ile Gly Ile Cys Ala Gly His Pro Trp His Thr His Gly
                        485                 490                 495
        Tyr Ser His Tyr Thr Ile Ala His Gly Pro Gly Glu Tyr Val His Gln
                        500                 505                 510
        Arg Asp Lys Asp Ile Arg Thr Tyr Asn Asn Pro Ile Pro Lys Asp Ile
                        515                 520                 525
        Thr Phe Val Tyr Pro Val Gln Pro Ala Val Asn Ala Ser Gly Ile Pro
                        530                 535                 540
        Cys Gly Trp Thr Lys Ile Arg Met Phe Ile Thr Asn Pro Gly Leu Trp
        545                 550                 555                 560
        Ala Phe His Cys His Ile Thr Gly His Met Leu Gln Gly Met Ile Thr
                        565                 570                 575
```

```
Val Leu Glu Ala Ala Pro Glu Met Ile Pro Tyr Leu Gln Lys
        580                 585                 590

<210> SEQ ID NO 9
<211> LENGTH: 2079
<212> TYPE: DNA
<213> ORGANISM: Rhizomucor pusillus

<400> SEQUENCE: 9
atgaagactt actgcgcact cttgttgctg acattcttct ggatgtttgg ccaaagctct      60
cctactccat cctgcaatca gcatcgtcct gaagagaaca ttcgcttcta cgagctgaat     120
attacgcgtg aaatactcaa tccggactgc tctacctacc acggacccaa actggtcgtc     180
aatagccagt tgccgggacc tcccatcaag ttaatagcag gcgagcgggt gcgtgtgctg     240
gtccgtaatt tgcttccaaa acacagtgaa ggcgccatca gtgacaaaaa taggcacacc     300
attgacaaca atgttaccgc tacaagcagc gattcccaat tctttcaaga ttcagctatg     360
ggtggttcat ctaatgatat cagcattcat ttccatggga tccgacaaaa cggttcggtg     420
gatgcagatg gcgtgccatt cctcactcaa aagccgatac ctcccggagg cgagcttctc     480
caagaattcc aagtgattgg acaatcaggc acttatttct atcacgcgca cgttggtacc     540
tcggttgaaa cggtgtttgg tccattgata gtctacgaat ccaaggatgc tgagccgccg     600
cagcagcatg ctgacaacaa caagaggaag aagaagactg ctaagcttac ggctggaccg     660
tacacgtatg acgaggaccg catacttatg atcagcgaat actggcaccg cacgcagcaa     720
gagtttgaag actatatact tggccctaac tttgctggta tcccggaagc tgacagcatt     780
ctcatcaatg gacgcactat cttttaatatt tcagatatct acaagtcaga aatgtgccct     840
ggttaccctg taatacaagt cgagcctggc aagacatata gactccgtgt gattggagcc     900
actgctttcc gaacggttgg tctcgctata gcaccacca gttgacggt cattgaagtg     960 gacggcgagc ttgtcgaacc atacaaggtg gattatcttg aagtgactgc cgggcagcga    1020
ttctcggtgc tgttggaagc caaccagcag cagcagcagg aggaggcaac tggcaaaaag    1080
gactttacta tttccaccat caggatgtgg gctgaaggcg tgaatcctgc ttcgaatggg    1140
tttgctgtgc ttcgatacac gtgcagcaat gatgccaaga atctgatatc accaccatca    1200
tctcacgagc ttgtcctcac acccaacaat aaattcaatg ttttccaca gcaagatatt    1260 attcagtggc aatggttaca catgaagccg gtccatcaca gccctatcct cgatgccaaa    1320
cccgaccgaa ctgtcatact acgcgtcacc gagggcaatc tagataacgg cggtaaccgt    1380
tggttcataa acggcattag tttcatggat cccaagcaag ttatcttgga acaaattttg    1440
cgtcaagaac ggaaggcgcc catagagata accgcaacgt cctccggata cgatccatat    1500
cttggaactt acccttgaa atacaacgaa gtggtcgact tgttctgca gtcgacgcat    1560 cttcccaaga caccctgccg aagtcatcca tggcatatgc acggtcacac cttttacgaa    1620
atcgcctacg gcccaggcga ctatgatgaa aaacgggacg ggaacttgcg caacgtaccc    1680
aatcctatcg gcagggatgt taccttggtc taccccatct tggatcctgc tttggaacgc    1740
aacaacgcaa cagccaacac ccaagtcgga tgcggctgga gcaagatccg cataattgct    1800
gtaagtctgc cattcttcgt ctttttcagaa acagtgtggt gctaatatgt agcttttggt    1860
cgcatacctt tttaggacaa tcccggtatc tgtaagtatc gtacacgaac caaaagcgac    1920
acgaacttta gactcatgtt atatgctgta ggggcaatgc actgccacaa taccgtacat    1980
atgctcatgg gcatgatggt tgctctagaa gaagcgcctg aaatcattcc cgtggctctc    2040
```
cagcaacaac gacaatactc gtcagcgaga atcaagtag 2079

<210> SEQ ID NO 10
<211> LENGTH: 617
<212> TYPE: PRT
<213> ORGANISM: Rhizomucor pusillus

<400> SEQUENCE: 10

| | | | | | | | | | | | | | | |
|---|---|---|---|---|---|---|---|---|---|---|---|---|---|---|
| Met | Lys | Thr | Tyr | Cys | Ala | Leu | Leu | Leu | Thr | Phe | Phe | Trp | Met | Phe |
| 1 | | | | 5 | | | | | 10 | | | | | 15 |
| Gly | Gln | Ser | Ser | Pro | Thr | Pro | Ser | Cys | Asn | Gln | His | Arg | Pro | Glu | Glu |
| | | | 20 | | | | | 25 | | | | | 30 | | |
| Asn | Ile | Arg | Phe | Tyr | Glu | Leu | Asn | Ile | Thr | Arg | Glu | Ile | Leu | Asn | Pro |
| | | 35 | | | | | 40 | | | | | 45 | | | |
| Asp | Cys | Ser | Thr | Tyr | His | Gly | Pro | Lys | Leu | Val | Val | Asn | Ser | Gln | Leu |
| 50 | | | | | 55 | | | | | 60 | | | | | |
| Pro | Gly | Pro | Pro | Ile | Lys | Leu | Ile | Ala | Gly | Glu | Arg | Val | Arg | Val | Leu |
| 65 | | | | 70 | | | | | 75 | | | | | 80 | |
| Val | Arg | Asn | Leu | Leu | Pro | Lys | His | Thr | Met | Gly | Gly | Ser | Ser | Asn | Asp |
| | | | | 85 | | | | | 90 | | | | | 95 | |
| Ile | Ser | Ile | His | Phe | His | Gly | Ile | Arg | Gln | Asn | Gly | Ser | Val | Asp | Ala |
| | | | 100 | | | | | 105 | | | | | 110 | | |
| Asp | Gly | Val | Pro | Phe | Leu | Thr | Gln | Lys | Pro | Ile | Pro | Gly | Gly | Glu |
| | | 115 | | | | | 120 | | | | | 125 | | | |
| Leu | Leu | Gln | Glu | Phe | Gln | Val | Ile | Gly | Gln | Ser | Gly | Thr | Tyr | Phe | Tyr |
| | 130 | | | | | 135 | | | | | 140 | | | | |
| His | Ala | His | Val | Gly | Thr | Ser | Val | Glu | Thr | Val | Phe | Gly | Pro | Leu | Ile |
| 145 | | | | | 150 | | | | | 155 | | | | | 160 |
| Val | Tyr | Glu | Ser | Lys | Asp | Ala | Glu | Pro | Pro | Gln | Gln | His | Ala | Asp | Asn |
| | | | | 165 | | | | | 170 | | | | | 175 | |
| Asn | Lys | Arg | Lys | Lys | Lys | Thr | Ala | Lys | Leu | Thr | Ala | Gly | Pro | Tyr | Thr |
| | | | 180 | | | | | 185 | | | | | 190 | | |
| Tyr | Asp | Glu | Asp | Arg | Ile | Leu | Met | Ile | Ser | Glu | Tyr | Trp | His | Arg | Thr |
| | | 195 | | | | | 200 | | | | | 205 | | | |
| Gln | Gln | Glu | Phe | Glu | Asp | Tyr | Ile | Leu | Gly | Pro | Asn | Phe | Ala | Gly | Ile |
| | 210 | | | | | 215 | | | | | 220 | | | | |
| Pro | Glu | Ala | Asp | Ser | Ile | Leu | Ile | Asn | Gly | Arg | Thr | Ile | Phe | Asn | Ile |
| 225 | | | | | 230 | | | | | 235 | | | | | 240 |
| Ser | Asp | Ile | Tyr | Lys | Ser | Glu | Met | Cys | Pro | Gly | Tyr | Pro | Val | Ile | Gln |
| | | | | 245 | | | | | 250 | | | | | 255 | |
| Val | Glu | Pro | Gly | Lys | Thr | Tyr | Arg | Leu | Arg | Val | Ile | Gly | Ala | Thr | Ala |
| | | | 260 | | | | | 265 | | | | | 270 | | |
| Phe | Arg | Thr | Val | Gly | Leu | Ala | Ile | Ala | His | His | Lys | Leu | Thr | Val | Ile |
| | | 275 | | | | | 280 | | | | | 285 | | | |
| Glu | Val | Asp | Gly | Glu | Leu | Val | Glu | Pro | Tyr | Lys | Val | Asp | Tyr | Leu | Glu |
| | 290 | | | | | 295 | | | | | 300 | | | | |
| Val | Thr | Ala | Gly | Gln | Arg | Phe | Ser | Val | Leu | Leu | Glu | Ala | Asn | Gln | Gln |
| 305 | | | | | 310 | | | | | 315 | | | | | 320 |
| Gln | Gln | Gln | Glu | Glu | Ala | Thr | Gly | Lys | Lys | Asp | Phe | Thr | Ile | Ser | Thr |
| | | | | 325 | | | | | 330 | | | | | 335 | |
| Ile | Arg | Met | Trp | Ala | Glu | Gly | Val | Asn | Pro | Ala | Ser | Asn | Gly | Phe | Ala |
| | | | 340 | | | | | 345 | | | | | 350 | | |
| Val | Leu | Arg | Tyr | Thr | Cys | Ser | Asn | Asp | Ala | Lys | Asn | Leu | Ile | Ser | Pro |
| | | 355 | | | | | 360 | | | | | 365 | | | |

```
Pro Ser Ser His Glu Leu Val Leu Thr Pro Asn Asn Lys Phe Asn Gly
        370                 375                 380

Phe Pro Gln Gln Asp Ile Ile Gln Trp Gln Trp Leu His Met Lys Pro
385                 390                 395                 400

Val His His Ser Pro Ile Leu Asp Ala Lys Pro Asp Arg Thr Val Ile
                405                 410                 415

Leu Arg Val Thr Glu Gly Asn Leu Asp Asn Gly Gly Asn Arg Trp Phe
                420                 425                 430

Ile Asn Gly Ile Ser Phe Met Asp Pro Lys Gln Val Ile Leu Glu Gln
            435                 440                 445

Ile Leu Arg Gln Glu Arg Lys Ala Pro Ile Glu Ile Thr Ala Thr Ser
        450                 455                 460

Ser Gly Tyr Asp Pro Tyr Leu Gly Thr Tyr Pro Leu Lys Tyr Asn Glu
465                 470                 475                 480

Val Val Asp Phe Val Leu Gln Ser Thr His Leu Pro Lys Thr Pro Cys
                485                 490                 495

Arg Ser His Pro Trp His Met His Gly His Thr Phe Tyr Glu Ile Ala
                500                 505                 510

Tyr Gly Pro Gly Asp Tyr Asp Glu Lys Arg Asp Gly Asn Leu Arg Asn
            515                 520                 525

Val Pro Asn Pro Ile Gly Arg Asp Val Thr Leu Val Tyr Pro Ile Leu
530                 535                 540

Asp Pro Ala Leu Glu Arg Asn Asn Ala Thr Ala Asn Thr Gln Val Gly
545                 550                 555                 560

Cys Gly Trp Ser Lys Ile Arg Ile Ile Ala Asp Asn Pro Gly Ile Trp
                565                 570                 575

Ala Met His Cys His Asn Thr Val His Met Leu Met Gly Met Met Val
                580                 585                 590

Ala Leu Glu Glu Ala Pro Glu Ile Ile Pro Val Ala Leu Gln Gln Gln
            595                 600                 605

Arg Gln Tyr Ser Ser Ala Arg Ile Lys
        610                 615

<210> SEQ ID NO 11
<211> LENGTH: 1791
<212> TYPE: DNA
<213> ORGANISM: Rhizomucor pusillus

<400> SEQUENCE: 11
atgtcacata ttttcaact  aatacacttt  ctcgcgttac  tgtgcctttt  attacactct     60
gccaaagcag acaaggtgtt  cgaacttaac  attacaacaa  caagcaatac  attcaatcct    120
gattgctcgg actatatttc  ctcgtctgca  ttgttggtca  atggccagct  tcctggacct    180
cccattaaag tgactcgagg  agaacgcgtc  cagatcaccg  ttcgaaacat  gctgtccgag    240
aatataacaa gtgaacacgc  cgcaatacat  taccacggta  tccggcagta  cggcagcaac    300
tttgcagacg gagtccccctt tctgacgcag  catccgatcc  accgggccca  agagtttaca    360
cacgactttc gagtcgttaa  ccaggctggc  acatactttt  accacgccca  cgttggattg    420
caagaggaaa ccgtgtttgg  agcatttatt  gtatacgaca  gcgattcgga  aaataataac    480
aaaaaactca tggatggtcc  ctacgagtac  gacgatgaac  gtattatcat  gctgagcgaa    540
tggtggcatc gcccgcgcaa  ccagtttgaa  gatttcctac  tgggacccca  gttcgacttt    600
atacccgaag ctgacagcgt  acttgtcaac  ggccaaacca  tacacgatcc  caaaagtaaa    660
```

```
ctgtctaaag actgtaaggg ctactccatt gtacccgtcg acgcaggcaa gacataccgc    720
ttacgagtca ttggatcaac cacgtttcgt actctcgggt tcgctatcgc gcaccacaac    780
ctgacggtaa tcgaagtcga cggtgaactt gtcaagccgt acacagtacc gttcctcgaa    840
gtcactcccg gccagcgttt ctccgtcttg ctcaacacag atcaggcacc tcgcgactat    900
gctatacaga ccagcaggct gtgggcagaa ggcgtcgatt cgttctccaa tggatacgct    960
cttttgcgct acaacgtgcc caacaagatc tatccaaacc catccgtgac cttgccaccc   1020
atggatccac ccatacttgc caacgaagta ccgcactgga tatggtctga cttggaacct   1080
ctctacggcg ttgatccgat tgtcagcaga agcgcttcca ggaccatcaa acttcgctcc   1140
accgaagcac ggatgccaga cggtacctcg cggtggttca tcaacggcgt ttcgtttacc   1200
gaacctggat cgcctatttt acatgatatc taccgacgca ctcgacggct cccggaaacc   1260
taccacgcac aaggctacga tgcgatgcta ggaacatatc cgatcaaata ctacgaggtg   1320
gttgactttg tgctgcaggc gacgcacaaa ccaggtgagc catgccgaac ccacccttgg   1380
catacacacg gacactccca ctgggaaatc gcacatggtc ctggcgagta cgacgagcaa   1440
cgtgatcgaa atatacgcaa tgtgcctagc ccggtttatc gtgatatcac tctaacctac   1500
ccagagttgg accctgaact cgaggatccc aacgggcccc acgcaaacga agtagtcgga   1560
tgcgggtgga caaaaatccg catcattgct gtaagttgat attcgaatat atgcaagacg   1620
gaaaactaat ttagatatgg atattttag gataatccag gtgtttgggc catgcattgc   1680
cacaatacgc cacacatgct gatgggcatg atggtcgcct tggaagaagc tccagaaatg   1740
atacaagcgc cgtacatatc ttccccacag catccggtcg caaaatcata a            1791
```

<210> SEQ ID NO 12
<211> LENGTH: 576
<212> TYPE: PRT
<213> ORGANISM: Rhizomucor pusillus

<400> SEQUENCE: 12

```
Met Ser His Ile Phe Gln Leu Ile His Phe Leu Ala Leu Leu Cys Leu
1               5                   10                  15

Leu Leu His Ser Ala Lys Ala Asp Lys Val Phe Glu Leu Asn Ile Thr
            20                  25                  30

Thr Thr Ser Asn Thr Phe Asn Pro Asp Cys Ser Asp Tyr Ile Ser Ser
        35                  40                  45

Ser Ala Leu Leu Val Asn Gly Gln Leu Pro Gly Pro Pro Ile Lys Val
    50                  55                  60

Thr Arg Gly Glu Arg Val Gln Ile Thr Val Arg Asn Met Leu Ser Glu
65                  70                  75                  80

Asn Ile Thr Ser Glu His Ala Ala Ile His Tyr His Gly Ile Arg Gln
                85                  90                  95

Tyr Gly Ser Asn Phe Ala Asp Gly Val Pro Phe Leu Thr Gln His Pro
            100                 105                 110

Ile Pro Pro Gly Gln Glu Phe Thr His Asp Phe Arg Val Val Asn Gln
        115                 120                 125

Ala Gly Thr Tyr Phe Tyr His Ala His Val Gly Leu Gln Glu Glu Thr
    130                 135                 140

Val Phe Gly Ala Phe Ile Val Tyr Asp Ser Asp Ser Glu Asn Asn Asn
145                 150                 155                 160

Lys Lys Leu Met Asp Gly Pro Tyr Glu Tyr Asp Glu Arg Ile Ile
                165                 170                 175
```

Met Leu Ser Glu Trp Trp His Arg Pro Arg Asn Gln Phe Glu Asp Phe
            180                 185                 190

Leu Leu Gly Pro Gln Phe Asp Phe Ile Pro Glu Ala Asp Ser Val Leu
        195                 200                 205

Val Asn Gly Gln Thr Ile His Asp Pro Lys Ser Lys Leu Ser Lys Asp
    210                 215                 220

Cys Lys Gly Tyr Ser Ile Val Pro Val Asp Ala Gly Lys Thr Tyr Arg
225                 230                 235                 240

Leu Arg Val Ile Gly Ser Thr Thr Phe Arg Thr Leu Gly Phe Ala Ile
                245                 250                 255

Ala His His Asn Leu Thr Val Ile Glu Val Asp Gly Glu Leu Val Lys
            260                 265                 270

Pro Tyr Thr Val Pro Phe Leu Glu Val Thr Pro Gly Gln Arg Phe Ser
        275                 280                 285

Val Leu Leu Asn Thr Asp Gln Ala Pro Arg Asp Tyr Ala Ile Gln Thr
    290                 295                 300

Ser Arg Leu Trp Ala Glu Gly Val Asp Ser Phe Ser Asn Gly Tyr Ala
305                 310                 315                 320

Leu Leu Arg Tyr Asn Val Pro Asn Lys Ile Tyr Pro Asn Pro Ser Val
                325                 330                 335

Thr Leu Pro Pro Met Asp Pro Ile Leu Ala Asn Glu Val Pro His
            340                 345                 350

Trp Ile Trp Ser Asp Leu Glu Pro Leu Tyr Gly Val Asp Pro Ile Val
        355                 360                 365

Ser Arg Ser Ala Ser Arg Thr Ile Lys Leu Arg Ser Thr Glu Ala Arg
    370                 375                 380

Met Pro Asp Gly Thr Ser Arg Trp Phe Ile Asn Gly Val Ser Phe Thr
385                 390                 395                 400

Glu Pro Gly Ser Pro Ile Leu His Asp Ile Tyr Arg Arg Thr Arg Arg
                405                 410                 415

Leu Pro Glu Thr Tyr His Ala Gln Gly Tyr Asp Ala Met Leu Gly Thr
            420                 425                 430

Tyr Pro Ile Lys Tyr Tyr Glu Val Val Asp Phe Val Leu Gln Ala Thr
        435                 440                 445

His Lys Pro Gly Glu Pro Cys Arg Thr His Pro Trp His Thr His Gly
    450                 455                 460

His Ser His Trp Glu Ile Ala His Gly Pro Gly Glu Tyr Asp Glu Gln
465                 470                 475                 480

Arg Asp Arg Asn Ile Arg Asn Val Pro Ser Pro Val Tyr Arg Asp Ile
                485                 490                 495

Thr Leu Thr Tyr Pro Glu Leu Asp Pro Glu Leu Glu Asp Pro Asn Gly
            500                 505                 510

Pro His Ala Asn Glu Val Val Gly Cys Gly Trp Thr Lys Ile Arg Ile
        515                 520                 525

Ile Ala Asp Asn Pro Gly Val Trp Ala Met His Cys His Asn Thr Pro
    530                 535                 540

His Met Leu Met Gly Met Met Val Ala Leu Glu Glu Ala Pro Glu Met
545                 550                 555                 560

Ile Gln Ala Pro Tyr Ile Ser Ser Pro Gln His Pro Val Ala Lys Ser
                565                 570                 575

<210> SEQ ID NO 13
<211> LENGTH: 2166
<212> TYPE: DNA

<213> ORGANISM: Penicillium emersonii

<400> SEQUENCE: 13

```
atggcgccaa aagggtcctt tctcacattg tgcctggccg ccttggccac ctcggcgtac      60
gccgccacgg tcccgttcga gcttcacttg acgtgggaag aaggggcccc agatggaaac     120
cccagaaaga tgattttcat gaatggccaa tttccggggc cagaattggt ggtggatgaa     180
ggtgatgatg tcgaggtttg tgttttttgtt tgttttttttc gaaatagata gtgtcgggaa     240
ctaattttgt tcaagttcct cgtccataat cacctgcctt tcaatacgtc gattcatttc     300
cacgggattg agtgcgtggg cagcctgtct ctgctgattt cgcaaaatga cagtactgac     360
aacagagaag gcagatgaac accccctggg ccgatggcgt cccgggactt acacagaaac     420
caattccgcc aggggaaagc tttctttacc gatggactgc cacgacttac gggacttact     480
ggtgagcacc atcttggcta cctgtcttag aagattacta gtactgacta gggctgtcca     540
ggtaccactc ccattacagc aacacaatgg ccgacggact gtacggcccc atttgggtca     600
ggtgtgtccc ccatatttcc cttgcgtgtt tggtttcaac taacctgtta ggccaaaccc     660
acatacacca accccgttcc atttgatctc gaatgatcca gcagatcttg aagccatgcg     720
gcgtgcagaa catgatcccc gactggtcgt gttatcggac tgggaacacc tgacctcgga     780
ggagtacttc aatttgcagc taattagcgg gctcgatgtt ttgtaagaac catgacctcg     840
acggggggaca tcgattagcg actaacgtgg aaatcccaaa acagttgcgt ggacagcatt     900
ctgatcaatg gaaaggagc agtccactgc ccaagtgcag aggaaattgc cagctacgaa     960
acgccctatc tgaaaggtgc cattgacaat ctgcctctta cggataaggg gtgagttcca    1020
gcgtaagccg aaagcgggga aattggtcta atgcttcctt ctagatgtta cccgaacatc    1080
tacaaaaccc agggcaacta ttcctatgac gaatcaaaga ttccatgggg cgtcaatgaa    1140
ggttgtgtcc caactgaagg gagcatggaa gttattgagg tggatccacg cgagggctgg    1200
gcaagtttca agttcatcgg tgccgcattc atgaagtctc ttgttgtctc gatcgacgaa    1260
catccaatgt ggatctacga ggttgatgga cactatatcg agcccggcct cgtgcacgac    1320
ttcccccttgt tcaatggtga acggtacggt gcgatggtca agcttgacaa gaccccccaag    1380
aactacacca ttcgagttac agacacgaac ggtgatcaga tcattgcggg atatgccacc    1440
ttgtcgtaca agggtggaaa ggatttggga ccgtcgaaac cttacatcaa ctacggcggt    1500
ctcaatgtct ctgcggatgt ggtacagttg aataccacga acctacctcc ttacccgaat    1560
gtcaaaccag ctcgcagcgc agaccagctt tttaacctca caatgggtcg tatcgaatca    1620
tcttggcagt ggactttgca gggcgaacag ctctacgatg tcggcgcgaa cgcgaatacc    1680
cccatcttgt tcgacctgga cgcaaggaag aatttgggcg acaaactcac ccttcccacc    1740
aggaacggca cctgggtaga tctgctgctg cagttgggtc agttcccaaa gactccgaag    1800
atccaagcac ctcacgtgat ccacaagcac tcgaacaagg ccttctggat cggtgcgggc    1860
cccggattct tcaactggac cagtgtcgac gaagccatcg catcgcatcc ggagtacttc    1920
aatctggagg accctatcta ccgagacaca ttcgtgacga atggcgcctt cggcccgacg    1980
tggatggtac tacggtacca agtcgtcaat cccggcccgt tcttgctcca ctgtcacatt    2040
gagacccact tgacagctgg tatgggcgtt gcattactcg acggagtgga tgtttggccc    2100
gaaatcccat cggaatacga catccgctat gggaaccatg gtcagcatac taatggcggg    2160
cagtga                                                                2166
```

```
<210> SEQ ID NO 14
<211> LENGTH: 606
<212> TYPE: PRT
<213> ORGANISM: Penicillium emersonii

<400> SEQUENCE: 14

Met Ala Pro Lys Gly Ser Phe Leu Thr Leu Cys Leu Ala Ala Leu Ala
1               5                   10                  15

Thr Ser Ala Tyr Ala Ala Thr Val Pro Phe Glu Leu His Leu Thr Trp
            20                  25                  30

Glu Glu Gly Ala Pro Asp Gly Asn Pro Arg Lys Met Ile Phe Met Asn
        35                  40                  45

Gly Gln Phe Pro Gly Pro Glu Leu Val Val Asp Glu Gly Asp Asp Val
    50                  55                  60

Glu Phe Leu Val His Asn His Leu Pro Phe Asn Thr Ser Ile His Phe
65                  70                  75                  80

His Gly Ile Glu Gln Met Asn Thr Pro Trp Ala Asp Gly Val Pro Gly
                85                  90                  95

Leu Thr Gln Lys Pro Ile Pro Pro Gly Glu Ser Phe Leu Tyr Arg Trp
            100                 105                 110

Thr Ala Thr Thr Tyr Gly Thr Tyr Trp Tyr His Ser His Tyr Ser Asn
        115                 120                 125

Thr Met Ala Asp Gly Leu Tyr Gly Pro Ile Trp Val Arg Pro Asn Pro
    130                 135                 140

His Thr Pro Thr Pro Phe His Leu Ile Ser Asn Asp Pro Ala Asp Leu
145                 150                 155                 160

Glu Ala Met Arg Arg Ala Glu His Asp Pro Arg Leu Val Val Leu Ser
                165                 170                 175

Asp Trp Glu His Leu Thr Ser Glu Glu Tyr Phe Asn Leu Gln Leu Ile
            180                 185                 190

Ser Gly Leu Asp Val Phe Cys Val Asp Ser Ile Leu Ile Asn Gly Lys
        195                 200                 205

Gly Ala Val His Cys Pro Ser Ala Glu Glu Ile Ala Ser Tyr Glu Thr
    210                 215                 220

Pro Tyr Leu Lys Gly Ala Ile Asp Asn Leu Pro Leu Thr Asp Lys Gly
225                 230                 235                 240

Cys Tyr Pro Asn Ile Tyr Lys Thr Gln Gly Asn Tyr Ser Tyr Asp Glu
                245                 250                 255

Ser Lys Ile Pro Trp Gly Val Asn Glu Gly Cys Val Pro Thr Glu Gly
            260                 265                 270

Ser Met Glu Val Ile Glu Val Asp Pro Arg Glu Gly Trp Ala Ser Phe
        275                 280                 285

Lys Phe Ile Gly Ala Ala Phe Met Lys Ser Leu Val Val Ser Ile Asp
    290                 295                 300

Glu His Pro Met Trp Ile Tyr Glu Val Asp Gly His Tyr Ile Glu Pro
305                 310                 315                 320

Arg Leu Val His Asp Phe Pro Leu Phe Asn Gly Glu Arg Tyr Gly Ala
                325                 330                 335

Met Val Lys Leu Asp Lys Thr Pro Lys Asn Tyr Thr Ile Arg Val Thr
            340                 345                 350

Asp Thr Asn Gly Asp Gln Ile Ile Ala Gly Tyr Ala Thr Leu Ser Tyr
        355                 360                 365

Lys Gly Gly Lys Asp Leu Gly Pro Ser Lys Pro Tyr Ile Asn Tyr Gly
    370                 375                 380
```

```
Gly Leu Asn Val Ser Ala Asp Val Val Gln Leu Asn Thr Thr Asn Leu
385                 390                 395                 400

Pro Pro Tyr Pro Asn Val Lys Pro Ala Arg Ser Ala Asp Gln Leu Phe
            405                 410                 415

Asn Leu Thr Met Gly Arg Ile Glu Ser Ser Trp Gln Trp Thr Leu Gln
        420                 425                 430

Gly Glu Gln Leu Tyr Asp Val Gly Ala Asn Ala Asn Thr Pro Ile Leu
        435                 440                 445

Phe Asp Leu Asp Ala Arg Lys Asn Leu Gly Asp Lys Leu Thr Leu Pro
    450                 455                 460

Thr Arg Asn Gly Thr Trp Val Asp Leu Leu Gln Leu Gly Gln Phe
465                 470                 475                 480

Pro Lys Thr Pro Lys Ile Gln Ala Pro His Val Ile His Lys His Ser
            485                 490                 495

Asn Lys Ala Phe Trp Ile Gly Ala Gly Pro Gly Phe Phe Asn Trp Thr
        500                 505                 510

Ser Val Asp Glu Ala Ile Ala Ser His Pro Glu Tyr Phe Asn Leu Glu
    515                 520                 525

Asp Pro Ile Tyr Arg Asp Thr Phe Val Thr Asn Gly Ala Phe Gly Pro
530                 535                 540

Thr Trp Met Val Leu Arg Tyr Gln Val Val Asn Pro Gly Pro Phe Leu
545                 550                 555                 560

Leu His Cys His Ile Glu Thr His Leu Thr Ala Gly Met Gly Val Ala
            565                 570                 575

Leu Leu Asp Gly Val Asp Val Trp Pro Glu Ile Pro Ser Glu Tyr Asp
        580                 585                 590

Ile Arg Tyr Gly Asn His Gly Gln His Thr Asn Gly Gly Gln
    595                 600                 605

<210> SEQ ID NO 15
<211> LENGTH: 1726
<212> TYPE: DNA
<213> ORGANISM: Penicillium emersonii

<400> SEQUENCE: 15
atgaaactct ggtttccagt cttttgcatc ctcgccacag ccaccgctct gtcgacctgt      60
gcaggaaata cccccagcag cagatcatcc tggtgcgact acagcatcag caccaactac     120
tacgacgtcg tccccgacac gggcgtcact cgcgaatact acttcaccct gcaggaggtg     180
accctcgccc ctgatggctt cgagcgaatc acctacacag tcaacgggac catcccaggc     240
ccgacgatcg aagccgactg gggcgacacg gtcgtcgtgc atgtcacgaa caacctcacc     300
gcgtccggga cggcaccag catccatttc acggcatcc gccagaacta caccaacccg      360
atggacggcg tgacgtcgat cacgcagtgt cccaccgcgc cgggcgagac catcacgtac     420
acctggcgag cgacgcagta cggctcgtcg tggtatcact cgcacatcgg gctgcaggcc     480
tgggagggcg tcatgggcgg catcatcgtc acgggcccg cgacggccaa ctacgacgag      540
gacaaaggcg tcctgttcct caccgactgg agccatgcca ccgtcgacga gctgtatgag     600
tccgtcctgg cgaacggccc ggccacgctc gacaatgccc tcatcaacgg caccaacgtc     660
tacggcgcgg acaatgccac caccagacg ggacatcgct tcaatacgtc cttcacagcc      720
ggcacgtcct atcgcttccg gctggtcaat ggcgcgattg atacgcattt caaattctcc     780
atcgacaatc acaccctcac cgtcattgcc agtgactttg tccccattga gccgtataat     840
acgactgttc ttagcattgc gatgggtaag aatgttcaac tcctgtaagt cggttcctgc     900
```

-continued

```
taacgatgca ggccaacggt acgacatcat cgtcacggcc gaccaggaat ctgttgcgga       960
gaatttctgg atgcgcgcca tcccccaggc agcctgctcc gagaacgaca gcgcggacaa      1020
catcaagggc atcgtgtact acggcgactc gcccgcgacg ccgaccacca ccgggtacgc      1080
gtacacggac gactgcgacg acgaggccct gagccatctg gtgccgtacc tgtcgctgga      1140
cgcgggggac tactactgga acgagagcga gccggtgacg atccagcagg cggcggcgaa      1200
cgtgttcctg tggtacatga acgacacgtc gctgagcgtg gactgggcga acccgacgct      1260
gctgcaggtg tacaacaacg cgacgtcctt ctccaacacg agcggcgtga tccagctgcc      1320
ccgggcggac gagtgggcgt acgtggtgat cacgacgacg atcgcggtgc cgcacccggt      1380
gcatctgcac ggccacgact tctttatcct cgcccagggc acgggcacgt acgacccggc      1440
gacggatctg atcagcctga cgaatccgcc acgtcgggac acggccatgc tccctgcgtc      1500
ggggtatctg gtggtcgcgt tcaagacgga caacccgggg gcgtggctga tgcattgcca      1560 tatcggggtgg catacggaga tggggctggc gatccagttc atcgagcagt acgatgtggc      1620
gcgcagtctg atcgactatc ggtctttgca ggcaaactgc gcggcgtggg agtcgtatgc      1680
gagggaggag ggtgcggtgc agaacaagta tgatgatggt atctag                    1726
```

<210> SEQ ID NO 16
<211> LENGTH: 559
<212> TYPE: PRT
<213> ORGANISM: Penicillium emersonii

<400> SEQUENCE: 16

```
Met Lys Leu Trp Phe Pro Val Phe Cys Ile Leu Ala Thr Ala Thr Ala
1               5                   10                  15

Leu Ser Thr Cys Ala Gly Asn Thr Pro Ser Ser Arg Ser Ser Trp Cys
            20                  25                  30

Asp Tyr Ser Ile Ser Thr Asn Tyr Tyr Asp Val Val Pro Asp Thr Gly
        35                  40                  45

Val Thr Arg Glu Tyr Tyr Phe Thr Leu Gln Glu Val Thr Leu Ala Pro
    50                  55                  60

Asp Gly Phe Glu Arg Ile Thr Tyr Thr Val Asn Gly Thr Ile Pro Gly
65                  70                  75                  80

Pro Thr Ile Glu Ala Asp Trp Gly Asp Thr Val Val His Val Thr
                85                  90                  95

Asn Asn Leu Thr Ala Ser Gly Asn Gly Thr Ser Ile His Phe His Gly
            100                 105                 110

Ile Arg Gln Asn Tyr Thr Asn Pro Met Asp Gly Val Thr Ser Ile Thr
        115                 120                 125

Gln Cys Pro Thr Ala Pro Gly Glu Thr Ile Thr Tyr Thr Trp Arg Ala
    130                 135                 140

Thr Gln Tyr Gly Ser Ser Trp Tyr His Ser His Ile Gly Leu Gln Ala
145                 150                 155                 160

Trp Glu Gly Val Met Gly Gly Ile Ile Val His Gly Pro Ala Thr Ala
                165                 170                 175

Asn Tyr Asp Glu Asp Lys Gly Val Leu Phe Leu Thr Asp Trp Ser His
            180                 185                 190

Ala Thr Val Asp Glu Leu Tyr Glu Ser Val Leu Ala Asn Gly Pro Ala
        195                 200                 205

Thr Leu Asp Asn Ala Leu Ile Asn Gly Thr Asn Val Tyr Gly Ala Asp
    210                 215                 220
```

```
Asn Ala Thr Thr Gln Thr Gly His Arg Phe Asn Thr Ser Phe Thr Ala
225                 230                 235                 240

Gly Thr Ser Tyr Arg Phe Arg Leu Val Asn Gly Ala Ile Asp Thr His
            245                 250                 255

Phe Lys Phe Ser Ile Asp Asn His Thr Leu Thr Val Ile Ala Ser Asp
            260                 265                 270

Phe Val Pro Ile Glu Pro Tyr Asn Thr Thr Val Leu Ser Ile Ala Met
        275                 280                 285

Gly Gln Arg Tyr Asp Ile Ile Val Thr Ala Asp Gln Glu Ser Val Ala
        290                 295                 300

Glu Asn Phe Trp Met Arg Ala Ile Pro Gln Ala Ala Cys Ser Glu Asn
305                 310                 315                 320

Asp Ser Ala Asp Asn Ile Lys Gly Ile Val Tyr Tyr Gly Asp Ser Pro
            325                 330                 335

Ala Thr Pro Thr Thr Thr Gly Tyr Ala Tyr Thr Asp Cys Asp Asp
            340                 345                 350

Glu Ala Leu Ser His Leu Val Pro Tyr Leu Ser Leu Asp Ala Gly Asp
        355                 360                 365

Tyr Tyr Trp Asn Glu Ser Glu Pro Val Thr Ile Gln Gln Ala Ala Ala
370                 375                 380

Asn Val Phe Leu Trp Tyr Met Asn Asp Thr Ser Leu Ser Val Asp Trp
385                 390                 395                 400

Ala Asn Pro Thr Leu Leu Gln Val Tyr Asn Asn Ala Thr Ser Phe Ser
            405                 410                 415

Asn Thr Ser Gly Val Ile Gln Leu Pro Arg Ala Asp Glu Trp Ala Tyr
            420                 425                 430

Val Val Ile Thr Thr Thr Ile Ala Val Pro His Pro Val His Leu His
        435                 440                 445

Gly His Asp Phe Phe Ile Leu Ala Gln Gly Thr Gly Thr Tyr Asp Pro
        450                 455                 460

Ala Thr Asp Leu Ile Ser Leu Thr Asn Pro Pro Arg Arg Asp Thr Ala
465                 470                 475                 480

Met Leu Pro Ala Ser Gly Tyr Leu Val Val Ala Phe Lys Thr Asp Asn
            485                 490                 495

Pro Gly Ala Trp Leu Met His Cys His Ile Gly Trp His Thr Glu Met
        500                 505                 510

Gly Leu Ala Ile Gln Phe Ile Glu Gln Tyr Asp Val Ala Arg Ser Leu
        515                 520                 525

Ile Asp Tyr Arg Ser Leu Gln Ala Asn Cys Ala Ala Trp Glu Ser Tyr
        530                 535                 540

Ala Arg Glu Glu Gly Ala Val Gln Asn Lys Tyr Asp Asp Gly Ile
545                 550                 555

<210> SEQ ID NO 17
<211> LENGTH: 1879
<212> TYPE: DNA
<213> ORGANISM: Penicillium emersonii

<400> SEQUENCE: 17
atggggatag cacttagatt actatataca acatatctcc tattcctaat ttcgaaactc    60
accctcgcag ccaacaacgg ccagcaagtc caagtccaca tccacgacga atccttcacc   120
ccagacatca tcctccggat cacagcagag aactacacgc aagcatgcca cgagcggtac   180
tccgtcctga tcaacggctc ctctcccgga ccggagatcc gactccaaga aggccagacg   240
```

```
acgtggataa gggtgtacaa tgatatggag ggggagaaca ttactatggt agcagccta      300
tcctatcctc atgtactatt tgttattagc tttgttaata tcttggttgc tgcagcactg      360
gcacggcctc agcatggtcg tcgcccctt ctcggacggc acacccctcg cttcgcaatg      420
gccgattccg ccgggatact tcttcgacta cgaaatccgg ccggatgagg gctatgccgg      480
gggaacgtat ttctatcact cgcatgtggg cttcagggt gtctctgctg cgggcgcgct      540
gattgttgat gaggccagtt cccctgcacc ttatcagtat gatgaggaga ggattctcct      600
ccttggagat tcttccca ggacggatcg cgagattgag aaggggctta cgagtacggg      660
ggagaatttc acctggacgg gtgagccgga tgcggtgctc gttaatgggc tgggtttacc      720
tgtcaacacg gacggtggca gcagcagcgg tggcagtggc tgctccatgg cgactatcga      780
cgtcgaaccc ggcaagacgt atcgtctccg cttcatcggt agcacggcgc tgtcgttcct      840
gcgtgtggag atcgagggcc acgagatgga gatcatcgaa gcagatggcc aatacgtcca      900
gccagtgccc acgaactaca tccagatcgg cagcgggcag cggtacagcg cgctgctccg      960
caccaagacc gagagcgagc tgtctcagag tagtaaatgg tactcttata tccagctcgt     1020
cacgctcgac cgtcctgaag tccgcactgg gtatgccgtt ctgcggtacc ccagcgccga     1080
taatgatgtc gatctcacga cggctccgag cacgcctcct ctgcccgtcg cgtcgacatc     1140
aaccccccgga tggctggact acgagctgcg tgcgctgcgg ccggattctg acttcccgtc     1200
cctggggcag gtcacccggc ggatcgtcat cgacgtgcat cagaccgtca gcgagggcgg     1260
caacttctgg gtcatgaacg gataccctg gacggacgcc gtgcctaagt cgccatacct     1320
gatcgacatc tacgaaggaa gatacgacct ggacgcggcg tacgagcgcg cggtggacaa     1380
cggcagcggt ttcgacgccg tcacgcgcac attccaggcc aagatgggcg aggtgctgga     1440
gatcgtgtgg cagaaccagg gctcccccgg gactggcggc gtcagacgc acccgttgca     1500
cgcgcacggg cggcacgtct acgacctcgg cggcggagag ggcacgtacg acgctgtcgc     1560
caacgaggcg cgactgtaca tgaacccgcc cgtgcggcgc gacacgacga tgctgtatcg     1620
gtaccgcgag aagacgacgc cggggggagaa cgcgagctgg cgggcgtggc ggctcagggt     1680
cgacgacgcg ggagtgtgga tgatgcactg ccacatcctg cagcatatga tcatgggcat     1740
gcagacggtg tttgtctttg cgataagga gcagatcgta cgccagacgg gcacggcgtc     1800
gtatggctat ctgacttttg cgggccggc atatggaaac ggcacgcatt ggccggaggt     1860
gatgcattat tttgactga                                                 1879
```

<210> SEQ ID NO 18
<211> LENGTH: 603
<212> TYPE: PRT
<213> ORGANISM: Penicillium emersonii

<400> SEQUENCE: 18

Met Gly Ile Ala Leu Arg Leu Leu Tyr Thr Thr Tyr Leu Leu Phe Leu
1               5                   10                  15

Ile Ser Lys Leu Thr Leu Ala Ala Asn Asn Gly Gln Gln Val Gln Val
            20                  25                  30

His Ile His Asp Glu Ser Phe Thr Pro Asp Ile Ile Leu Arg Ile Thr
        35                  40                  45

Ala Glu Asn Tyr Thr Gln Ala Cys His Glu Arg Tyr Ser Val Leu Ile
    50                  55                  60

Asn Gly Ser Ser Pro Gly Pro Glu Ile Arg Leu Gln Glu Gly Gln Thr
65                  70                  75                  80

```
Thr Trp Ile Arg Val Tyr Asn Asp Met Glu Gly Glu Asn Ile Thr Met
                 85                  90                  95
His Trp His Gly Leu Ser Met Val Val Ala Pro Phe Ser Asp Gly Thr
            100                 105                 110
Pro Leu Ala Ser Gln Trp Pro Ile Pro Pro Gly Tyr Phe Phe Asp Tyr
            115                 120                 125
Glu Ile Arg Pro Asp Glu Gly Tyr Ala Gly Gly Thr Tyr Phe Tyr His
            130                 135                 140
Ser His Val Gly Phe Gln Gly Val Ser Ala Ala Gly Ala Leu Ile Val
145                 150                 155                 160
Asp Glu Ala Ser Ser Pro Ala Pro Tyr Gln Tyr Asp Glu Glu Arg Ile
                165                 170                 175
Leu Leu Leu Gly Asp Phe Phe Pro Arg Thr Asp Arg Glu Ile Glu Lys
            180                 185                 190
Gly Leu Thr Ser Thr Gly Glu Asn Phe Thr Trp Thr Gly Glu Pro Asp
            195                 200                 205
Ala Val Leu Val Asn Gly Leu Gly Leu Pro Val Asn Thr Asp Gly Gly
            210                 215                 220
Ser Ser Ser Gly Gly Ser Gly Cys Ser Met Ala Thr Ile Asp Val Glu
225                 230                 235                 240
Pro Gly Lys Thr Tyr Arg Leu Arg Phe Ile Gly Ser Thr Ala Leu Ser
                245                 250                 255
Phe Leu Arg Val Glu Ile Glu Gly His Glu Met Glu Ile Ile Glu Ala
                260                 265                 270
Asp Gly Gln Tyr Val Gln Pro Val Pro Thr Asn Tyr Ile Gln Ile Gly
            275                 280                 285
Ser Gly Gln Arg Tyr Ser Ala Leu Leu Arg Thr Lys Thr Glu Ser Glu
            290                 295                 300
Leu Ser Gln Ser Ser Lys Trp Tyr Ser Tyr Ile Gln Leu Val Thr Leu
305                 310                 315                 320
Asp Arg Pro Glu Val Arg Thr Gly Tyr Ala Val Leu Arg Tyr Pro Ser
                325                 330                 335
Ala Asp Asn Asp Val Asp Leu Thr Thr Ala Pro Ser Thr Pro Pro Leu
            340                 345                 350
Pro Val Ala Ser Thr Ser Thr Pro Gly Trp Leu Asp Tyr Glu Leu Arg
            355                 360                 365
Ala Leu Arg Pro Asp Ser Asp Phe Pro Ser Leu Gly Gln Val Thr Arg
            370                 375                 380
Arg Ile Val Ile Asp Val His Gln Thr Val Ser Glu Gly Gly Asn Phe
385                 390                 395                 400
Trp Val Met Asn Gly Tyr Pro Trp Thr Asp Ala Val Pro Lys Ser Pro
                405                 410                 415
Tyr Leu Ile Asp Ile Tyr Glu Gly Arg Tyr Asp Leu Asp Ala Ala Tyr
                420                 425                 430
Glu Arg Ala Val Asp Asn Gly Ser Gly Phe Asp Ala Val Thr Arg Thr
            435                 440                 445
Phe Gln Ala Lys Met Gly Glu Val Leu Glu Ile Val Trp Gln Asn Gln
            450                 455                 460
Gly Ser Pro Gly Thr Gly Val Glu Thr His Pro Leu His Ala His
465                 470                 475                 480
Gly Arg His Val Tyr Asp Leu Gly Gly Gly Glu Gly Thr Tyr Asp Ala
                485                 490                 495
Val Ala Asn Glu Ala Arg Leu Tyr Met Asn Pro Pro Val Arg Arg Asp
```

```
                      500               505               510
Thr Thr Met Leu Tyr Arg Tyr Arg Glu Lys Thr Thr Pro Gly Glu Asn
            515               520               525

Ala Ser Trp Arg Ala Trp Arg Leu Arg Val Asp Asp Ala Gly Val Trp
        530               535               540

Met Met His Cys His Ile Leu Gln His Met Ile Met Gly Met Gln Thr
545               550               555               560

Val Phe Val Phe Gly Asp Lys Glu Gln Ile Val Arg Gln Thr Gly Thr
                565               570               575

Ala Ser Tyr Gly Tyr Leu Thr Phe Gly Gly Pro Ala Tyr Gly Asn Gly
            580               585               590

Thr His Trp Pro Glu Val Met His Tyr Phe Asp
        595               600

<210> SEQ ID NO 19
<211> LENGTH: 1926
<212> TYPE: DNA
<213> ORGANISM: Penicillium emersonii

<400> SEQUENCE: 19
atggctctct cactatcttt cttcctgggg accatattct gggcctctgt agctgttgca      60
gacacccgaa catatgattt caacatcacg tgggtttcag caaatccaga cggcctgtat     120
actcgccctg tgattggaat caatggccaa tggccgatcc ccgtgattaa agccacagtg     180
ggcgacaggc tcatcgtcaa cgtgcacaat cagttgggaa acgagagcac ctctctccat     240
ttccatggtc tctttcagaa tggcaccaca gagatggatg cccctgcagg ggtcacgcaa     300
tgtcccatcc caccgggaag ctctttcacc tataatttca ccgtacgtac ttgccattga     360
aactacccag cgataaatac ctgggttgct gacgtttctt agatcgatca accgggtacc     420
tactggtatc attcgcacct caagggccag tatccggacg tctgcgtgg ccgcttatc      480 gtcgaagatc caaactcacc gtataagggg aaatacgacg aagagttcgt tctgactctg     540
tcagactggt atcatgcccc gatgcaatct ctgctgaaat cattcatgag ctataccaac     600
ccgacaggcg cggaacctgt gccaaattcg gcgttgatga acgacacgca gaatgtgacc     660
attaccgttg aaccgggaaa gacgtatttt ttccgtatca ttaacatggg cgccttcgct     720
ggccagtact tctggattga aggccataag atgcgtattg tcgaagccga cggcgtgtgg     780
acaaatgagg cagaagcgga tatgttgtac gttaccgccg cacagagata tggcgtgttg     840
gtgacgacga gaacgacac ctctgccaac tacccccatcg tgagcagcat ggatcaagtc      900
agcaacacca ttccttgtca tccacacaga acagtctatt aactgggcgc aggacatgtt     960
tgataaagtt cccgcaggac tgaacccgaa tgtcacgagc tatctggtct acgacagcac    1020
gaagagctta ccaccggctc agaacgtcga tgacttcagc ccgttcgatg atttctccct    1080
cgtcccaagt gatggcctgg ggattttcga aaatgtcgac cgttcgatca ccttgcgagt    1140
gaaaatggat aatctcggag acggtgtgaa ttagtgagta atccatcccc tgtcgcaagg    1200
aataatgaga gtacgtacta accacatgga cggctcagtg cgttttttcaa cgacatcacc    1260 tatgtctctc aaaaggtgcc cactctctac actgctctct ccgctccggc agacgtcgtc    1320
accaacgcca gcatctacgg cgtcaacagt aattccttca tgctcaacca cggcgaggtc    1380
gtcgagctgg tgatcaacaa tgatgacccc ggaaagcatc cgttccacct gcacgcacac    1440
aacttccagg tagtcgctcg ggccggcaac gatgctggct tctacgaccc gacaaacttc    1500
acgttttccc aagtccccat gcgtcgagat acgatcctcg ttcatccctc gagtaacgct    1560
```

-continued

```
gttctccgct tccgcgccga caaccctggc gtgtggctct tccactgcca cattgaatgg    1620
cacatgaaca gcgggctggt cgcgaccatg gtcgaagccc cgctcgagtt gcaggcccag    1680
aaacgtggcc aaggcatcct gagtctgccg gccgaccata tcgccgcctg caaggcggga    1740
ggcaacctgt atgaaggaaa cgcaggtggt aacactgtcg actggttcga cctccagaac    1800
gcaaactacc aaccggcccc gctccccaaa ggcttcacag ccaggggtat cgttgccctg    1860
gtgttcagca tcctttctgc attcctggga ctggcagtca ttagctggta tggagctgca    1920
agataa                                                                1926
```

<210> SEQ ID NO 20
<211> LENGTH: 581
<212> TYPE: PRT
<213> ORGANISM: Penicillium emersonii

<400> SEQUENCE: 20

| | | | | | | | | | | | | | | |
|---|---|---|---|---|---|---|---|---|---|---|---|---|---|---|
| Met | Ala | Leu | Ser | Leu | Ser | Phe | Phe | Leu | Gly | Thr | Ile | Phe | Trp | Ala | Ser |
| 1 | | | | 5 | | | | | 10 | | | | | 15 | |
| Val | Ala | Val | Ala | Asp | Thr | Arg | Thr | Tyr | Asp | Phe | Asn | Ile | Thr | Trp | Val |
| | | | 20 | | | | | 25 | | | | | 30 | | |
| Ser | Ala | Asn | Pro | Asp | Gly | Leu | Tyr | Thr | Arg | Pro | Val | Ile | Gly | Ile | Asn |
| | | | | 35 | | | | | 40 | | | | | 45 | |
| Gly | Gln | Trp | Pro | Ile | Pro | Val | Ile | Lys | Ala | Thr | Val | Gly | Asp | Arg | Leu |
| | 50 | | | | | 55 | | | | | 60 | | | | |
| Ile | Val | Asn | Val | His | Asn | Gln | Leu | Gly | Asn | Glu | Ser | Thr | Ser | Leu | His |
| 65 | | | | | 70 | | | | | 75 | | | | | 80 |
| Phe | His | Gly | Leu | Phe | Gln | Asn | Gly | Thr | Thr | Glu | Met | Asp | Gly | Pro | Ala |
| | | | | 85 | | | | | 90 | | | | | 95 | |
| Gly | Val | Thr | Gln | Cys | Pro | Ile | Pro | Pro | Gly | Ser | Ser | Phe | Thr | Tyr | Asn |
| | | | | 100 | | | | | 105 | | | | | 110 | |
| Phe | Thr | Ile | Asp | Gln | Pro | Gly | Thr | Tyr | Trp | Tyr | His | Ser | His | Leu | Lys |
| | | | 115 | | | | | 120 | | | | | 125 | | |
| Gly | Gln | Tyr | Pro | Asp | Gly | Leu | Arg | Gly | Pro | Leu | Ile | Val | Glu | Asp | Pro |
| | 130 | | | | | 135 | | | | | 140 | | | | |
| Asn | Ser | Pro | Tyr | Lys | Gly | Lys | Tyr | Asp | Glu | Glu | Phe | Val | Leu | Thr | Leu |
| 145 | | | | | 150 | | | | | 155 | | | | | 160 |
| Ser | Asp | Trp | Tyr | His | Ala | Pro | Met | Gln | Ser | Leu | Leu | Lys | Ser | Phe | Met |
| | | | | 165 | | | | | 170 | | | | | 175 | |
| Ser | Tyr | Thr | Asn | Pro | Thr | Gly | Ala | Glu | Pro | Val | Pro | Asn | Ser | Ala | Leu |
| | | | | 180 | | | | | 185 | | | | | 190 | |
| Met | Asn | Asp | Thr | Gln | Asn | Val | Thr | Ile | Thr | Val | Glu | Pro | Gly | Lys | Thr |
| | | | 195 | | | | | 200 | | | | | 205 | | |
| Tyr | Phe | Phe | Arg | Ile | Ile | Asn | Met | Gly | Ala | Phe | Ala | Gly | Gln | Tyr | Phe |
| | | 210 | | | | | 215 | | | | | 220 | | | |
| Trp | Ile | Glu | Gly | His | Lys | Met | Arg | Ile | Val | Glu | Ala | Asp | Gly | Val | Trp |
| 225 | | | | | 230 | | | | | 235 | | | | | 240 |
| Thr | Asn | Glu | Ala | Glu | Ala | Asp | Met | Leu | Tyr | Val | Thr | Ala | Ala | Gln | Arg |
| | | | | 245 | | | | | 250 | | | | | 255 | |
| Tyr | Gly | Val | Leu | Val | Thr | Thr | Lys | Asn | Asp | Thr | Ser | Ala | Asn | Tyr | Pro |
| | | | | 260 | | | | | 265 | | | | | 270 | |
| Ile | Val | Ser | Ser | Met | Asp | Gln | Asp | Met | Phe | Asp | Lys | Val | Pro | Ala | Gly |
| | | | 275 | | | | | 280 | | | | | 285 | | |
| Leu | Asn | Pro | Asn | Val | Thr | Ser | Tyr | Leu | Val | Tyr | Asp | Ser | Thr | Lys | Ser |
| | 290 | | | | | 295 | | | | | 300 | | | | |

Leu Pro Pro Ala Gln Asn Val Asp Asp Phe Ser Pro Phe Asp Asp Phe
305                 310                 315                 320

Ser Leu Val Pro Ser Asp Gly Leu Gly Ile Phe Glu Asn Val Asp Arg
            325                 330                 335

Ser Ile Thr Leu Arg Val Lys Met Asp Asn Leu Gly Asp Gly Val Asn
        340                 345                 350

Tyr Ala Phe Phe Asn Asp Ile Thr Tyr Val Ser Gln Lys Val Pro Thr
    355                 360                 365

Leu Tyr Thr Ala Leu Ser Ala Pro Ala Asp Val Val Thr Asn Ala Ser
370                 375                 380

Ile Tyr Gly Val Asn Ser Asn Ser Phe Met Leu Asn His Gly Glu Val
385                 390                 395                 400

Val Glu Leu Val Ile Asn Asn Asp Asp Pro Gly Lys His Pro Phe His
                405                 410                 415

Leu His Ala His Asn Phe Gln Val Val Ala Arg Ala Gly Asn Asp Ala
            420                 425                 430

Gly Phe Tyr Asp Pro Thr Asn Phe Thr Phe Pro Gln Val Pro Met Arg
        435                 440                 445

Arg Asp Thr Ile Leu Val His Pro Ser Ser Asn Ala Val Leu Arg Phe
450                 455                 460

Arg Ala Asp Asn Pro Gly Val Trp Leu Phe His Cys His Ile Glu Trp
465                 470                 475                 480

His Met Asn Ser Gly Leu Val Ala Thr Met Val Glu Ala Pro Leu Glu
                485                 490                 495

Leu Gln Ala Gln Lys Arg Gly Gln Gly Ile Leu Ser Leu Pro Ala Asp
            500                 505                 510

His Ile Ala Ala Cys Lys Ala Gly Asn Leu Tyr Glu Gly Asn Ala
        515                 520                 525

Gly Gly Asn Thr Val Asp Trp Phe Asp Leu Gln Asn Ala Asn Tyr Gln
    530                 535                 540

Pro Ala Pro Leu Pro Lys Gly Phe Thr Ala Arg Gly Ile Val Ala Leu
545                 550                 555                 560

Val Phe Ser Ile Leu Ser Ala Phe Leu Gly Leu Ala Val Ile Ser Trp
                565                 570                 575

Tyr Gly Ala Ala Arg
            580

<210> SEQ ID NO 21
<211> LENGTH: 1892
<212> TYPE: DNA
<213> ORGANISM: Penicillium emersonii

<400> SEQUENCE: 21
atggcctcgc tgatgcgcct gtggctactt ctcagcctgc tggtatggtg ccaggcggcg      60
gtcgtgcctt ttgagatcac cctgacctgg gccactgtcg ctccggacgg cgtcccccag     120
aaggccatct tgtccaacgg ccagctgccc gggccgccgc tgtatctgga ccaaggcgac     180
gaggtggagt tctctggtcca caaccagctg ccgttcgcga cggcggtgca ttttcacggt     240
atgtgatgga gctgttctgt tcgcgaagga taacgaaatc taattttgac aggcattgaa     300
caactcgaca cgccctggtc cgacggcgtc cccggcctct cgcaacgccc aatccagccc     360
ggagacagct cctctctacaa gtggaaggcc acgcagtacg gcagctactt ctaccatgcc     420
cacgatcgcg gccagatcaa cgacggcctg tacggcgcga tcatcatccg cccgggggcc     480

-continued

```
gacgtcccca ggccgttcca cctcatcacc aacgactcca gcgagctcga ggccatccag    540
ctggccgagt tgcagacgaa gccgctcatc ctctccgact ggacccatta cacctcggag    600
cagatgtggg acatcgaaga ggccgccggg ctcgacgcgt actgcaccaa ctccatcctc    660
ttcaacggcc aggggtccgt cacgtgtctg ccgcagtcgg tcatcgacgc gaacgcgaat    720
ccggcggtga tccagctgct caatggcacc gataatcact tgacggacat ggggtaggtt    780
accttgactt ctaatgaagg ctggatagct gattgcacag gtgtctgccc ccacgttgg    840
ccatcgccca agggccgtac ccgcacaatt tcagcgctgc accccgggc gtctggtcgg    900
gttgcaagcc ctcgcaaggg ccgacggagg tgtggaaggt caacccggag gtgcggtacg    960
cgagttggga gctgatctcg gcggcgggca tctcgacctt cgtcttctcc atcgacgagc   1020
atcccatgtg ggtgtacgcg gtcgacgggc ggtacgtgac gccgacgcag gcggacgcgc   1080
tcaccatcac caacgggcaa cggttctcga tcctggtgaa gctggacaag ccgccggcga   1140
actacaacat cgcacggtc gtgacggggc tcaaccagct gctgaacggg accgcgatcc   1200
tgtcatacgc ggacgcgtcg gagccggcgg gcaattgggc ccgtcggtg tcgtcgatca   1260
cgctgaacgg cctcaacgcg acggccaaca cgaccttctg gaacgagtcc ctggcggtgc   1320
cgtacccgcc ggtcgcgccc gcgccgttcg cgaacgagac gtacgtgctg cgcctcaacc   1380
ggtggaacgc gtcgtaccgg tggtacctgg ggaacgacag tttcccgctg tccctacagg   1440
acgacaagcc gctgctgttc gacccgaacg cgcaggggcc gcacagcgac ctgacggtgc   1500
ggacgcagaa cgggtcatgg gtggacatca tcttccacgc ggtgacgccg ctgcagccga   1560
tccatccgtt ccacaagcac tcgaacaagt ttttgtcat cgggtcgggc gtggggccgt   1620
ggaactactc ctcggtcgaa gaggccatgc aacacacccc ggaaagtttc aacctgatcg   1680
acccccgat gcgtgacacc tactcgacgc cggcatccat ggacggcgag agctggctgg   1740
ccgtgcggta ccaggtcgtc aacccgggcg cgttcctgct gcactgccac atccagttgc   1800
atctggacgg ggggatggcg ttggcgctgt tggacgggga cgacaagtgg ccggcggtac   1860
cggatgagta tttgaatggg aatggttttt ga                                1892
```

<210> SEQ ID NO 22
<211> LENGTH: 596
<212> TYPE: PRT
<213> ORGANISM: Penicillium emersonii

<400> SEQUENCE: 22

```
Met Ala Ser Leu Met Arg Leu Trp Leu Leu Ser Leu Leu Val Trp
1               5                   10                  15

Cys Gln Ala Ala Val Val Pro Phe Glu Ile Thr Leu Thr Trp Ala Thr
                20                  25                  30

Val Ala Pro Asp Gly Val Pro Arg Lys Ala Ile Leu Ser Asn Gly Gln
            35                  40                  45

Leu Pro Gly Pro Pro Leu Tyr Leu Asp Gln Gly Asp Glu Val Glu Phe
        50                  55                  60

Leu Val His Asn Gln Leu Pro Phe Ala Thr Ala Val His Phe His Gly
65                  70                  75                  80

Ile Glu Gln Leu Asp Thr Pro Trp Ser Asp Gly Val Pro Gly Leu Ser
                85                  90                  95

Gln Arg Pro Ile Gln Pro Gly Asp Ser Phe Leu Tyr Lys Trp Lys Ala
            100                 105                 110

Thr Gln Tyr Gly Ser Tyr Phe Tyr His Ala His Asp Arg Gly Gln Ile
        115                 120                 125
```

```
Asn Asp Gly Leu Tyr Gly Ala Ile Ile Ile Arg Pro Gly Asp Val
    130                 135                 140

Pro Arg Pro Phe His Leu Ile Thr Asn Asp Ser Ser Glu Leu Glu Ala
145                 150                 155                 160

Ile Gln Leu Ala Glu Leu Gln Thr Lys Pro Leu Ile Leu Ser Asp Trp
                165                 170                 175

Thr His Tyr Thr Ser Glu Gln Met Trp Asp Ile Glu Glu Ala Ala Gly
                180                 185                 190

Leu Asp Ala Tyr Cys Thr Asn Ser Ile Leu Phe Asn Gly Gln Gly Ser
                195                 200                 205

Val Thr Cys Leu Pro Gln Ser Val Ile Asp Ala Asn Ala Asn Pro Ala
    210                 215                 220

Val Ile Gln Leu Leu Asn Gly Thr Asp Asn His Leu Thr Asp Met Gly
225                 230                 235                 240

Cys Leu Pro Pro Thr Leu Ala Ile Ala Gln Gly Pro Tyr Pro His Asn
                245                 250                 255

Phe Ser Ala Ala Pro Pro Gly Val Trp Ser Gly Cys Lys Pro Ser Gln
                260                 265                 270

Gly Pro Thr Glu Val Trp Lys Val Asn Pro Glu Val Arg Tyr Ala Ser
                275                 280                 285

Trp Glu Leu Ile Ser Ala Ala Gly Ile Ser Thr Phe Val Phe Ser Ile
    290                 295                 300

Asp Glu His Pro Met Trp Val Tyr Ala Val Asp Gly Arg Tyr Val Thr
305                 310                 315                 320

Pro Thr Gln Ala Asp Ala Leu Thr Ile Thr Asn Gly Gln Arg Phe Ser
                325                 330                 335

Ile Leu Val Lys Leu Asp Lys Pro Pro Ala Asn Tyr Asn Met Arg Thr
                340                 345                 350

Val Val Thr Gly Leu Asn Gln Leu Leu Asn Gly Thr Ala Ile Leu Ser
                355                 360                 365

Tyr Ala Asp Ala Ser Glu Pro Ala Gly Asn Trp Ala Pro Ser Val Ser
    370                 375                 380

Ser Ile Thr Leu Asn Gly Leu Asn Ala Thr Ala Asn Thr Thr Phe Trp
385                 390                 395                 400

Asn Glu Ser Leu Ala Val Pro Tyr Pro Pro Val Ala Pro Ala Pro Phe
                405                 410                 415

Ala Asn Glu Thr Tyr Val Leu Arg Leu Asn Arg Trp Asn Ala Ser Tyr
                420                 425                 430

Arg Trp Tyr Leu Gly Asn Asp Ser Phe Pro Leu Ser Leu Gln Asp Asp
    435                 440                 445

Lys Pro Leu Leu Phe Asp Pro Asn Ala Gln Gly Pro His Ser Asp Leu
450                 455                 460

Thr Val Arg Thr Gln Asn Gly Ser Trp Val Asp Ile Ile Phe His Ala
465                 470                 475                 480

Val Thr Pro Leu Gln Pro Ile His Pro Phe His Lys His Ser Asn Lys
                485                 490                 495

Phe Phe Val Ile Gly Ser Gly Val Gly Pro Trp Asn Tyr Ser Ser Val
                500                 505                 510

Glu Glu Ala Met Gln His Thr Pro Glu Ser Phe Asn Leu Ile Asp Pro
    515                 520                 525

Pro Met Arg Asp Thr Tyr Ser Thr Pro Ala Ser Met Asp Gly Glu Ser
530                 535                 540
```

Trp Leu Ala Val Arg Tyr Gln Val Val Asn Pro Gly Ala Phe Leu Leu
545                 550                 555                 560

His Cys His Ile Gln Leu His Leu Asp Gly Gly Met Ala Leu Ala Leu
                565                 570                 575

Leu Asp Gly Ile Asp Lys Trp Pro Ala Val Pro Asp Glu Tyr Leu Asn
            580                 585                 590

Gly Asn Gly Phe
        595

<210> SEQ ID NO 23
<211> LENGTH: 2115
<212> TYPE: DNA
<213> ORGANISM: Thermoascus aurantiacus

<400> SEQUENCE: 23

| | | | | | |
|---|---|---|---|---|---|
| atgtctttcg | ttaactcact | attccttctc | ttcaatgtct | tagctcctgc | tgtgtattcc | 60 |
| attccacacc | cggggcacct | ctccaaacgg | tgcaccaaca | gtgctactga | ccgcagctgt | 120 |
| tggggagact | tcgacctgtc | aacgaattac | tacgaggtgt | cccccgacac | gggtgttact | 180 |
| agagaggtat | gtacatacat | ctcccagact | ggaaaaaaaa | tacgtcttcg | ttgcaagact | 240 |
| cttctgctga | caattctcac | agtactggct | tgatattacg | aacacgaccg | ccgctccgga | 300 |
| tggaatagaa | cggattgtct | tgacagtcaa | tggaactgta | ccaggcccga | ccctctacgc | 360 |
| tgactggggt | gacactgttg | gtgagttccc | cttgtagtcc | tttaattgta | tggccacact | 420 |
| gctgatagca | ccgaagtcgt | ccatgttacg | aacagtttaa | gtgccaatgg | caccggcatt | 480 |
| cacttccacg | gcatcagaca | gaactacacc | aatcaaatgg | acggtgtccc | gtctataacg | 540 |
| cagtgtccag | tcgctgtagg | ttcttagatc | gtcaacgagc | tgtgtgtttc | aaagctaatt | 600 |
| ccaacgcttc | ttagcccgga | gactcgataa | catacacctg | gaaagccacc | caatacggaa | 660 |
| ccacttggta | tcactcccac | ttcagtctgc | aggcgtggga | gggcgtcttc | ggtgtgcttc | 720 |
| actttcatca | atgtcacggc | cgtcgagcgc | atatagctga | ccagtgagca | ggtggcattg | 780 |
| tcatcaacgg | cccagcatcg | gcaaactatg | acgaagatct | cggcccccctc | ttcctgtcag | 840 |
| actggacgca | tgagaccact | tgcgccctgt | tcacgcaagc | agagtattcc | ggcccccccga | 900 |
| caatggacaa | tggtctaatc | aacggcacga | atatctacaa | caacagcggt | accattgttg | 960 |
| ggtcgcgctt | ccagacgacc | ttcgagtcgg | gtaaaagcta | tcggctgcgg | ctgatcaacg | 1020 |
| gggcgaacga | ctcgcatttc | aagttcagca | tcgacaacca | caccatgacc | gtcattgcga | 1080 |
| acgatctggt | gcctatcgtc | ccgtatgaga | cgaacgtcct | caacattggc | ataggtgagt | 1140 |
| ttctaccgga | cggtcctgac | tacttaatag | atgtgtttct | tggcctttga | tcatattatt | 1200 |
| atataccctc | cggaaggcat | atcttactga | accaatactc | tacaggccaa | agatacgaca | 1260 |
| tcatcgtcaa | cgcaaccgct | accccccggca | actactggat | gcgcgcgatc | ccccaatcct | 1320 |
| gcagcgacaa | cgccaacggc | gacaacatcc | gcggaatcat | ccgctacgat | gccagcagca | 1380 |
| cggatgaccc | gaccagcacg | gcgtgggacc | aggaggtctc | ggattgcgag | gatgaagact | 1440 |
| cctccaacct | tgtcccgtac | ctgtctctag | atgctgctga | agaggactgg | ctggcatccc | 1500 |
| ttacggcaac | cgtcaaggga | accccgttca | gtggtacct | caatgacacc | acgatggctg | 1560 |
| tcaactggac | cagcccaacc | ctcaagcaga | tctatctgaa | cgagacagac | tgggaagaca | 1620 |
| gcgaagcggt | gtacgagctg | actaccgcgg | atgagtgggc | gtatatcatt | atccagagct | 1680 |
| cggctggtgc | tgcgcacccg | atccatctgc | acgttagtg | cccgtcgcaa | ataggctcat | 1740 |
| tgaagttata | cctgattgct | aacatcaaat | gtaggccacg | acttcaacgt | cctcgcttcc | 1800 |

```
ggctccggaa ctttcgacac ctccacctcc ctgtcctccc tcaacctctc caacccgccc    1860
cgccgcgacg tcgccctgct gcccgccaac ggctacctcg tgctcgcctt caaggccgac    1920
aacccgggcg cgtggctgat gcactgccac atcggctggc acaccgagga agggttctcg    1980
ctgcagatcg tcgagcgcat ggacgagttc cggagcatga tcgactacga cacgctgaac    2040
cagacctgca ccaactggga cgcgttcacc tcggagacga gcatcgatgc cgtgacggag    2100
aactcgggtg tttga                                                      2115
```

<210> SEQ ID NO 24
<211> LENGTH: 563
<212> TYPE: PRT
<213> ORGANISM: Thermoascus aurantiacus

<400> SEQUENCE: 24

```
Met Ser Phe Val Asn Ser Leu Phe Leu Phe Asn Val Leu Ala Pro
1               5                   10                  15

Ala Val Tyr Ser Ile Pro His Pro Gly His Leu Ser Lys Arg Cys Thr
            20                  25                  30

Asn Ser Ala Thr Asp Arg Ser Cys Trp Gly Asp Phe Asp Leu Ser Thr
        35                  40                  45

Asn Tyr Tyr Glu Val Ser Pro Asp Thr Gly Val Thr Arg Glu Tyr Trp
    50                  55                  60

Leu Asp Ile Thr Asn Thr Thr Ala Ala Pro Asp Gly Ile Glu Arg Ile
65                  70                  75                  80

Val Leu Thr Val Asn Gly Thr Val Pro Gly Pro Thr Leu Tyr Ala Asp
                85                  90                  95

Trp Gly Asp Thr Val Val Val His Val Thr Asn Ser Leu Ser Ala Asn
            100                 105                 110

Gly Thr Gly Ile His Phe His Gly Ile Arg Gln Asn Tyr Thr Asn Gln
        115                 120                 125

Met Asp Gly Val Pro Ser Ile Thr Gln Cys Pro Val Ala Pro Gly Asp
    130                 135                 140

Ser Ile Thr Tyr Thr Trp Lys Ala Thr Gln Tyr Gly Thr Thr Trp Tyr
145                 150                 155                 160

His Ser His Phe Ser Leu Gln Ala Trp Glu Gly Val Phe Gly Gly Ile
                165                 170                 175

Val Ile Asn Gly Pro Ala Ser Ala Asn Tyr Asp Glu Asp Leu Gly Pro
            180                 185                 190

Leu Phe Leu Ser Asp Trp Thr His Glu Thr Thr Cys Ala Leu Phe Thr
        195                 200                 205

Gln Ala Glu Tyr Ser Gly Pro Pro Thr Met Asp Asn Gly Leu Ile Asn
    210                 215                 220

Gly Thr Asn Ile Tyr Asn Asn Ser Gly Thr Ile Val Gly Ser Arg Phe
225                 230                 235                 240

Gln Thr Thr Phe Glu Ser Gly Lys Ser Tyr Arg Leu Arg Leu Ile Asn
                245                 250                 255

Gly Ala Asn Asp Ser His Phe Lys Phe Ser Ile Asp Asn His Thr Met
            260                 265                 270

Thr Val Ile Ala Asn Asp Leu Val Pro Ile Val Pro Tyr Glu Thr Asn
        275                 280                 285

Val Leu Asn Ile Gly Ile Gly Gln Arg Tyr Asp Ile Ile Val Asn Ala
    290                 295                 300

Thr Ala Thr Pro Gly Asn Tyr Trp Met Arg Ala Ile Pro Gln Ser Cys
```

```
              305                 310                 315                 320
Ser Asp Asn Ala Asn Gly Asp Asn Ile Arg Gly Ile Arg Tyr Asp
                325                 330                 335

Ala Ser Ser Thr Asp Asp Pro Thr Ser Thr Ala Trp Asp Gln Glu Val
                340                 345                 350

Ser Asp Cys Glu Asp Glu Asp Ser Ser Asn Leu Val Pro Tyr Leu Ser
                355                 360                 365

Leu Asp Ala Ala Glu Gly Asp Trp Leu Ala Ser Leu Thr Ala Thr Val
        370                 375                 380

Lys Gly Thr Pro Phe Lys Trp Tyr Leu Asn Asp Thr Thr Met Ala Val
385                 390                 395                 400

Asn Trp Thr Ser Pro Thr Leu Lys Gln Ile Tyr Leu Asn Glu Thr Asp
                405                 410                 415

Trp Glu Asp Ser Glu Ala Val Tyr Glu Leu Thr Ala Asp Glu Trp
                420                 425                 430

Ala Tyr Ile Ile Ile Gln Ser Ser Ala Gly Ala Ala His Pro Ile His
                435                 440                 445

Leu His Gly His Asp Phe Asn Val Leu Ala Ser Gly Ser Gly Thr Phe
        450                 455                 460

Asp Thr Ser Thr Ser Leu Ser Ser Leu Asn Leu Ser Asn Pro Pro Arg
465                 470                 475                 480

Arg Asp Val Ala Leu Leu Pro Ala Asn Gly Tyr Leu Val Leu Ala Phe
                485                 490                 495

Lys Ala Asp Asn Pro Gly Ala Trp Leu Met His Cys His Ile Gly Trp
                500                 505                 510

His Thr Glu Glu Gly Phe Ser Leu Gln Ile Val Glu Arg Met Asp Glu
            515                 520                 525

Phe Arg Ser Met Ile Asp Tyr Asp Thr Leu Asn Gln Thr Cys Thr Asn
                530                 535                 540

Trp Asp Ala Phe Thr Ser Glu Thr Ser Ile Asp Ala Val Thr Glu Asn
545                 550                 555                 560

Ser Gly Val

<210> SEQ ID NO 25
<211> LENGTH: 2111
<212> TYPE: DNA
<213> ORGANISM: Thermoascus aurantiacus

<400> SEQUENCE: 25
atggcaccac taaggtcgct tctggcgctt tgtgccgcta ccttggcgtc ttcagtatac      60
tctgcctttg ttccatttga gctgcgcctc acatgggaag tgggtgcacc gaatggtgaa     120
ccgagggaga tgattttcat gaatggccag tttcccggtc agaactgag gatcgatcag      180 ggtgacgagg ttgaggtctg tctgagtccc aagaacaccg cgtagaaaca tcatgctgac     240
tgtatttaaa gttaccgtc cataaccacc tcccttttaa tacgagcgtt catttccatg      300
gtatcgagta tgatttgccc atattaatcc tcatatgtgg ctacgcatat taactgtggg     360
taggcaatac aagactccat ggtccgatgg cgtccctggc ctcacacaaa agccaattca     420
gcctggagaa acattcgttt atagatggac tgctactcaa tacggcacat actggttcgg     480
caccattcca cggcaaatta tttcgcgtcg tggctgacaa ctaaacttta ggtaccatgc     540
ccactcgcgc ggtaccgtag ccgatgggct acggcgca atttggatca agtgaagctc      600
ccagttatac atactatggt caatgtacac tgacaacagg catagaccga agcctggtac    660
```

```
cccgacgccc tttggattga tatcccagga tgaggaggac atccaagcca tgcttcgtgc    720
ggaggccaat ccccgtctgg tcgtgctgtc ggactgggag cacctaactt ccgaacaata    780
catgtattac caggaatact ccgggcttga cttattgtat gttgaatatc cctggttaaa    840
atttaattac taaacactatg atagttgcgt tgacagcgtc ttgatcaatg cagaggagc    900
catctactgc ctaagcgctg atgaactcta cagctacgag actccatacc ttaaggccgc    960
catcgacaat ctcaatctta ctgacaaggg gtacgttcta gaaagaaaa agctgttagc   1020
aaaccccca ttaacattta ttatacagat gctatccaaa catttcgaa acccagggga   1080
actactcgta tgacgagtct aaggtccccc caggcgtcaa ctcgggttgt cgtccaaaca   1140
aaggactcca tgaagttttc gaagtggatg ccagcgaagg ttgggcgagc ttcaagttca   1200
tcagtgcggc tttcatgaag tcccttgttg tttcgattga cgagcacccg atgtggatct   1260
acgaggtcga tggacgatac attgagccac agctcgttca ttctttcccc atttacaacg   1320
gagagcgcta ttccgccatg atcaagcttg acaagctgcc caagaactac acgatgagaa   1380
tcccggacac gaacgtcgac cagatcatct ccggatttgc caccctctcc tacatgggcg   1440
gacaggatct cgggccatca aagccgtacg taaactacgg aggcctgaat gtctcagctg   1500
acgttgtctc actgaatgtg aacacgcttc cgccttaccc taatatcaag cccgcaaaga   1560
cagctgatat catgtacaat cttaccatgg gccggttcaa ctcgtcgtac acgtggaccc   1620
tggatggcac cgacctctac gacgtgaacg ccaacgccga taccccgatc ctattcgatc   1680
tgagcgcgag ggataacttg gccaagaacc tcacgctcgt caccttaaac ggcacctggg   1740
tcgatctgat cctgcagctg gcatatttcc ccaaacacgcc gagcatccaa gctcctcacg   1800
tcatccacaa acattcgaac aaggccttca tgatcggttc cggtgacgga ttcttcaact   1860
ggaccagcgt caacgaggcg attcgggagt cgcctcggaa tttcaacctc gagaacccga   1920
actataggga taccttcgtt accaacggcc ccttcggtcc cacgtggatg gtgctgcggt   1980
accaggtcgt caaccccggt cccttcctcc ttcactgcca tatcgagact catttgaccg   2040
gtgggatggg tgttgcgttg cttgatggag tggaccagtg gcctaaagtt cctccggagt   2100
atgccatctg a                                                       2111
```

<210> SEQ ID NO 26
<211> LENGTH: 593
<212> TYPE: PRT
<213> ORGANISM: Thermoascus aurantiacus

<400> SEQUENCE: 26

Met Ala Pro Leu Arg Ser Leu Leu Ala Leu Cys Ala Ala Thr Leu Ala
1               5                   10                  15

Ser Ser Val Tyr Ser Ala Phe Val Pro Phe Glu Leu Arg Leu Thr Trp
            20                  25                  30

Glu Val Gly Ala Pro Asn Gly Glu Pro Arg Glu Met Ile Phe Met Asn
        35                  40                  45

Gly Gln Phe Pro Gly Pro Leu Arg Ile Asp Gln Gly Asp Glu Val
    50                  55                  60

Glu Phe Thr Val His Asn His Leu Pro Phe Asn Thr Ser Val His Phe
65                  70                  75                  80

His Gly Ile Glu Gln Tyr Lys Thr Pro Trp Ser Asp Gly Val Pro Gly
                85                  90                  95

Leu Thr Gln Lys Pro Ile Gln Pro Gly Glu Thr Phe Val Tyr Arg Trp
            100                 105                 110

-continued

```
Thr Ala Thr Gln Tyr Gly Thr Tyr Trp Tyr His Ala His Ser Arg Gly
            115                 120                 125
Thr Val Ala Asp Gly Leu Tyr Gly Ala Ile Trp Ile Lys Pro Lys Pro
    130                 135                 140
Gly Thr Pro Thr Pro Phe Gly Leu Ile Ser Gln Asp Glu Glu Asp Ile
145                 150                 155                 160
Gln Ala Met Leu Arg Ala Glu Ala Asn Pro Arg Leu Val Val Leu Ser
                165                 170                 175
Asp Trp Glu His Leu Thr Ser Glu Gln Tyr Met Tyr Tyr Gln Glu Tyr
                180                 185                 190
Ser Gly Leu Asp Leu Phe Cys Val Asp Ser Val Leu Ile Asn Gly Arg
            195                 200                 205
Gly Ala Ile Tyr Cys Leu Ser Ala Asp Glu Leu Tyr Ser Tyr Glu Thr
            210                 215                 220
Pro Tyr Leu Lys Ala Ala Ile Asp Asn Leu Asn Leu Thr Asp Lys Gly
225                 230                 235                 240
Cys Tyr Pro Asn Ile Phe Glu Thr Gln Gly Asn Tyr Ser Tyr Asp Glu
                245                 250                 255
Ser Lys Val Pro Pro Gly Val Asn Ser Gly Cys Arg Pro Asn Lys Gly
                260                 265                 270
Leu His Glu Val Phe Glu Val Asp Ala Ser Glu Gly Trp Ala Ser Phe
            275                 280                 285
Lys Phe Ile Ser Ala Ala Phe Met Lys Ser Leu Val Val Ser Ile Asp
            290                 295                 300
Glu His Pro Met Trp Ile Tyr Glu Val Asp Gly Arg Tyr Ile Glu Pro
305                 310                 315                 320
Gln Leu Val His Ser Phe Pro Ile Tyr Asn Gly Glu Arg Tyr Ser Ala
                325                 330                 335
Met Ile Lys Leu Asp Lys Leu Pro Lys Asn Tyr Thr Met Arg Ile Pro
                340                 345                 350
Asp Thr Asn Val Asp Gln Ile Ile Ser Gly Phe Ala Thr Leu Ser Tyr
            355                 360                 365
Met Gly Gly Gln Asp Leu Gly Pro Ser Lys Pro Tyr Val Asn Tyr Gly
    370                 375                 380
Gly Leu Asn Val Ser Ala Asp Val Val Ser Leu Asn Val Asn Thr Leu
385                 390                 395                 400
Pro Pro Tyr Pro Asn Ile Lys Pro Ala Lys Thr Ala Asp Ile Met Tyr
                405                 410                 415
Asn Leu Thr Met Gly Arg Phe Asn Ser Ser Tyr Thr Trp Thr Leu Asp
                420                 425                 430
Gly Thr Asp Leu Tyr Asp Val Asn Ala Asn Ala Asp Thr Pro Ile Leu
            435                 440                 445
Phe Asp Leu Ser Ala Arg Asp Asn Leu Ala Lys Asn Leu Thr Leu Val
    450                 455                 460
Thr Leu Asn Gly Thr Trp Val Asp Leu Ile Leu Gln Leu Gly Ile Phe
465                 470                 475                 480
Pro Asn Thr Pro Ser Ile Gln Ala Pro His Val Ile His Lys His Ser
                485                 490                 495
Asn Lys Ala Phe Met Ile Gly Ser Gly Asp Gly Phe Phe Asn Trp Thr
                500                 505                 510
Ser Val Asn Glu Ala Ile Arg Glu Ser Pro Arg Asn Phe Asn Leu Glu
            515                 520                 525
Asn Pro Asn Tyr Arg Asp Thr Phe Val Thr Asn Gly Pro Phe Gly Pro
```

Thr Trp Met Val Leu Arg Tyr Gln Val Val Asn Pro Gly Pro Phe Leu
545                 550                 555                 560

Leu His Cys His Ile Glu Thr His Leu Thr Gly Gly Met Gly Val Ala
            565                 570                 575

Leu Leu Asp Gly Val Asp Gln Trp Pro Lys Val Pro Pro Glu Tyr Ala
        580                 585                 590

Ile

<210> SEQ ID NO 27
<211> LENGTH: 1967
<212> TYPE: DNA
<213> ORGANISM: Corynascus thermophilus

<400> SEQUENCE: 27

| | |
|---|---|
| atgtttcgac cggccttgct cccgctggcg cgattgctag tgcatctggc cagattctcc | 60 |
| agggcagaga ctgtgaccta cgactggaat gtgacttggg tctgggcagc cccagacggc | 120 |
| tttggggaggc ccgtcatcgg aatcaacaac cagtggccat gcccttccat cgacgctacc | 180 |
| gcgggcgacg tggtcgtgat aaacttgagc aaccatctgg ggaaccagac dacaggccta | 240 |
| cactttcacg gtatacacca gatacagacg gccgacatgg acggcccgag cggcgtcact | 300 |
| cagtgcggga taccacccgg ctcgacagtc aagtaccgat tcacggtcga tgcgccaggg | 360 |
| agttttggt gtatgcccga ttgcgtctcc gcgcatccac aaccctggtg gacactgaca | 420 |
| aacagaggtc agatcattcc cataacatgg ggcagtatcc tgacgggctg cgcggcccct | 480 |
| tgattgtgcg ggatccggac gatccttaca agatgagta cgacgaggag cacatcttga | 540 |
| ctgtctcgga ttggtaagag ttcgaaagac ctggttctcc tggagctcga agaagatatt | 600 |
| cattgcctgc aggtaccaca acgacagcat cacctcggtc cggaacatgc tcaacccgtc | 660 |
| caacacgcgc ttcttgcccc cagtaccgga acaacatcacg gtaaacgaag ggcagggact | 720 |
| acatatcaaa ttcgccaagg gcaagaggta tcgaatccgc atgataagtt tttcggcctt | 780 |
| tggtgccgcc atggttcact ttgactcgca cacaatgaac gtgatcgcga tcgacggcgc | 840 |
| atacgtcaag aaggaggatg catatcagct gaggatcgcc cctgcgcagc gctacgacgt | 900 |
| cttgctctcg ccgagtgata gtgacgaggg aaactacccc ttcctggtct ctctcgacat | 960 |
| caaccgggac tggacaaact cgtccgagga gatggtatgg ccgcacaatt acacgggcta | 1020 |
| cctcgtcatg gacgaatccc aaccgctcga caaggtcgac gtggtggaca aatggcagcc | 1080 |
| ggcggacgag gccggttcc agccctacga tggggccgcg gcctacggca cgtaccaaaa | 1140 |
| attgatcaag ctcgactttg ccttctgcct cgaccagaac ggttaccctc gctcatgctt | 1200 |
| caacaacgtg acctacatca cccaacgggt cccgacgctc tacagcgccg ccacgacagg | 1260 |
| cgagtccaac acgaatcccg tcatctacgg ccaggtcaac ccttcatcg tcgactacga | 1320 |
| cgacacgatc cagatcgtcg tcaacaacat cgacgcggct tctcatccct tccacctgca | 1380 |
| cggccaccac ttccaggtgc tgcatcgcgc cccgggctgg gcggggaact ggacggggcg | 1440 |
| cgacgagaat tacacggcca acccgccgat gcgggacacc atcaccgtcc tgcccaactc | 1500 |
| gtacgccgtc gtgcgcttcc gggcgaacaa cccgggcgtc tggctgttcc actgccacat | 1560 |
| cgagtggcac gtcgagatgg gcctgacggc gaccatcatc gaggccccg accgcctgcg | 1620 |
| gaacatgacc ttccccgacg accacatcga cgcctgcaag aagaccggca cgccgtacga | 1680 |
| gggaaacgcg gccgggaata cgcagaacgt gaccgacacc acgggcttca tcactgtgcc | 1740 |

-continued

```
gccgactact tataacgggt gcgtccttcg ttttcctcgt tttgcgacgt caacaccttg      1800
tgacgttcat aacaatgcgg ctgtgctgac aaccaataca tctcaacagc tcggcgtaca      1860
cgccctcggg cgccgcatct cagaggaagc gtcatgagcc ggcaccgtca gtgctcggga      1920
ggagcgtgat atcactcgcc aagctcggct ggttatggca tcattaa                   1967
```

<210> SEQ ID NO 28
<211> LENGTH: 584
<212> TYPE: PRT
<213> ORGANISM: Corynascus thermophilus

<400> SEQUENCE: 28

```
Met Phe Arg Pro Ala Leu Leu Pro Leu Ala Arg Leu Leu Val His Leu
1               5                   10                  15

Ala Arg Phe Ser Arg Ala Glu Thr Val Thr Tyr Asp Trp Asn Val Thr
            20                  25                  30

Trp Val Trp Ala Ala Pro Asp Gly Phe Gly Arg Pro Val Ile Gly Ile
        35                  40                  45

Asn Asn Gln Trp Pro Cys Pro Ser Ile Asp Ala Thr Ala Gly Asp Val
    50                  55                  60

Val Val Ile Asn Leu Ser Asn His Leu Gly Asn Gln Thr Thr Gly Leu
65                  70                  75                  80

His Phe His Gly Ile His Gln Ile Gln Thr Ala Asp Met Asp Gly Pro
                85                  90                  95

Ser Gly Val Thr Gln Cys Gly Ile Pro Pro Gly Ser Thr Val Lys Tyr
            100                 105                 110

Arg Phe Thr Val Asp Ala Pro Gly Ser Phe Trp Tyr His Ser His Asn
        115                 120                 125

Met Gly Gln Tyr Pro Asp Gly Leu Arg Gly Pro Leu Ile Val Arg Asp
    130                 135                 140

Pro Asp Asp Pro Tyr Lys Asp Glu Tyr Asp Glu His Ile Leu Thr
145                 150                 155                 160

Val Ser Asp Trp Tyr His Asn Asp Ser Ile Thr Ser Val Arg Asn Met
                165                 170                 175

Leu Asn Pro Ser Asn Thr Arg Phe Leu Pro Pro Val Pro Asp Asn Ile
            180                 185                 190

Thr Val Asn Glu Gly Gln Gly Leu His Ile Lys Phe Ala Lys Gly Lys
        195                 200                 205

Arg Tyr Arg Ile Arg Met Ile Ser Phe Ser Ala Phe Gly Ala Ala Met
    210                 215                 220

Val His Phe Asp Ser His Thr Met Asn Val Ile Ala Ile Asp Gly Ala
225                 230                 235                 240

Tyr Val Lys Lys Glu Asp Ala Tyr Gln Leu Arg Ile Ala Pro Ala Gln
                245                 250                 255

Arg Tyr Asp Val Leu Leu Ser Pro Ser Asp Ser Asp Glu Gly Asn Tyr
            260                 265                 270

Pro Phe Leu Val Ser Leu Asp Ile Asn Arg Asp Trp Thr Asn Ser Ser
        275                 280                 285

Glu Glu Met Val Trp Pro His Asn Tyr Thr Gly Tyr Leu Val Met Asp
    290                 295                 300

Glu Ser Gln Pro Leu Asp Lys Val Asp Val Val Asp Lys Trp Gln Pro
305                 310                 315                 320

Ala Asp Glu Ala Arg Phe Gln Pro Tyr Asp Gly Ala Ala Ala Tyr Gly
                325                 330                 335
```

```
Thr Tyr Gln Lys Leu Ile Lys Leu Asp Phe Ala Phe Cys Leu Asp Gln
            340                 345                 350

Asn Gly Tyr Pro Arg Ser Cys Phe Asn Val Thr Tyr Ile Thr Gln
        355                 360                 365

Arg Val Pro Thr Leu Tyr Ser Ala Ala Thr Thr Gly Glu Ser Asn Thr
    370                 375                 380

Asn Pro Val Ile Tyr Gly Gln Val Asn Pro Phe Ile Val Asp Tyr Asp
385                 390                 395                 400

Asp Thr Ile Gln Ile Val Val Asn Asn Ile Asp Ala Ala Ser His Pro
                405                 410                 415

Phe His Leu His Gly His His Phe Gln Val Leu His Arg Ala Pro Gly
            420                 425                 430

Trp Ala Gly Asn Trp Thr Gly Arg Asp Glu Asn Tyr Thr Ala Asn Pro
        435                 440                 445

Pro Met Arg Asp Thr Ile Thr Val Leu Pro Asn Ser Tyr Ala Val Val
    450                 455                 460

Arg Phe Arg Ala Asn Asn Pro Gly Val Trp Leu Phe His Cys His Ile
465                 470                 475                 480

Glu Trp His Val Glu Met Gly Leu Thr Ala Thr Ile Ile Glu Ala Pro
                485                 490                 495

Asp Arg Leu Arg Asn Met Thr Phe Pro Asp Asp His Ile Asp Ala Cys
            500                 505                 510

Lys Lys Thr Gly Thr Pro Tyr Glu Gly Asn Ala Ala Gly Asn Thr Gln
        515                 520                 525

Asn Val Thr Asp Thr Thr Gly Phe Ile Thr Val Pro Pro Thr Thr Tyr
    530                 535                 540

Asn Gly Ser Ala Tyr Thr Pro Ser Gly Ala Ala Ser Gln Arg Lys Arg
545                 550                 555                 560

His Glu Pro Ala Pro Ser Val Leu Gly Arg Ser Val Ile Ser Leu Ala
                565                 570                 575

Lys Leu Gly Trp Leu Trp His His
            580

<210> SEQ ID NO 29
<211> LENGTH: 1990
<212> TYPE: DNA
<213> ORGANISM: Corynascus thermophilus

<400> SEQUENCE: 29
atggctgcaa ggtgtcttgg ccgcctcgtg gccctactgg ccagcacggc ctacctcgca      60
catggccagc taacgcagga acaaaccaat gggtaaggtt ccatggtaga atcctactat     120
cttttcatga gcccgtatgg agtaccaaac gcgcggaacg ctgatcgctg atgacaaatg     180
ttacagtaac tgccagtggg gacaaataga tgcaccgctg taccccgact ttttgacaga     240
taacgtaagc cgcactctgc tcgggtgtag tgatgatttg cggcattggt actgatacaa     300
gggctgcaat gacgaacagc cgttgcctga cggcacaccg tggggcatcc gtgacgacta     360
tcgcccgacc tccgataaca tccccgagac gggcgtgatc cgctactacg acttcgacat     420
ccgtcgagga acccttgctc ccgacgggtt cgtgaagaag gcatttttcg tcaacggaca     480
gtttcccggc ccgaccattg aggcgaactg gggcgactgg atcgaggtcc gggtgcacaa     540
caacatcaac gagacggatg acggcaagac ggaggggacg gcgatccact tccatggcat     600
gctccagaag ggcacgcagt ggttcgatgg cgtgccgggc gtgacgcagt gccccatcgc     660
cccgaactcc tccttcacct accggttccg ggccgacgtg tacgggtcgt cgtggtggca     720
```

-continued

```
ctctcactac tcggcccagt acactgccgg cgtctggggg cccatgatca tctacggtcc      780
taagcatgtg gactacgacg tcgatctggg tccgattatg ctcggcgatt actaccacaa      840
ggagtatcac gatgtcgttg ctgccgctgc cagcaactcg accgatttcg acgtctatgt      900
cccctggtcc gacaacagct tgatcaacgg caagaacagt tataactgct cgcttgctcc      960
cgccggctcg acatgctacc cggatgcgcc gctctcccaa ttccagttcc agcccggcaa     1020
gacgcaccgt ctgcgtctca tgaacacggg cgctgcggcg ctcatccact tcagcattga     1080
cgggcaccag atgcaggtca tcgccaacga ctttgagcca ctagtgccct acacggccga     1140
ctacatcacc ctccatgtcg gccaacgcgc cgacattctg gtcaaggctg acgcggaccc     1200
cagtcaaacg tactggatga ggtcgactat ctcgctcaac tgctccgtca cattatcc       1260 cgaggggagg gcaatcatct cctacacggg aaatactaac ccgacgacgc cgacaagcac     1320
catcaacccg gtggctgctg ccgcggacga gaagtcgttc ctctgcaaga acgatgactt     1380
gaacaagacg gtgccctact acccggagcc tgtggatccc aacccggaca cggtcgagac     1440
catcctcgtg gatctcctga ctaacgccac gggcaaccac gtctggatca tgaacaacgt     1500
cacgcagttt accaactacc accaccccagt cctgctccag gccttccacc agaactttac     1560
cttcaccgac ccgatggcta acgtgtacaa ctttggcacc aacaagaccg tccgcatcgt     1620
cctcaatacc gtctaccaga gcgcccaccc gatgcacatc cacggacacg ccttccaggt     1680
cctcgccgag ggccccggtg cctgggacgg ccacaccatt gtcaatcccc agaatccact     1740
gcgtcgcgat acccatatcc agcggcggta cggccacctc gtcatccagt tcaagaccga     1800
caacccgggc gtatggagct accactgcca tatcgcctgg cacgcgagca tgggcttcac     1860
tatcgttttc ctcgagcacc ctgaagagct ggcaaacacc actgttccct tcatcatgga     1920
ccagacatgt gtggattggc acgagtggac caagaaccac cccgtcgacc agattgattc     1980
tggaatttga                                                           1990
```

<210> SEQ ID NO 30
<211> LENGTH: 606
<212> TYPE: PRT
<213> ORGANISM: Corynascus thermophilus

<400> SEQUENCE: 30

Met Ala Ala Arg Cys Leu Gly Arg Leu Val Ala Leu Leu Ala Ser Thr
1               5                   10                  15

Ala Tyr Leu Ala His Gly Gln Leu Thr Gln Glu Gln Thr Asn Gly Asn
            20                  25                  30

Cys Gln Trp Gly Gln Ile Asp Ala Pro Leu Tyr Pro Asp Phe Leu Thr
        35                  40                  45

Asp Asn Pro Leu Pro Asp Gly Thr Pro Trp Gly Ile Arg Asp Asp Tyr
    50                  55                  60

Arg Pro Thr Ser Asp Asn Ile Pro Glu Thr Gly Val Ile Arg Tyr Tyr
65                  70                  75                  80

Asp Phe Asp Ile Arg Arg Gly Thr Leu Ala Pro Asp Gly Phe Val Lys
                85                  90                  95

Lys Gly Ile Phe Val Asn Gly Gln Phe Pro Gly Pro Thr Ile Glu Ala
            100                 105                 110

Asn Trp Gly Asp Trp Ile Glu Val Arg Val His Asn Asn Ile Asn Glu
        115                 120                 125

Thr Asp Asp Gly Lys Thr Glu Gly Thr Ala Ile His Phe His Gly Met
    130                 135                 140

```
Leu Gln Lys Gly Thr Gln Trp Phe Asp Gly Val Pro Gly Val Thr Gln
145                 150                 155                 160

Cys Pro Ile Ala Pro Asn Ser Ser Phe Thr Tyr Arg Phe Arg Ala Asp
            165                 170                 175

Val Tyr Gly Ser Ser Trp Trp His Ser His Tyr Ser Ala Gln Tyr Thr
                180                 185                 190

Ala Gly Val Trp Gly Pro Met Ile Ile Tyr Gly Pro Lys His Val Asp
            195                 200                 205

Tyr Asp Val Asp Leu Gly Pro Ile Met Leu Gly Asp Tyr Tyr His Lys
        210                 215                 220

Glu Tyr His Asp Val Val Ala Ala Ala Ser Asn Ser Thr Asp Phe
225                 230                 235                 240

Asp Val Tyr Val Pro Trp Ser Asp Asn Ser Leu Ile Asn Gly Lys Asn
                245                 250                 255

Ser Tyr Asn Cys Ser Leu Ala Pro Ala Gly Ser Thr Cys Tyr Pro Asp
            260                 265                 270

Ala Pro Leu Ser Gln Phe Gln Phe Gln Pro Gly Lys Thr His Arg Leu
        275                 280                 285

Arg Leu Met Asn Thr Gly Ala Ala Ala Leu Ile His Phe Ser Ile Asp
290                 295                 300

Gly His Gln Met Gln Val Ile Ala Asn Asp Phe Glu Pro Leu Val Pro
305                 310                 315                 320

Tyr Thr Ala Asp Tyr Ile Thr Leu His Val Gly Gln Arg Ala Asp Ile
                325                 330                 335

Leu Val Lys Ala Asp Ala Asp Pro Ser Gln Thr Tyr Trp Met Arg Ser
            340                 345                 350

Thr Ile Ser Leu Asn Cys Ser Val Thr His Tyr Pro Glu Gly Arg Ala
        355                 360                 365

Ile Ile Ser Tyr Thr Gly Asn Thr Asn Pro Thr Thr Pro Thr Ser Thr
        370                 375                 380

Ile Asn Pro Val Ala Ala Ala Asp Glu Lys Ser Phe Leu Cys Lys
385                 390                 395                 400

Asn Asp Asp Leu Asn Lys Thr Val Pro Tyr Tyr Pro Glu Pro Val Asp
                405                 410                 415

Pro Asn Pro Asp Thr Val Glu Thr Ile Leu Val Asp Leu Leu Thr Asn
            420                 425                 430

Ala Thr Gly Asn His Val Trp Ile Met Asn Asn Val Thr Gln Phe Thr
        435                 440                 445

Asn Tyr His His Pro Val Leu Leu Gln Ala Phe His Gln Asn Phe Thr
    450                 455                 460

Phe Thr Asp Pro Met Ala Asn Val Tyr Asn Phe Gly Thr Asn Lys Thr
465                 470                 475                 480

Val Arg Ile Val Leu Asn Thr Val Tyr Gln Ser Ala His Pro Met His
                485                 490                 495

Ile His Gly His Ala Phe Gln Val Leu Ala Glu Gly Pro Gly Ala Trp
            500                 505                 510

Asp Gly His Thr Ile Val Asn Pro Gln Asn Pro Leu Arg Arg Asp Thr
        515                 520                 525

His Ile Gln Arg Arg Tyr Gly His Leu Val Ile Gln Phe Lys Thr Asp
    530                 535                 540

Asn Pro Gly Val Trp Ser Tyr His Cys His Ile Ala Trp His Ala Ser
545                 550                 555                 560
```

```
                Met Gly Phe Thr Ile Val Phe Leu Glu His Pro Glu Glu Leu Ala Asn
                            565                 570                 575

Thr Thr Val Pro Phe Ile Met Asp Gln Thr Cys Val Asp Trp His Glu
                            580                 585                 590

Trp Thr Lys Asn His Pro Val Asp Gln Ile Asp Ser Gly Ile
                            595                 600             605

<210> SEQ ID NO 31
<211> LENGTH: 2355
<212> TYPE: DNA
<213> ORGANISM: Corynascus thermophilus

<400> SEQUENCE: 31
atgaaaccgt tcatcagcgc cgcggcgctc ttggtgggcg tcctcacctc gggcgctgct      60
gctgcccctc cgtccacccc cgagcagcgc gacctgctcg cggccgccac catcgaggag     120
agaaaggagg aggccgtgca gcctcgcctg aagagctgca actcggccaa ggaccggtcg     180
tgctgggtcg aggggtacac gatccagacc gactgggaac aggacgtccc ggacacgggc     240
gtcattcggc gggtgagtgg cgcccctcct ctctctttcc gcctcggcgg ggtttgggca     300
tggccacatg ctagacgggg ggctgacatg cgggtagtac actctggaaa tcgttgaggt     360
caacaacttc caaggacctg acggcgtcat caaggagaag gtcatgttgg ttaacagtaa     420
gtgaccttgc gagagaaaga gagagagaga caggaagcga gaggagactg accaagcatt     480
cgcctgcaga tagctttatc ggtatgtctc actgcctccg gcagcccaa acactcactc      540 gggaagcgtt tcgaagggta ggttaggtag ccaggaatac tgaccgggcc cgaccaattt     600
acaggaccga ccctctacgc ggactggggc gacaggttcg aggtgaccgt catcaacagc     660
ctcgaggcca cgggtacgt ctgttgttcc gcttgcactc cctcctgttc gactcggtcg      720
cgctaattac aatcaaaaaa gcacgtcgat ccattggcac ggactgcacc agaagggcgc     780
caacattcac gacggcacca acggtatcac cgagtgcccg atccccccg gaggaagcaa      840 ggtatacaag ttcagggcga cccagtacgg gacggcctgg taccactctc acttctcggc     900
ccagtacggc aacggcgtcg ccggcgtgat tcagatcaac ggcccgacct cggccgagta     960
cgacatcgat ttgggcgtgt ccccgatcac ggactactac tggtctggtg ccgatcaact    1020
atacgagcag accttgcacg ccccggcgcc ctttagtgac aacgtcctct tcaacggcac    1080
gggcaagaac ccgttgacgg gcgagggcga gttcgccaag gtgacgctca cgccgggcaa    1140
gaagcaccgc ctgcgcctcg tcaacacggg cgtcgagaac cacttccagc tctcgctcgt    1200
caaccatcaa tttaccatca tcggcgccga catggtgcct gtccacccga ggacggtcga    1260
cagcctcttc ctcggcgtcg gccagcgcta cgacatcatc atcgaagcca accagacgcc    1320
cggcaactac tggttcaacg ccaccttcgg tggcgaaggc gaatgcggca cgtccaacaa    1380
caagtacccg ccgccatct tccactactc cagcgccccc gacgccctgc ccaccgacga     1440
gggcgtggcc ccgattgacc acaactgcct cgacctggac gacctcgagc catcgtgtc    1500 ggaagacgtg cccatcagcg gcttcacgaa cgtgcacgag gacacgctcg acgtccacct    1560
cgagacccac cccatgttcg tctggcagat caacggcagc gccgtcaacg tcgactggag    1620
cgacccgctc atcgactacg tcatccagca gaacaccagt ttcccgcccg agtacaacgt    1680
catcgagctg gcccaggcca accaggtgag tgcgggcgac gtctctgcaa cgtactcgtt    1740
cgaaggtcga aggccgatcc aagactgacc gctatcgcag tggacctatt ggttgatcca    1800
gaacgacccc ggcgccaccc tcagcccgcc gcaccccatg caccttcatg tatgttcata    1860
```

```
tccccccctc ccctccccc cgcctccgga aaaaaaaga aatccagagt cgaatgagta    1920
cttaccacct tcacaaaaca gggccacgac ttctacatcc tgggccgctc gcccggcgtg    1980
tcgcccgcgt ccaggcagct gttccgcttc gacccgaaga aggacttcca gcgtctgacc    2040
acgcacaagc cgatgaagcg cgacacggcc atgctccccg gcttcggctg gctgctgatc    2100
gccttccgca ccgacaaccc gggcgcctgg gtcttccact gccacatcgc ctggcacgtc    2160
tcgggcggct tcagcgtcac ctacctcgag cgccccgacg agctgcgcca gtccctctcg    2220
caggaggaca tcgacgacca caaccgcgtc tgcggcgagt ggcgcgagta ctggcccacc    2280
agccccttcc ccaagctcga ctcgggtctc cgccaccgct gggtcgagca gagcgagtgg    2340
tcgatcaagg tttaa                                                    2355
```

<210> SEQ ID NO 32
<211> LENGTH: 619
<212> TYPE: PRT
<213> ORGANISM: Corynascus thermophilus

<400> SEQUENCE: 32

```
Met Lys Pro Phe Ile Ser Ala Ala Ala Leu Leu Val Gly Val Leu Thr
1               5                   10                  15

Ser Gly Ala Ala Ala Pro Pro Ser Thr Pro Glu Gln Arg Asp Leu
            20                  25                  30

Leu Ala Ala Thr Ile Glu Glu Arg Lys Glu Ala Val Gln Pro
        35                  40                  45

Arg Leu Lys Ser Cys Asn Ser Ala Lys Asp Arg Ser Cys Trp Val Glu
    50                  55                  60

Gly Tyr Thr Ile Gln Thr Asp Trp Glu Gln Asp Val Pro Asp Thr Gly
65              70                  75                  80

Val Ile Arg Arg Tyr Thr Leu Glu Ile Val Glu Val Asn Asn Phe Gln
                85                  90                  95

Gly Pro Asp Gly Val Ile Lys Glu Lys Val Met Leu Val Asn Asn Ser
            100                 105                 110

Phe Ile Gly Pro Thr Leu Tyr Ala Asp Trp Gly Asp Arg Phe Glu Val
        115                 120                 125

Thr Val Ile Asn Ser Leu Glu Ala Asn Gly Thr Ser Ile His Trp His
    130                 135                 140

Gly Leu His Gln Lys Gly Ala Asn Ile His Asp Gly Thr Asn Gly Ile
145                 150                 155                 160

Thr Glu Cys Pro Ile Pro Pro Gly Gly Ser Lys Val Tyr Lys Phe Arg
                165                 170                 175

Ala Thr Gln Tyr Gly Thr Ala Trp Tyr His Ser His Phe Ser Ala Gln
            180                 185                 190

Tyr Gly Asn Gly Val Ala Gly Val Ile Gln Ile Asn Gly Pro Thr Ser
        195                 200                 205

Ala Glu Tyr Asp Ile Asp Leu Gly Val Phe Pro Ile Thr Asp Tyr Tyr
    210                 215                 220

Trp Ser Gly Ala Asp Gln Leu Tyr Glu Gln Thr Leu His Ala Pro Ala
225                 230                 235                 240

Pro Phe Ser Asp Asn Val Leu Phe Asn Gly Thr Gly Lys Asn Pro Leu
                245                 250                 255

Thr Gly Glu Gly Glu Phe Ala Lys Val Thr Leu Thr Pro Gly Lys Lys
            260                 265                 270

His Arg Leu Arg Leu Val Asn Thr Gly Val Glu Asn His Phe Gln Leu
        275                 280                 285
```

```
Ser Leu Val Asn His Gln Phe Thr Ile Ile Gly Ala Asp Met Val Pro
    290                 295                 300

Val His Pro Arg Thr Val Asp Ser Leu Phe Leu Gly Val Gly Gln Arg
305                 310                 315                 320

Tyr Asp Ile Ile Ile Glu Ala Asn Gln Thr Pro Gly Asn Tyr Trp Phe
                325                 330                 335

Asn Ala Thr Phe Gly Gly Glu Gly Glu Cys Gly Thr Ser Asn Asn Lys
            340                 345                 350

Tyr Pro Ala Ala Ile Phe His Tyr Ser Ser Ala Pro Asp Ala Leu Pro
        355                 360                 365

Thr Asp Glu Gly Val Ala Pro Ile Asp His Asn Cys Leu Asp Leu Asp
    370                 375                 380

Asp Leu Glu Pro Ile Val Ser Glu Asp Val Pro Ile Ser Gly Phe Thr
385                 390                 395                 400

Asn Val His Glu Asp Thr Leu Asp Val His Leu Glu Thr His Pro Met
                405                 410                 415

Phe Val Trp Gln Ile Asn Gly Ser Ala Val Asn Val Asp Trp Ser Asp
            420                 425                 430

Pro Leu Ile Asp Tyr Val Ile Gln Gln Asn Thr Ser Phe Pro Pro Glu
        435                 440                 445

Tyr Asn Val Ile Glu Leu Ala Gln Ala Asn Gln Trp Thr Tyr Trp Leu
    450                 455                 460

Ile Gln Asn Asp Pro Gly Ala Thr Leu Ser Pro Pro His Pro Met His
465                 470                 475                 480

Leu His Gly His His Asp Phe Tyr Ile Leu Gly Arg Ser Pro Gly Val Ser
                485                 490                 495

Pro Ala Ser Arg Gln Leu Phe Arg Phe Asp Pro Lys Lys Asp Phe Gln
            500                 505                 510

Arg Leu Thr Thr His Lys Pro Met Lys Arg Asp Thr Ala Met Leu Pro
        515                 520                 525

Gly Phe Gly Trp Leu Leu Ile Ala Phe Arg Thr Asp Asn Pro Gly Ala
    530                 535                 540

Trp Val Phe His Cys His Ile Ala Trp His Val Ser Gly Gly Phe Ser
545                 550                 555                 560

Val Thr Tyr Leu Glu Arg Pro Asp Glu Leu Arg Gln Ser Leu Ser Gln
                565                 570                 575

Glu Asp Ile Asp Asp His Asn Arg Val Cys Gly Glu Trp Arg Glu Tyr
            580                 585                 590

Trp Pro Thr Ser Pro Phe Pro Lys Leu Asp Ser Gly Leu Arg His Arg
        595                 600                 605

Trp Val Glu Gln Ser Glu Trp Ser Ile Lys Val
    610                 615

<210> SEQ ID NO 33
<211> LENGTH: 1927
<212> TYPE: DNA
<213> ORGANISM: Penicillium oxalicum

<400> SEQUENCE: 33
atgaacgttt tgatttacct cctttttatgt ttcacagagt ggactcttgc cgctactgtc    60
tatttttcgg cccacttgac ttgggccaac cactcggtgg caggcgttga gcgtccggtc   120
atcctcacca atggccagta ccctggcccc gagttacgct tgaatcaggg agacgatgtg   180 attttgacg tgtataacga ttgtcccttt ggcatgacgg tgcactttca tggtgagaac   240
```

```
agaaacgcct cccaagcccc aactctccaa tcacccgcca gggagcttac tagaatctgt    300
catagggatt gaacagattg gcacaccatg gtcggatgga gtgcctggac tatcacagcg    360
cgctatcaaa acaggtgctg cctttcgtta tcgctggaag gcagatcagt atggcgctta    420
cttctatcat gctcatcatc ggggtcattt cgaggacggt ctgtacggtc cgatatacat    480
cgccccttca cgtactgtga ccaagccgtt cagcctcatc tcaagtagtt tcattcacca    540
acaggccatg aaacttgctg aaatcgcgac ctcgcccttta ttcttgtcgg attggcgctt    600
gttgacttcc gaacaaatct ggaatgccga ggaagcttcc ggtgtggacg cattctgcgc    660
gaatgctctg ctcatcaatg gcaaaggctc agtgacgtgc ttctcgcaag accagatcaa    720
tgagttgaca acgcccgagc aaaaagctgt tctgggtgac gagaccttga ctgatttagc    780
gtgggtgttc ctcttgtatc ccattccgac tggatgatga catgcaaaag agcgaaagcg    840
aaagcccaag cgctgatcca tttaattgat gtatagttgc ttcccgccaa acgttggaca    900
gggagattac cctcacaatt acagtgcgct actaccgacg atgttctatg gatgtaaccc    960
gactcaaggt ccacggcatg taattgatgc agatccaggt cgcagataca tcagcttgga    1020
tctcaccagt gcagccgggg tgattgatcc agtcttctcc atcgacgagc actttatgtg    1080
ggtatacgcg gtagatggac ggtacatcca accggtcaaa gtcaacgctc tcaccatccc    1140
catcggtaac agatactcgg ttcttgtgcc tctcgacaag accccagggg actatactgc    1200
ccgcttggtc agtgggagta ttcaacaaat tcttaacacc acagctattc tacactatca    1260
agctcccgac ttcctacgca ggccatcaag gccatggatc ccctgacag gtaccaacgc    1320 gacggccaac accgtcttct tgacgtgac caaagcccaa ccttaccccc cgattgctcc    1380
gtccaccaac atcgcagcga ctcacatcct aacaatccgt cgctttggcg catcgtaccg    1440
ctggacgctg ggaaacagca gctacgatct ggaattggaa gaatcccagc ccttactctt    1500
taatcagact gccatcccca gcgacttgat cgttcgcacc aacaacgaca cctggatcga    1560
tctcattatc caagttgatt cacctgctca gccggcgcat ccaattcata aacactccaa    1620
caagcatttc gcaattggtc agggtctcgg gaattttaca tggacatcgg tcgcggaagc    1680
gatgcaatca attcctgagt cattcaattt gatcaatccg ccgatcaaag acacaactcc    1740
gactcctgcc acgggcactg gtcccagttg gctggctctt cggtatcacg ttgtgaatcc    1800
cggagctttt ctgttacatt gtcatgtgca gattcatcag agtgggggca tggccttggc    1860
cttgttggat ggagtcaacg aatggcccac tgtacctttg aaatatttga ataattcagg    1920
gttctag                                                              1927
```

<210> SEQ ID NO 34
<211> LENGTH: 585
<212> TYPE: PRT
<213> ORGANISM: Penicillium oxalicum

<400> SEQUENCE: 34

```
Met Asn Val Leu Ile Tyr Leu Leu Leu Cys Phe Thr Glu Trp Thr Leu
1               5                   10                  15

Ala Ala Thr Val Tyr Phe Ser Ala His Leu Thr Trp Ala Asn His Ser
            20                  25                  30

Val Ala Gly Val Glu Arg Pro Val Ile Leu Thr Asn Gly Gln Tyr Pro
        35                  40                  45

Gly Pro Glu Leu Arg Leu Asn Gln Gly Asp Asp Val Ile Phe Asp Val
    50                  55                  60
```

-continued

```
Tyr Asn Asp Cys Pro Phe Gly Met Thr Val His Phe His Gly Ile Glu
 65                  70                  75                  80

Gln Ile Gly Thr Pro Trp Ser Asp Gly Val Pro Gly Leu Ser Gln Arg
                 85                  90                  95

Ala Ile Lys Thr Gly Ala Ala Phe Arg Tyr Arg Trp Lys Ala Asp Gln
            100                 105                 110

Tyr Gly Ala Tyr Phe Tyr His Ala His His Arg Gly His Phe Glu Asp
        115                 120                 125

Gly Leu Tyr Gly Pro Ile Tyr Ile Ala Pro Ser Arg Thr Val Thr Lys
    130                 135                 140

Pro Phe Ser Leu Ile Ser Ser Ser Phe Ile His Gln Gln Ala Met Lys
145                 150                 155                 160

Leu Ala Glu Ile Ala Thr Ser Pro Leu Phe Leu Ser Asp Trp Arg Leu
                165                 170                 175

Leu Thr Ser Glu Gln Ile Trp Asn Ala Glu Glu Ala Ser Gly Val Asp
            180                 185                 190

Ala Phe Cys Ala Asn Ala Leu Leu Ile Asn Gly Lys Gly Ser Val Thr
        195                 200                 205

Cys Phe Ser Gln Asp Gln Ile Asn Glu Leu Thr Thr Pro Glu Gln Lys
    210                 215                 220

Ala Val Leu Gly Asp Glu Thr Leu Thr Asp Leu Ala Cys Phe Pro Pro
225                 230                 235                 240

Asn Val Gly Gln Gly Asp Tyr Pro His Asn Tyr Ser Ala Leu Leu Pro
                245                 250                 255

Thr Met Phe Tyr Gly Cys Asn Pro Thr Gln Gly Pro Arg His Val Ile
            260                 265                 270

Asp Ala Asp Pro Gly Arg Arg Tyr Ile Ser Leu Asp Leu Thr Ser Ala
        275                 280                 285

Ala Gly Val Ile Asp Pro Val Phe Ser Ile Asp Glu His Phe Met Trp
    290                 295                 300

Val Tyr Ala Val Asp Gly Arg Tyr Ile Gln Pro Val Lys Val Asn Ala
305                 310                 315                 320

Leu Thr Ile Pro Ile Gly Asn Arg Tyr Ser Val Leu Val Pro Leu Asp
                325                 330                 335

Lys Thr Pro Gly Asp Tyr Thr Ala Arg Leu Val Ser Gly Ser Ile Gln
            340                 345                 350

Gln Ile Leu Asn Thr Thr Ala Ile Leu His Tyr Gln Ala Pro Asp Phe
        355                 360                 365

Leu Arg Arg Pro Ser Arg Pro Trp Ile Thr Leu Thr Gly Thr Asn Ala
    370                 375                 380

Thr Ala Asn Thr Val Phe Phe Asp Val Thr Lys Ala Gln Pro Tyr Pro
385                 390                 395                 400

Pro Ile Ala Pro Ser Thr Asn Ile Ala Ala Thr His Ile Leu Thr Ile
                405                 410                 415

Arg Arg Phe Gly Ala Ser Tyr Arg Trp Thr Leu Gly Asn Ser Ser Tyr
            420                 425                 430

Asp Leu Glu Leu Glu Glu Ser Gln Pro Leu Leu Phe Asn Gln Thr Ala
        435                 440                 445

Ile Pro Ser Asp Leu Ile Val Arg Thr Asn Asn Asp Thr Trp Ile Asp
    450                 455                 460

Leu Ile Ile Gln Val Asp Ser Pro Ala Gln Pro Ala His Pro Ile His
465                 470                 475                 480

Lys His Ser Asn Lys His Phe Ala Ile Gly Gln Gly Leu Gly Asn Phe
```

|   |   | 485 |   |   |   |   | 490 |   |   |   |   | 495 |   |   |
|---|---|---|---|---|---|---|---|---|---|---|---|---|---|---|
Thr Trp Thr Ser Val Ala Glu Ala Met Gln Ser Ile Pro Glu Ser Phe
            500                       505                   510

Asn Leu Ile Asn Pro Pro Ile Lys Asp Thr Thr Pro Thr Pro Ala Thr
            515                       520                   525

Gly Thr Gly Pro Ser Trp Leu Ala Leu Arg Tyr His Val Val Asn Pro
            530                       535                   540

Gly Ala Phe Leu Leu His Cys His Val Gln Ile His Gln Ser Gly Gly
545                       550                       555                   560

Met Ala Leu Ala Leu Leu Asp Gly Val Asn Glu Trp Pro Thr Val Pro
            565                       570                   575

Leu Lys Tyr Leu Asn Asn Ser Gly Phe
            580                       585

<210> SEQ ID NO 35
<211> LENGTH: 2053
<212> TYPE: DNA
<213> ORGANISM: Penicillium oxalicum

<400> SEQUENCE: 35
atggctccat tgcgcactct cctgcctctt gtggcttcga gtttcttctc acaagcatgg      60
gcaaagcatg ttcaatttga gttggaccta acatggcaga aaggatctcc gaacggaaac     120
gttcgggaga tgatttcat gaatgatcaa ttcccgggcc ggagctgcg cctagatcag     180 ggcgatgatg tggaggtttg tgccctgtca aaagtgccgg aagcttgag attctgatat     240 cttcacagtt cattgtgcat aatcatctgc ctttccaaac atccattcac tttcatggga     300
tcgagcagct gggtactcca tggtcagatg gggtgcctgg tttaacgcag aagcccattc     360
agcccggccg gagctggaca tatcgctgga aagctactca gtatgaaaca tactggtacc     420
atgcccacat caaatcagag atgatggatg cctctacgg accgatatgg atcaagtaag     480
accatgttca tggaaacatt gtgtgatttc ttctaaccgc tcagtccctt ccctgataac    540
ccccgatccg ttccatctta tctccaacaa tgcggaagat atcgaggcga tgcgcaaggc     600
ggagaaaaat ccgcacttgg tcatcctttc ggactgggaa aaattgaccg catcgcaata     660
tcaacaggca caggttgata gccgactcaa tattgcgtaa ggccgacctt gattcaacac     720
gctggaaata gcctcaacat gtgctaattt gaaaacagat gcatggacag tattctcgtg     780
aacggtcggg gtgctgtta ctgccctggc ccgacaaaa tctcatctgt ggaacttccg     840
tatctgcaat cccttgttgc cgatgactcc ttgacggaca aagggtaagt gaccagatca     900
gaaatgtggt cttggcttcg tccagtaaga tttctgactt tgacgtgtgc gacgcagatg     960
cctgcccttt aattatcaga ctcaaggtga ctttccaccg atacccggg atcgtctccc    1020 ggagggactt cattcaggct gtgttccaac cgacgggag catgagatta tcgaagttga    1080
tcctcaagac aaatgggtgg ctctcaagtt catcagtgct gcctctttga aagcattcat    1140
gttctcgatt gacgagcacc gtatgtggat ctacgaggtc gacggcggct acatggagcc    1200
gctcacagcg gacagtgttc ctctttacca cggggagcgc tacggtgtaa tgctgaagct    1260
tgaccaaccg gtgaaagact acaccatccg cgttcccgac acgcaggatg atcaggtcat    1320
ttcaggcttc gccactctgc gctacaaggg ctcctctggc tccacctcgg agccgtcaaa    1380
gccgtttgtg gattatggcg ggcggaacac aacggcgtcg gtgactaaat tggagcccaa    1440
gttcattcat ccttacccgg ccgtcaccat cccgcagact gccgaccaga tggtgaatct    1500
tactctgggt cgggttgggt cctcctacac atggacagcc gccggtggtg cattgtatga    1560

```
cgtgatggcc aactgggatg accccatcct gtatgatctg gacgccgaga agaacctcgc   1620
ggaccaagtc accattcaaa cgaaaaatgg gacatgggtt gatctcctgc tgcagctggg   1680
agagatgccg cacacctcga gtacccaagc cccgcatgtg atgcacaagc actccaacaa   1740
ggcttacatc ctgggagttg gccaggcat ctttcaatgg tccagcaccg aagaagctat    1800
gaaggagcac ccggagctgt tccatctcga gaacccgcaa cgacgtgata cttttgtcac   1860
catcagcccc caaggaggtc ctatctggat gatgttacga tatcaggtgg tcaaccctgg   1920
cccattattt ctccactgtc acatcgagac ccacttgagc aacggcatgg ccattgcttt   1980
gctggacggc atcgatgagt ggcctcaagt tcccgcaggt gtggaccaaa gcccccgtgc   2040
ccatagaaac tga                                                     2053
```

<210> SEQ ID NO 36
<211> LENGTH: 604
<212> TYPE: PRT
<213> ORGANISM: Penicillium oxalicum

<400> SEQUENCE: 36

Met Ala Pro Leu Arg Thr Leu Leu Pro Leu Val Ala Ser Ser Phe Phe
1               5                   10                  15

Ser Gln Ala Trp Ala Lys His Val Gln Phe Glu Leu Asp Leu Thr Trp
            20                  25                  30

Gln Lys Gly Ser Pro Asn Gly Asn Val Arg Glu Met Ile Phe Met Asn
        35                  40                  45

Asp Gln Phe Pro Gly Pro Glu Leu Arg Leu Asp Gln Gly Asp Asp Val
    50                  55                  60

Glu Phe Ile Val His Asn His Leu Pro Phe Gln Thr Ser Ile His Phe
65                  70                  75                  80

His Gly Ile Glu Gln Leu Gly Thr Pro Trp Ser Asp Gly Val Pro Gly
                85                  90                  95

Leu Thr Gln Lys Pro Ile Gln Pro Gly Arg Ser Trp Thr Tyr Arg Trp
            100                 105                 110

Lys Ala Thr Gln Tyr Gly Thr Tyr Trp Tyr His Ala His Ile Lys Ser
        115                 120                 125

Glu Met Met Asp Gly Leu Tyr Gly Pro Ile Trp Ile Asn Pro Ser Pro
    130                 135                 140

Asp Thr Pro Asp Pro Phe His Leu Ile Ser Asn Asn Ala Glu Asp Ile
145                 150                 155                 160

Glu Ala Met Arg Lys Ala Glu Lys Asn Pro His Leu Val Ile Leu Ser
                165                 170                 175

Asp Trp Asp Lys Leu Thr Ala Ser Gln Tyr Gln Gln Ala Gln Val Asp
            180                 185                 190

Ser Arg Leu Asn Ile Ala Cys Met Asp Ser Ile Leu Val Asn Gly Arg
        195                 200                 205

Gly Ala Val Tyr Cys Pro Gly Ala Asp Lys Ile Ser Ser Val Glu Leu
    210                 215                 220

Pro Tyr Leu Gln Ser Leu Val Ala Asp Ser Leu Thr Asp Lys Gly
225                 230                 235                 240

Cys Leu Pro Phe Asn Tyr Gln Thr Gln Gly Asp Phe Pro Pro Thr Tyr
                245                 250                 255

Pro Asp Arg Leu Pro Glu Gly Leu His Ser Gly Cys Val Pro Thr Asp
            260                 265                 270

Gly Glu His Glu Ile Ile Glu Val Asp Pro Gln Asp Lys Trp Val Ala

-continued

```
            275                 280                 285
Leu Lys Phe Ile Ser Ala Ala Ser Leu Lys Ala Phe Met Phe Ser Ile
    290                 295                 300
Asp Glu His Arg Met Trp Ile Tyr Glu Val Asp Gly Gly Tyr Met Glu
305                 310                 315                 320
Pro Leu Thr Ala Asp Ser Val Pro Leu Tyr His Gly Glu Arg Tyr Gly
                325                 330                 335
Val Met Leu Lys Leu Asp Gln Pro Val Lys Asp Tyr Thr Ile Arg Val
            340                 345                 350
Pro Asp Thr Gln Asp Asp Gln Val Ile Ser Gly Phe Ala Thr Leu Arg
        355                 360                 365
Tyr Lys Gly Ser Ser Gly Ser Thr Ser Glu Pro Ser Lys Pro Phe Val
    370                 375                 380
Asp Tyr Gly Gly Arg Asn Thr Thr Ala Ser Val Thr Lys Leu Glu Pro
385                 390                 395                 400
Lys Phe Ile His Pro Tyr Pro Ala Val Thr Ile Pro Gln Thr Ala Asp
                405                 410                 415
Gln Met Val Asn Leu Thr Leu Gly Arg Val Gly Ser Ser Tyr Thr Trp
            420                 425                 430
Thr Ala Ala Gly Gly Ala Leu Tyr Asp Val Met Ala Asn Trp Asp Asp
        435                 440                 445
Pro Ile Leu Tyr Asp Leu Asp Ala Glu Lys Asn Leu Ala Asp Gln Val
    450                 455                 460
Thr Ile Gln Thr Lys Asn Gly Thr Trp Val Asp Leu Leu Gln Leu
465                 470                 475                 480
Gly Glu Met Pro His Thr Ser Thr Gln Ala Pro His Val Met His
                485                 490                 495
Lys His Ser Asn Lys Ala Tyr Ile Leu Gly Val Gly Pro Gly Ile Phe
            500                 505                 510
Gln Trp Ser Ser Thr Glu Glu Ala Met Lys Glu His Pro Glu Leu Phe
        515                 520                 525
His Leu Glu Asn Pro Gln Arg Arg Asp Thr Phe Val Thr Ile Ser Pro
    530                 535                 540
Gln Gly Gly Pro Ile Trp Met Met Leu Arg Tyr Gln Val Val Asn Pro
545                 550                 555                 560
Gly Pro Phe Ile Leu His Cys His Ile Glu Thr His Leu Ser Asn Gly
                565                 570                 575
Met Ala Ile Ala Leu Leu Asp Gly Ile Asp Glu Trp Pro Gln Val Pro
            580                 585                 590
Ala Gly Val Asp Gln Ser Pro Arg Ala His Arg Asn
        595                 600
```

<210> SEQ ID NO 37
<211> LENGTH: 48
<212> TYPE: DNA
<213> ORGANISM: Artificial Sequence
<220> FEATURE:
<223> OTHER INFORMATION: Synthetic Construct

<400> SEQUENCE: 37
acacaactgg ggatccacca tgggtatctc tgcgatgttt tatctttg        48

<210> SEQ ID NO 38
<211> LENGTH: 37
<212> TYPE: DNA
<213> ORGANISM: Artificial Sequence

```
<220> FEATURE:
<223> OTHER INFORMATION: Synthetic Construct

<400> SEQUENCE: 38
gtcaccctct agatcttatg ggctgcggca attacac                              37

<210> SEQ ID NO 39
<211> LENGTH: 38
<212> TYPE: DNA
<213> ORGANISM: Artificial Sequence
<220> FEATURE:
<223> OTHER INFORMATION: Synthetic Construct

<400> SEQUENCE: 39
acacaactgg ggatccacca tgtgtgactc gcgggttc                             38

<210> SEQ ID NO 40
<211> LENGTH: 40
<212> TYPE: DNA
<213> ORGANISM: Artificial Sequence
<220> FEATURE:
<223> OTHER INFORMATION: Synthetic Construct

<400> SEQUENCE: 40
gtcaccctct agatctcgat atccttggtt cgctcagaga                           40

<210> SEQ ID NO 41
<211> LENGTH: 49
<212> TYPE: DNA
<213> ORGANISM: Artificial Sequence
<220> FEATURE:
<223> OTHER INFORMATION: Synthetic Construct

<400> SEQUENCE: 41
acacaactgg ggatccacca tgtatctgtc caaggaattc ttctttgtc                 49

<210> SEQ ID NO 42
<211> LENGTH: 41
<212> TYPE: DNA
<213> ORGANISM: Artificial Sequence
<220> FEATURE:
<223> OTHER INFORMATION: Synthetic Construct

<400> SEQUENCE: 42
gtcaccctct agatctaaga gattctccag gcgaaagcta g                         41

<210> SEQ ID NO 43
<211> LENGTH: 49
<212> TYPE: DNA
<213> ORGANISM: Artificial Sequence
<220> FEATURE:
<223> OTHER INFORMATION: Synthetic Construct

<400> SEQUENCE: 43
acacaactgg ggatccacca tgtggtcact gtattgtata ctgctacta                 49

<210> SEQ ID NO 44
<211> LENGTH: 37
<212> TYPE: DNA
<213> ORGANISM: Artificial Sequence
<220> FEATURE:
<223> OTHER INFORMATION: Synthetic Construct

<400> SEQUENCE: 44
gtcaccctct agatcttgtg tacggtgagg aggtcag                              37
```

<210> SEQ ID NO 45
<211> LENGTH: 43
<212> TYPE: DNA
<213> ORGANISM: Artificial Sequence
<220> FEATURE:
<223> OTHER INFORMATION: Synthetic Construct

<400> SEQUENCE: 45
acacaactgg ggatccacca tgaagactta ctgcgcactc ttg          43

<210> SEQ ID NO 46
<211> LENGTH: 43
<212> TYPE: DNA
<213> ORGANISM: Artificial Sequence
<220> FEATURE:
<223> OTHER INFORMATION: Synthetic Construct

<400> SEQUENCE: 46
gtcaccctct agatcttcga aatacacact actcctgttg cac          43

<210> SEQ ID NO 47
<211> LENGTH: 50
<212> TYPE: DNA
<213> ORGANISM: Artificial Sequence
<220> FEATURE:
<223> OTHER INFORMATION: Synthetic Construct

<400> SEQUENCE: 47
acacaactgg ggatccacca tgtcacatat ttttcaacta atacactttc    50

<210> SEQ ID NO 48
<211> LENGTH: 36
<212> TYPE: DNA
<213> ORGANISM: Artificial Sequence
<220> FEATURE:
<223> OTHER INFORMATION: Synthetic Construct

<400> SEQUENCE: 48
gtcaccctct agatctgtgg gaagagggaa tctttc                  36

<210> SEQ ID NO 49
<211> LENGTH: 37
<212> TYPE: DNA
<213> ORGANISM: Artificial Sequence
<220> FEATURE:
<223> OTHER INFORMATION: Synthetic Construct

<400> SEQUENCE: 49
acacaactgg ggatccacca tggcgccaaa agggtcc                 37

<210> SEQ ID NO 50
<211> LENGTH: 39
<212> TYPE: DNA
<213> ORGANISM: Artificial Sequence
<220> FEATURE:
<223> OTHER INFORMATION: Synthetic Construct

<400> SEQUENCE: 50
gtcaccctct agatctcaga tgccagaaga cggactagg               39

<210> SEQ ID NO 51
<211> LENGTH: 46
<212> TYPE: DNA
<213> ORGANISM: Artificial Sequence
<220> FEATURE:
<223> OTHER INFORMATION: Synthetic Construct

```
<400> SEQUENCE: 51
acacaactgg ggatccacca tgaaactctg gtttccagtc ttttgc                    46

<210> SEQ ID NO 52
<211> LENGTH: 35
<212> TYPE: DNA
<213> ORGANISM: Artificial Sequence
<220> FEATURE:
<223> OTHER INFORMATION: Synthetic Construct

<400> SEQUENCE: 52
gtcaccctct agatctcgat aatgcggcat gccag                                35

<210> SEQ ID NO 53
<211> LENGTH: 55
<212> TYPE: DNA
<213> ORGANISM: Artificial Sequence
<220> FEATURE:
<223> OTHER INFORMATION: Synthetic Construct

<400> SEQUENCE: 53
acacaactgg ggatccacca tggggatagc acttagatta ctatatacaa catat          55

<210> SEQ ID NO 54
<211> LENGTH: 43
<212> TYPE: DNA
<213> ORGANISM: Artificial Sequence
<220> FEATURE:
<223> OTHER INFORMATION: Synthetic Construct

<400> SEQUENCE: 54
gtcaccctct agatctacgt aaatctatcg actatcgtcg tct                       43

<210> SEQ ID NO 55
<211> LENGTH: 34
<212> TYPE: DNA
<213> ORGANISM: Artificial Sequence
<220> FEATURE:
<223> OTHER INFORMATION: Synthetic Construct

<400> SEQUENCE: 55
acacaactgg ggatccacca tggcctcgct gatg                                 34

<210> SEQ ID NO 56
<211> LENGTH: 42
<212> TYPE: DNA
<213> ORGANISM: Artificial Sequence
<220> FEATURE:
<223> OTHER INFORMATION: Synthetic Construct

<400> SEQUENCE: 56
gtcaccctct agatctcgtg gatcatggat catgcttata ag                        42

<210> SEQ ID NO 57
<211> LENGTH: 49
<212> TYPE: DNA
<213> ORGANISM: Artificial Sequence
<220> FEATURE:
<223> OTHER INFORMATION: Synthetic Construct

<400> SEQUENCE: 57
acacaactgg ggatccacca tgtctttcgt taactcacta ttccttctc                 49

<210> SEQ ID NO 58
```

```
<211> LENGTH: 40
<212> TYPE: DNA
<213> ORGANISM: Artificial Sequence
<220> FEATURE:
<223> OTHER INFORMATION: Synthetic Construct

<400> SEQUENCE: 58
gtcaccctct agatctcagt gactgcaact tcaaacaagc                    40

<210> SEQ ID NO 59
<211> LENGTH: 41
<212> TYPE: DNA
<213> ORGANISM: Artificial Sequence
<220> FEATURE:
<223> OTHER INFORMATION: Synthetic Construct

<400> SEQUENCE: 59
acacaactgg ggatccacca tggcaccact aaggtcgctt c                  41

<210> SEQ ID NO 60
<211> LENGTH: 43
<212> TYPE: DNA
<213> ORGANISM: Artificial Sequence
<220> FEATURE:
<223> OTHER INFORMATION: Synthetic Construct

<400> SEQUENCE: 60
gtcaccctct agatctacag aaaataccgc tacaggaaca agc                43

<210> SEQ ID NO 61
<211> LENGTH: 34
<212> TYPE: DNA
<213> ORGANISM: Artificial Sequence
<220> FEATURE:
<223> OTHER INFORMATION: Synthetic Construct

<400> SEQUENCE: 61
acacaactgg ggatccacca tgtttcgacc ggcc                          34

<210> SEQ ID NO 62
<211> LENGTH: 40
<212> TYPE: DNA
<213> ORGANISM: Artificial Sequence
<220> FEATURE:
<223> OTHER INFORMATION: Synthetic Construct

<400> SEQUENCE: 62
gtcaccctct agatctgtct caaacggtct caaagggaag                    40

<210> SEQ ID NO 63
<211> LENGTH: 39
<212> TYPE: DNA
<213> ORGANISM: Artificial Sequence
<220> FEATURE:
<223> OTHER INFORMATION: Synthetic Construct

<400> SEQUENCE: 63
acacaactgg ggatccacca tggctgcaag gtgtcttgg                     39

<210> SEQ ID NO 64
<211> LENGTH: 38
<212> TYPE: DNA
<213> ORGANISM: Artificial Sequence
<220> FEATURE:
<223> OTHER INFORMATION: Synthetic Construct

<400> SEQUENCE: 64
```

```
gtcaccctct agatctggaa taccgcgatt aaacggtg                           38
```

<210> SEQ ID NO 65
<211> LENGTH: 38
<212> TYPE: DNA
<213> ORGANISM: Artificial Sequence
<220> FEATURE:
<223> OTHER INFORMATION: Synthetic Construct

<400> SEQUENCE: 65

```
acacaactgg ggatccacca tgaaaccgtt catcagcg                           38
```

<210> SEQ ID NO 66
<211> LENGTH: 39
<212> TYPE: DNA
<213> ORGANISM: Artificial Sequence
<220> FEATURE:
<223> OTHER INFORMATION: Synthetic Construct

<400> SEQUENCE: 66

```
gtcaccctct agatctcttc cccatcttct gtcagtttg                          39
```

<210> SEQ ID NO 67
<211> LENGTH: 48
<212> TYPE: DNA
<213> ORGANISM: Artificial Sequence
<220> FEATURE:
<223> OTHER INFORMATION: Synthetic Construct

<400> SEQUENCE: 67

```
acacaactgg ggatccacca tgaacgtttt gatttacctc cttttatg                48
```

<210> SEQ ID NO 68
<211> LENGTH: 47
<212> TYPE: DNA
<213> ORGANISM: Artificial Sequence
<220> FEATURE:
<223> OTHER INFORMATION: Synthetic Construct

<400> SEQUENCE: 68

```
gtcaccctct agatctgagt ttcacagaaa aactagaaac ttcaagg                 47
```

<210> SEQ ID NO 69
<211> LENGTH: 38
<212> TYPE: DNA
<213> ORGANISM: Artificial Sequence
<220> FEATURE:
<223> OTHER INFORMATION: Synthetic Construct

<400> SEQUENCE: 69

```
acacaactgg ggatccacca tggctccatt gcgcactc                           38
```

<210> SEQ ID NO 70
<211> LENGTH: 37
<212> TYPE: DNA
<213> ORGANISM: Artificial Sequence
<220> FEATURE:
<223> OTHER INFORMATION: Synthetic Construct

<400> SEQUENCE: 70

```
gtcaccctct agatctagcc atccgactcg acgatag                            37
```